United States Patent
Hardee et al.

(10) Patent No.: US 9,364,495 B2
(45) Date of Patent: Jun. 14, 2016

(54) ORAL DELIVERY OF THERAPEUTICALLY EFFECTIVE LNA OLIGONUCLEOTIDES

(75) Inventors: Gregroy Hardee, Del Mar, CA (US); Ellen Marie Straarup, Birkerod (DK); Marie Wickstrom Lindholm, Malmo (SE); Henrik Orum, Vaerlose (DK); Henrik Hansen, Roedovre (DK)

(73) Assignee: Roche Innovation Center Copenhagen A/S, Hoersholm (DK)

( * ) Notice: Subject to any disclaimer, the term of this patent is extended or adjusted under 35 U.S.C. 154(b) by 254 days.

(21) Appl. No.: 13/503,189

(22) PCT Filed: Oct. 20, 2010

(86) PCT No.: PCT/EP2010/065766
§ 371 (c)(1),
(2), (4) Date: Sep. 5, 2012

(87) PCT Pub. No.: WO2011/048125
PCT Pub. Date: Apr. 28, 2011

(65) Prior Publication Data
US 2012/0322851 A1    Dec. 20, 2012

Related U.S. Application Data

(60) Provisional application No. 61/253,090, filed on Oct. 20, 2009, provisional application No. 61/321,892, filed on Apr. 8, 2010.

(51) Int. Cl.
*C07H 21/04* (2006.01)
*C07H 21/02* (2006.01)
*A61K 48/00* (2006.01)
*C12N 15/85* (2006.01)
*A61K 31/712* (2006.01)
*C12N 15/113* (2010.01)

(52) U.S. Cl.
CPC .......... *A61K 31/712* (2013.01); *C12N 15/1136* (2013.01); *C12N 2310/11* (2013.01); *C12N 2310/113* (2013.01); *C12N 2310/315* (2013.01); *C12N 2310/3231* (2013.01); *C12N 2310/3341* (2013.01)

(58) Field of Classification Search
CPC .......................... C12N 15/111; C12N 15/113
See application file for complete search history.

(56) References Cited

U.S. PATENT DOCUMENTS

2007/0275919 A1* 11/2007 Gryaznov et al. ............... 514/44

FOREIGN PATENT DOCUMENTS

| WO | WO2007/031081 | 3/2007 |
|----|---------------|--------|
| WO | WO2007/112753 | 10/2007 |
| WO | WO2008/043753 | 4/2008 |
| WO | WO2008/086807 | 7/2008 |
| WO | WO2008/113830 | 9/2008 |
| WO | WO2008/113832 | 9/2008 |
| WO | WO2008/131807 | 11/2008 |
| WO | WO2009/043353 | 4/2009 |
| WO | WO2011/048125 | 4/2011 |

OTHER PUBLICATIONS

International Search Report and Written Opinion for corresponding PCT Application No. PCT/EP2010/065766, dated Feb. 4, 2011, pp. 1-14.
Roberts et al., "Efficient and Persistent Splice Switching by Systemically Delivered LNA Oligonucleotides in Mice," Molecular Therapy, 14(4):471-475 (2006).

* cited by examiner

*Primary Examiner* — Amy Bowman
(74) *Attorney, Agent, or Firm* — Fish & Richardson P.C.

(57) ABSTRACT

The invention provides for LNA oligomers, for the treatment of a metabolic or liver disorder, wherein the LNA oligomer is administered orally in a unit dose of less than 50 mgs/kg, wherein the LNA oligomer is administered in the presence of a penetration (permeation) enhancer.

17 Claims, 5 Drawing Sheets

ORAL DELIVERY OF THERAPEUTICALLY EFFECTIVE LNA OLIGONUCLEOTIDES

This application is the U.S. national stage under 35 USC §371 of International Application Number PCT/EP2010/065766, filed on 20 Oct. 2010, which claims priority to U.S. Application No. 61/523,090, filed on 20 Oct. 2009; and U.S. Application No. 61/321,892 filed 8 Apr. 2010, the entire contents of which applications is hereby incorporated by reference.

FIELD OF INVENTION

The present invention relates to the oral delivery of LNA oligonucleotides, particularly for therapeutic applications.

BACKGROUND

To date the effective and efficient oral delivery of antisense therapeutics has remained an elusive goal (Tillman 2008). Indeed, oral delivery of oligonucleotide therapeutics has been the subject of considerable research, but despite the concerted efforts, sufficient bioavailability of intact and functional oligonucleotide and the resulting therapeutic benefit has not yet been validated. Modification of oligonucleotide chemistry has created molecules stable enough to survive the intestinal environment; however, efficient absorption has been limited by molecular permeability (Hardee 2006). Mean oral bioavailability of Mipopersen (ISIS 301012) in human clinical trials was only 6% (Hardee et al., 2006 Antisense Drug Technology, Ed. Crooke, 2nd Edition, Chapter 8). The clinical trial ISIS 301012 was terminated, and development has continued based on IV administration.

Oral delivery of oligonucleotides is particularly problematic due to the combined effects of extremes of pH within the digestive tract and the dilution effect, as well as inefficient absorption and transfer to the circulatory system. For example, the acidity of the stomach environment leads to depurination of purine bases and acid hydrolysis of the backbone of the oligonucleotide causes substantial degradation of the oligonucleotide.

Whilst one possible solution to the permeability problem may be to reduce the size of the therapeutic construct (Khatsenko 2000, Tsutsumi 2008), this creates the challenge of maintaining the required affinity, specificity and ultimately, potency of the antisense therapeutic. Shortening the length of oligonucleotides for oral delivery further raises the prospect that problems of oligonucleotide stability will be exascerbated as the effect of oligonucleotide degradation within the digestive tract will have proportionately a greater effect on shorter oligonucleotides than a longer one.

Khatsenko et al., Antisense & Nucleic Acid Drug Development 2000; 10:35-44 reports on the enhanced intestinal of PS-MOE oligonucleotides as compared to unmodified PS-ODN and that permeability increased linearly with decreasing length.

Tillman et al., J. Pharm. Sci. 2008; 97(1); 225-36 reports on the oral absorption of 2'MOE antisense oligonucleotides in healthy volunteers and that by pulsed delivery of the penetration enhancer sodium caprate, average plasma bioavailability of 9.5% was achieved. Tillman suggest that formulations can be devised that allow oral administration of oligonucleotides.

Herein, we disclose our surprising observation that Locked Nucleic Acid (LNA) oligonucleotides survive oral administration and are effectively absorbed in the mammalian digestive tract and provide a clear therapeutic benefit—i.e. they are not only bioavailable in sufficient quantities, but they survive in an intact and therapeutically active form, even without sophisticated formulation. Quite remarkably, the present inventors have found that LNA oligomers delivered simply with diet is effective in eliciting a therapeutically effective response.

LNA possess the necessary stability, potency and permeability to make oral dosing feasible, and is sufficiently robust to ensure the maintenance of the integrity of the oligonucleotide during oral administration to delivery to the site of therapeutic activity.

The present inventors have therefore identified LNA as a surprisingly superior chemistry for oral delivery, a chemistry which provides a robust therapeutic benefit to orally administered antisense compounds. Indeed, lower dosages of LNA oligomer can be administered whilst retaining pharmacological relevance, and surprisingly it was found that use of lower dosages or lower concentration of LNA oligomers, higher oral bioavailability could be obtained, especially when used in conjunction with a penetration enhancer.

SUMMARY OF INVENTION

The invention provides for an oligomer, such as a LNA oligomer, for the treatment of a disease or disorder, such as a systemic disorder, such as a metabolic disorder, or a liver disorder, wherein the oligomer, such as a LNA oligomer is administered orally in a unit dose of less than 50 mgs/kg, wherein the oligomer, such as LNA oligomer is administered in the presence of a penetration enhancer.

The invention provides for the use of an oligomer, such as an LNA oligomer for the manufacture of a medicament, wherein the medicament is for the treatment of a disease or disorder, such as a metabolic or liver disorder, wherein the oligomer, such as the LNA oligomer is administered orally in a unit dose of less than 50 mgs/kg, wherein the oligomer, such as the LNA oligomer is administered in the presence of a penetration enhancer.

The invention provides for a method of treatment of a disease or disorder, such as a metabolic or liver disorder, said method comprising orally administering a therapeutically effective amount of an oligomer, such as a LNA oligomer, to a subject in need of treatment, wherein the oligomer, such as the LNA oligomer is administered orally in a unit dose of less than 50 mgs/kg, wherein the oligomer, such as the LNA oligomer is administered in the presence of a penetration enhancer.

The invention provides for method of inhibiting a microRNA or mRNA in vivo in a mammal, such as a human, said method comprising administering an effective amount of a olgimer, such as a LNA oligomer, to a mammal, wherein the oligomer, such as the LNA oligomer, is administered orally in a unit dose of less than 50 mgs/kg, wherein the oligomer, such as the LNA oligomer is administered in the presence of a penetration enhancer.

Suitably, the oligomer and penetration enhancer is administered in an effective amount.

The invention provides a medicament composition, for oral administration to a subject in need of treatment, comprising an effective amount of at least one therapeutically effective LNA oligomer, and a pharmaceutically acceptable carrier. The medicament composition may be for use in medicine. The medicament composition is therefore an oral composition such as an oral pharmaceutical composition. Suitably the oral formulation is in the form of a unit dose of the LNA oligomer.

The invention provides a therapeutically effective LNA oligomer for use as a medicament for oral administration.

The invention provides for the use of a LNA oligomer for the manufacture of a medicament, wherein the medicament is for oral delivery.

The invention provides for a method of treatment of a medical disease or disorder, said method comprising administering a therapeutically effective amount of a LNA oligomer to a subject in need of said treatment, wherein said administration is one or more oral administrations (dosages) of said LNA oligomer.

The invention further provides for a method for modulating the expression of a nucleic acid (or a gene) in a mammal, comprising orally administering a LNA oligomer to the mammal. The nucleic acid (target), for example may be a mRNA or a microRNA. For example, the LNA oligomer may be a gapmer which targets a mRNA, or an antimiR or micromiR, which targets one or more microRNAs. Suitably the mRNA or microRNA is indicated in a medical condition or disease.

The invention provides a medicament composition, for oral administration to a subject in need of treatment, comprising an effective amount of at least one therapeutically effective microRNA modulating oligomer, and a pharmaceutically acceptable carrier. The medicament composition may be for use in medicine. The medicament composition is therefore an oral composition such as an oral pharmaceutical composition. Suitably the oral formulation is in the form of a unit dose of the anti-microRNA oligomer.

The microRNA modulating oligomer may, in some embodiments, be a anti-microRNA oligomer, a microRNA blockmer oligomer or a microRNA mimic.

The invention provides a therapeutically effective microRNA modulating oligomer, such as an anti-microRNA oligomer, for use as a medicament for oral administration.

The invention provides for the use of an microRNA modulating oligomer, such as an anti-microRNA oligomer, for the manufacture of a medicament, wherein the medicament is for oral delivery.

The invention provides for a method of treatment of a medical disease or disorder, said method comprising administering a therapeutically effective amount of microRNA modulating oligomer, such as an anti-microRNA oligomer, to a subject in need of said treatment, wherein said administration is one or more oral administrations (dosages) of said microRNA modulating oligomer, such as an anti-microRNA oligomer. The method may, in some embodiments, further comprise an initial step, carrier out prior to the oral administration of administering the microRNA modulating oligomer, such as an anti-microRNA oligomer, to the subject via a parenteral route.

The invention further provides for a method for modulating the expression of a nucleic acid (or a gene) in a mammal, comprising orally administering microRNA modulating oligomer, such as an anti-microRNA oligomer, to the mammal. The oligomer may, in some embodiments, be an antagomir, or an antimiR or micromiR, which targets one or more microRNAs. Suitably the microRNA is indicated in a medical condition or disease.

The invention further provides for a method for inhibiting the expression of a microRNA target in a mammal, comprising orally administering an anti-microRNA oligomer (or microRNA blockmer oligo) to the mammal. The oligomer may, in some embodiments, be an antagomir, or an antimiR or micromiR, which targets one or more microRNAs. Suitably the microRNA is indicated in a medical condition or disease. The method may, in some embodiments, further comprise an initial step, carrier out prior to the oral administration of administering the microRNA modulating oligomer, such as an anti-microRNA oligomer, to the subject via a parenteral route.

The invention provides a therapeutically effective microRNA modulating oligomer, such as an anti-microRNA oligomer, for use as a medicament for oral administration, in a subject, such as a mammal, a primate, such as a human being (e.g. patient), wherein the microRNA modulating oligomer, such as an anti-microRNA oligomer, is also administered to the subject, prior to administration of the oral administration, via a parenteral administration route.

The invention provides for the use of an microRNA modulating oligomer, such as an anti-microRNA oligomer, for the manufacture of a medicament, wherein the medicament is for oral delivery to a subject, wherein the microRNA modulating oligomer, such as an anti-microRNA oligomer, is also administered to the subject, prior to administration of the oral administration, via a parenteral administration route.

1A. Weekly serum cholesterol levels as percent of control, n=10 animals/group. 1B. Serum cholesterol levels during the two week wash-out period for the same treatment groups, where treatment with SPC3833 (in feed or as injections) was removed at start of wash-out, n=5 animals/group. 1C. Lipoprotein cholesterol distribution analyzed by FPLC, data illustrates the ratio between cholesterol content in HDL and non-HDL lipoproteins, n=6 animals/group.

Figure 2:
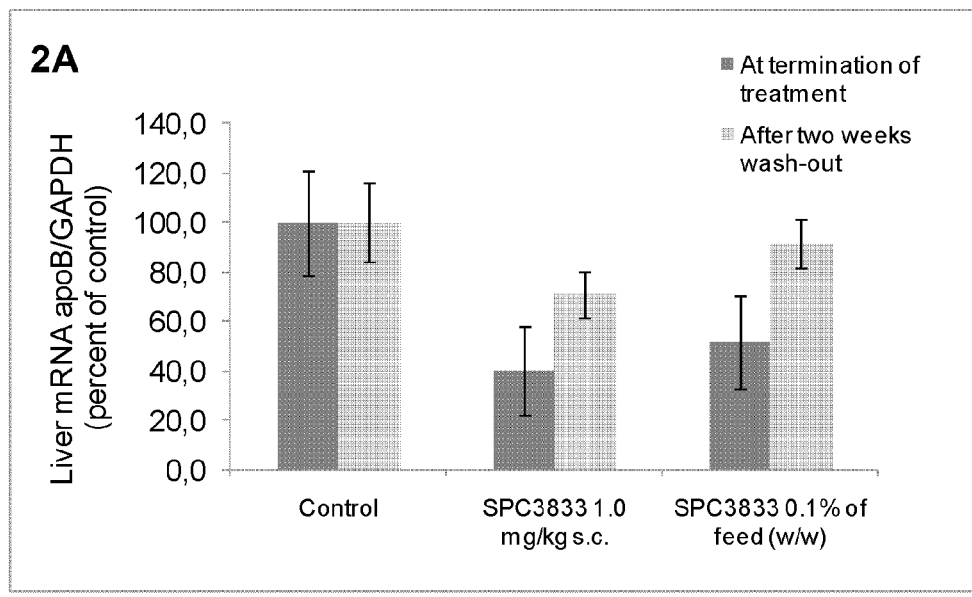

FIG. 2: ApoB mRNA levels

2A. Data represents liver apoB mRNA levels in livers from animals at termination of the six week treatment (dark grey) and at two weeks of wash-out after treatment (light grey). N=5 animals/group and time point.

Figure 3:
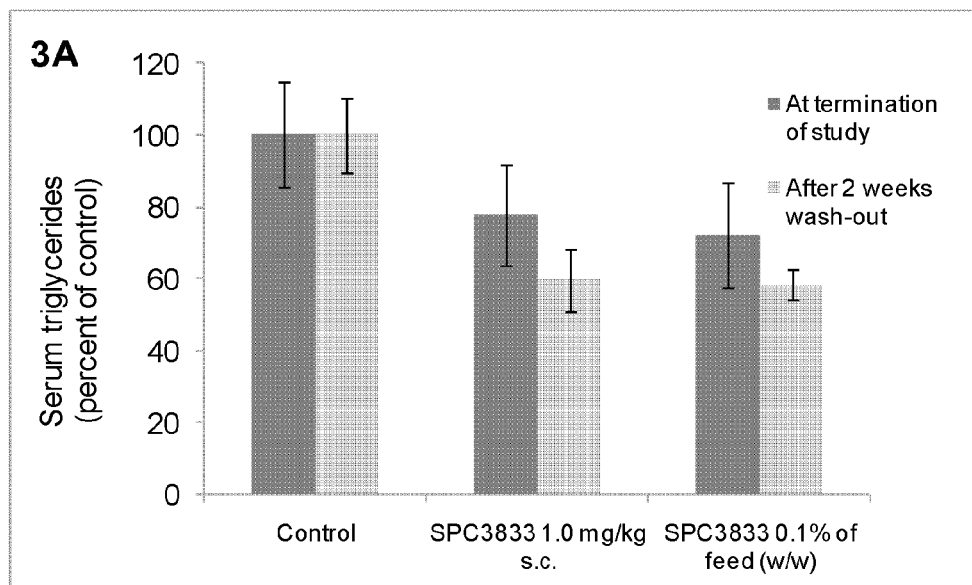

FIG. 3: Serum triglyceride and ALT levels

3A. Data represents serum triglyceride in animals at termination of the six week treatment (dark grey) and at two weeks of wash-out after treatment (light grey). N=10 animals/group at termination of study and n=5 animals/group after wash-out. 3B. Data represents serum ALT in animals at termination of the six week treatment (dark grey) and at two weeks of wash-out after treatment (light grey). N=5 animals/group and time point.

Figure 4:
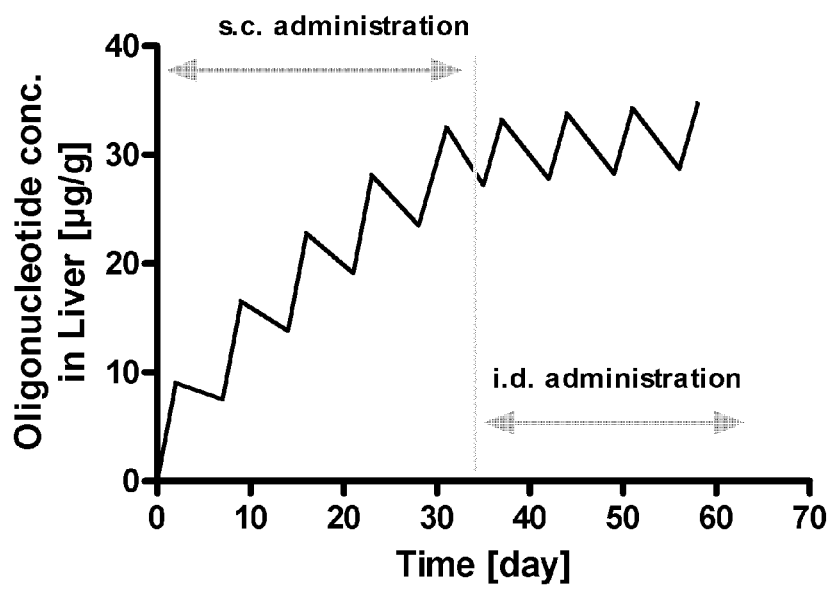

FIG. 4: Establishing and maintaining a desired concentration of oligonucleotide in the liver. The figure show the effect on liver concentration of weekly subcutaneous administration of 3 mg/kg for 5 consecutive weeks, followed by once weekly intraduodenal/intrajenunal administration of 33 mg/kg/administration of Compound B (+100 mg/kg Penetration enhancer and at a volume of 2-4 ml/kg).

Figure 5:
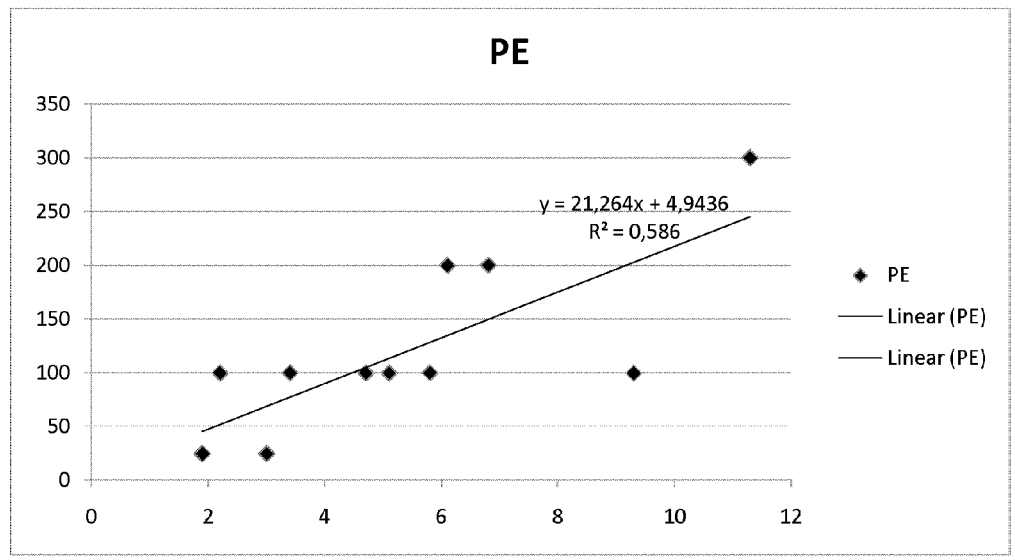

FIG. 5: Correlation between PE dose and LNA oligomer (A) bioavailability.

Figure 6:
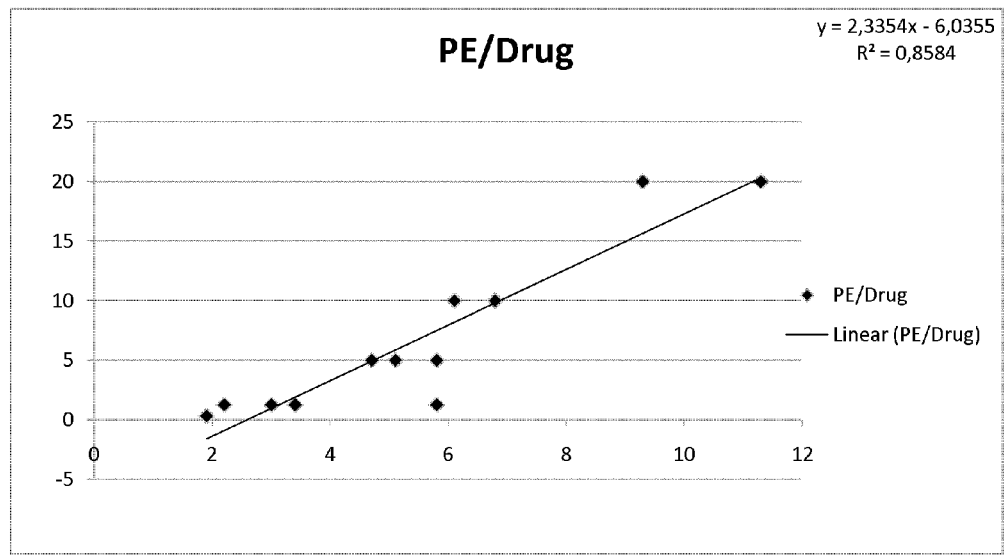

FIG. 6. Correlation between PE/Drug ratio and increasing bioavailability. X-axis=PE (C10) dose mg/kg. Y axis=BAV. Lower doses of LNA oligomer (A) drug have enhanced bioavailability in the presence of increasing concentration of PE—indicating that low doses of LNA oligomer can result in enhanced bioavailability when supplemented with enhanced levels of PE.

Figure 7:
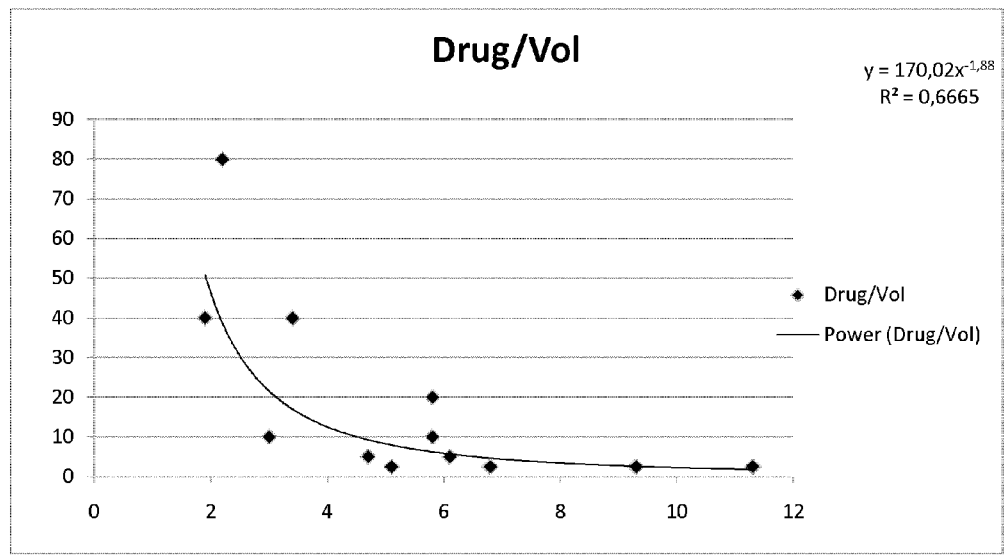

FIG. 7. Lower LNA oligomer (A) concentration resulted in increased bioavailability. X-axis=PE/drug ratio. Y axis=BAV. This study illustrates the benefit in low dose/high volume administration–typically achieved by oral administration with water or with food.

Figure 8:
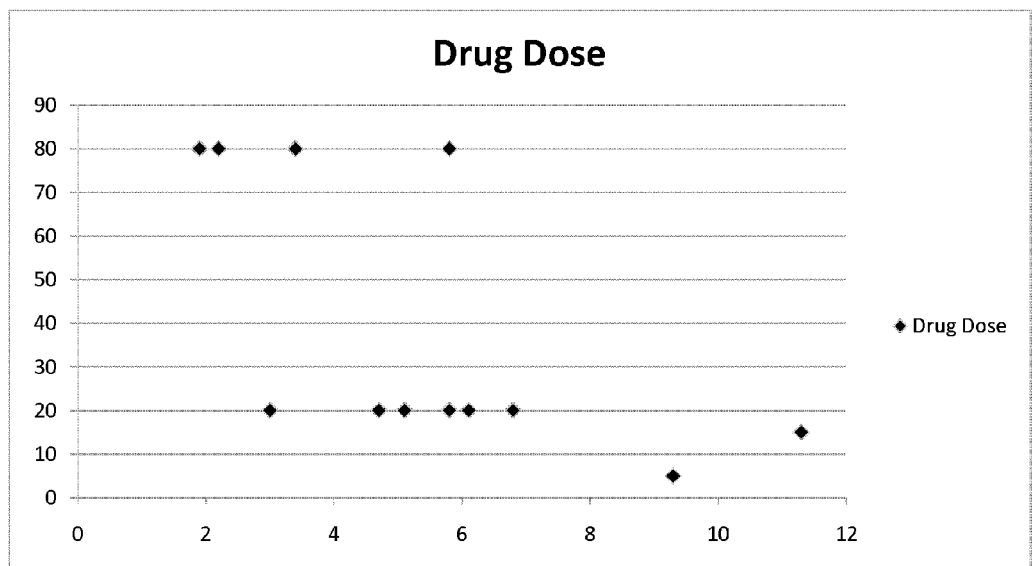

FIG. 8. Lower doses of LNA oligomer (A) (x axis—mg/kg) tend to result in higher bioavailability indicative of capacity limited absorption (Y-axis).

Figure 9:
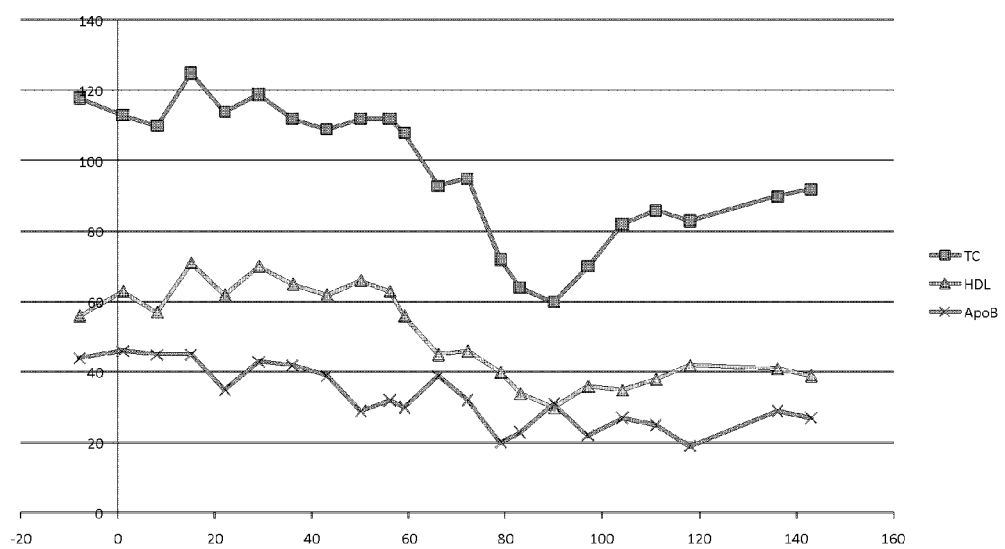

FIG. 9. In vivo pharmacology with orally administered LNA oligomers, with IV predosing. TC=total cholesterol. HDL=HDL cholesterol. ApoB=ApoB mRNA. Three LNA oligomer, A, B and D were sequentially administered (IJ), with each series of oral administrations preceded with an IV pre-dose. A was dosed 2 MPK IV on day 8 and then dose (PE and drug) escalated on days 15, 36, 43. B was dosed MPK IV on day 57 and the orally at 100 MPK on day 67. The oral BAV mean for this dose was =5.8%. C was dosed 5 MPK IV on day 81 and the orally at 100 MPK on day 91. The oral BAV mean for this dose was =4.4% See Example 5.

DETAILED DESCRIPTION OF INVENTION

Oral Formulations

The (at least one) oligomer, such as LNA oligomer, is formulated into an oral composition to allow for efficient administration to a subject. The oral composition is also referred to as a medicament composition for oral administration herein. Suitably the oral composition is in a unit dose form. The oral composition, or unit dose form thereof, is preferably in a solid formulation, such as a capsule, tablet or pill form. Suitably, for ease of swallowing, each unit dose form of the oral composition is less than 2 gms in weight, such as less than 1.5 gms, or less than 1 gm. In some embodiments, the unit dose form is between 250 mgs and 1500 mgs. A "pharmaceutically acceptable" component of a formulation of the invention is one which, when used together with excipients, diluents, stabilizers, preservatives and other ingredients are appropriate to the nature, composition and mode of administration of a formulation.

The formulated oral composition may comprise pharmaceutically acceptable binding agents and adjuvants. Capsules, tablets (pills) etc. may contain for example the following compounds: microcrystalline cellulose, gum or gelatin as binders; starch or lactose as excipients; stearates as lubricants; various sweetening or flavouring agents. For capsules the dosage unit may contain a liquid carrier like fatty oils. Likewise coatings of sugar or enteric agents may be part of the dosage unit. The oligonucleotide formulations may also be emulsions of the active pharmaceutical ingredients and a lipid forming a micellular emulsion. In some embodiments, the medicament is in a unit dose form, such as a tablet, a capsule or a pill.

In some embodiments, each unit dose may comprise a single capsule, tablet or pill (or similar solid form—such as those listed herein), or in some embodiments, may comprise, for example 2, 3 or 4 tablet or pills or capsules. The advantage of multiple tablet/capsule/pills for determining a unit dose is that patient specific dosages can be easily prescribed.

The amount of the oligomer, such as LNA oligomer, in the unit dose form will depend upon the efficacy of the oligomer, the therapeutic target and indication, the dosage regimen. In some embodiments, each unit dose comprises 1-500 mg oligomer, such as LNA oligomer, such as 20-100 mg. In some embodiments, the unit dose form will be administered at a dose of less than 50 mg/kg, such as less than 40 mg/kg, such as less than 30 mg/kg, such as less than 20 mg/kg, such as less than 10 mg/kg, such as less than 5 mg/kg, such as less than 1 mg/kg, such as less than 0.5 mg/kg, such as less than 0.1 mg/kg. In one embodiment, the dosage is calculated according to the oral bioavailability of the individual oligomer, to obtain a dosage that will allow maintenance of an effective concentration of the oligomer in the target tissue.

Surprisingly, it has been found that by using lower dosages of LNA oligomers, increased bioavailability may be achieved, particularly when used in conjunction with an effective amount of one or more penetration (permeation) enhancers (PE), such as sodium caprate (C10). The terms permeation enhancer and penetration enhancer are used interchangeably herein. In some embodiments, the LNA oligomer is administered in a dose of less than 50 mg/kg, such as less than 40 mg/kg, such as less than 30 mg/kg, such as less than 20 mg/kg, such as less than 10 mg/kg, such as less than 5 mg/kg, such as less than 1 mg/kg. In some embodiments the LNA oligomer is administered at a level above 1 mg/kg, such as above 5 mg/kg, such as above 10 mg/kg, such as above 15 mg/kg, such as above 20 mg/kg.

In some embodiments, the penetration enhancer may be used in conjunction with the oligomer at a ratio of at least 5:1, such as at least 10:1 or at least 20:1. Such ratios of PE/oligomer may be used with, when the oligomer is administered at a dosage level of less than 50 mg/kg, as described herein with respect to the LNA oligomer dosages. The oral composition the oligomer, such as LNA oligomer, may, in some embodiments comprise between (about) 0.5 and (about) 20% (w/w) of the oral composition, such as (about) 1%—(about) 10% (w/w). In some embodiments, the at least one oligomer, such as LNA oligomer, is dosed at a level of between 1 mg/kg and 200 mg/kg, as determined per kg of body mass of the subject in need of treatment. In some embodiments, the oral bioavailability (F) of the oligomer is at least 10%. Oral bioavailability may be measured in humans such as the subject or patient, or may be measured in a suitable aminel model, and data extrapolated back to humans. In this regards, in Cyanomologous monkeys, as illustrated in the examples, the oral bioavailability in humans is typically 1.3-1.6×.

In some embodiments, the oral medicament composition is encapsulated or is otherwise coated in an enteric material. In some embodiments, the oral composition is enterically coated. Enteric coating may improve the delivery of oligomer through the stomach into the site of absorption in the small intestine.

In some embodiments, the enteric coating is a pH controlled polymers such as; selected from the group consisting of cellulose acetate phthalate; cellulose acetate trimelliate; hydroxypropyl methylcellulose phthalate; hydroxypropyl methylcellulose acetate succinate; polyvinyl acetate phthalate; poly(methacrylic acid, methyl methacrylate) 1:1; poly (methacrylic acid, ethyl acrylate) 1:1; and compatible mixtures thereof.

The water content of the oral composition is typically reduced during manufacture to allow the solid or semi solid formulation. In some embodiments, some water is typically retained to ensure the integrity of the formulation such as to prevent cracking and crumbling. In some embodiments the water content of the oral formulation is less than about 90%. In some embodiments, the water content is less than 10% or 1-10%, or less than 5%, such as 1-5%, or even less than 1%. Suitably the water content of the oral formulation excludes the coating layer when present.

The oral composition, in addition to the oligomer, comprises a pharmaceutically acceptable carrier. In some embodiments the carrier is, or comprises, a disintegrant, such as a disintegrant selected from the group listed in the following table. The disintegrant may, in some embodiments make up (about) 1% to (about) 10% of the weight of the oral formulation.

| DISINTEGRANTS | SUGGESTED CONCENTRATION IN GRANULES/ FORMULATION (% W/W) |
|---|---|
| Starch USP | 5-20 |
| Starch 1500 | 5-15 |
| Avicel ®(PH 101, PH 102) | 10-20 |
| Solka floc ® | 5-15 |
| Alginic acid | 1-5 |
| Na alginate | 2.5-10 |
| Explotab ® | 2-8 |
| Polyplasdone ®(XL) | 0.5-5 |
| Amberlite ® (IPR 88) | 0.5-5 |
| Methyl cellulose, Na CMC, HPMC | 5-10 |
| AC-Di-Sol ® | 1-3 |
| Carbon dioxide | 2-4 |

In some embodiments, the oral medicament composition comprises a pharmaceutically acceptable excipient.

In some embodiments, the oral composition comprises penetration enhancers. Penetration enhancers (or concentrations thereof) that do not significantly stimulate g.i. motility are preferred—it may therefore be desirable to limit the amount of certain penetration enhancers so to prevent enhanced g.i. motility. In some embodiments, the penetration enhancer may be used at a dose of 0% to (about) 70%, such as sodium caprate (C10). In some embodiments, the penetration enhancer is dosed at a level less than 50 mgs per kg of body mass of the subject in need of treatment, such as less than 25 mgs/kg.

The oral composition, in some embodiments comprises less than 0.5% peroxide, such as less than 0.1% peroxide.

The oral composition may further comprise one or more or all of the following: excipients, chelating agents and surfactants. Suitably, in some embodiments, between 1-5% of such ingredients (individually) may be included. However, it should be noted that some ingredients have multiple functions, such some chelating agents also function as penetration enhancers. In some embodiments, the chelator is ethylenediaminetetraacetic acid, $(HO_2CCH_2)_2NCH_2CH_2N(CH_2CO_2H)_2$, commonly referred to as EDTA, commercially available both as the free acid and as various salts, for example, disodium EDTA, tetrasodium EDTA, dipotassium EDTA, calcium disodium EDTA, etc. In some embodiments, the chelator is the naturally occurring amino acid L-cysteine, $HSCH_2CH(NH_2)CO_2H$, or its acetylated derivative N-acetyl-L-cysteine, $HSCH_2CH(NHCOCH_3)CO_2H$, commonly referred to as NAC, or a combination thereof.

The oligomer, such as LNA oligomer, may be formulated into a composition for delayed release of the oligomer. Delayed release formulations for oligonucleotides are known in the art—for example see U.S. Pat. No. 7,576,067. In some embodiments, the oral formulation is not a delayed release formulation—indeed one of the advantages of LNA oligomers is that they are remarkably stable during transport through the intestinal tract. Therefore in some embodiments, the oral composition comprises a delayed release formulation of the at least one oligomer, such as LNA oligomer.

The oligomer, such as LNA oligomer, may be formulated into a composition made for maintenance of an effective dosage level in a target tissue.

In one embodiment, the initial establishment of an effective dosage level is by other means of administration than oral, such as in non-limiting example by parenteral administration, such as via intra venous injection, sub cutaneous injection, intra muscular injection or by intra arterial injection.

In some embodiments, the oral composition comprises at least one further therapeutic agent, or in some embodiments may be administered in conjunction with the administration of at least one further therapeutic agent. In some embodiments, the oral medicament composition further comprises at least one further therapeutically active compound.

In some embodiments, the medicament composition is for the treatment of hyperlipidemia or associated disorders.

In some embodiments, the composition comprises at least one further therapeutic compound used in the treatment of hyperlipidemia or associated disorders, such as at least one statin compound.

In some embodiments, the medicament composition comprises a further therapeutic compound used in the treatment of Hepatitis C, such as interferon, such as interferon alpha.

In some embodiments, the medicament composition is for the treatment of hepatitis C.

The Oligomer

The oligomer may be an LNA oligomer. The LNA oligomer may, in some embodiments, target a mRNA, or a vial RNA sequence. The LNA oligomer may, in some embodiment be a modulator of a microRNA, such as an inhibitor if a microRNA, such as an antimiR or micromiR.

The oligomer may be a modulator a microRNA, such as an inhibitor if a microRNA, which may, in some embodiments, be an LNA oligomer such as an antimiR or micromiR, or may be based upon an alternative chemistry, such as 2' substituted nucleotide analogues.

LNA Oligomers

LNA oligomers comprise at least one locked nucleic acid (LNA) nucleoside unit. LNA oligonucleotides comprise a covalent bridge between the 2' and 4' position of the ribose.

The LNA oligomer is for in vivo use in a subject, such as an individual mammal, preferably a human—also referred to as a patient. The subject is typically a patient who is suffering from or is likely to suffer from a medical disease or condition. Suitably the LNA oligomer is administered, in a therapeutically effective amount, to the subject for the purpose of treating the medical disease or condition. The LNA oligomer may therefore be a therapeutic oligomer.

The term "oligomer" in the context of the present invention, refers to a molecule formed by covalent linkage of two or more nucleotides (i.e. an oligonucleotide). Herein, a single nucleotide (unit) may also be referred to as a monomer or unit. In some embodiments, the terms "nucleoside", "nucleotide", "unit" and "monomer" are used interchangeably. It will be recognised that when referring to a sequence of nucleotides or monomers, what is referred to is the sequence of bases, such as A, T, G, C or U. An LNA oligomer is a oligomer which comprises of at least one LNA unit, such as at least 2, or at least 3, or at least 4 LNA units, or at least 6 LNA units, or at least 7 LNA units, or at least 8 LNA units. LNA oligomers may, in some embodiments consist of LNA units—i.e. the contiguous nucleotide sequence of the oligomer consists of LNA units. The LNA oligomer may in some embodiments comprise or consist of LNA and optionally, either or both naturally occurring nucleotides and/or other non-LNA non-naturally occurring nucleotides.

In some embodiments, the LNA oligomer may comprise both LNA units and non LNA units, such as naturally occurring nucleotides, such as DNA or RNA or both DNA and RNA. LNA oligomers may also comprise other non-naturally occurring nucleotides (nucleotide analogues), such as those provided for herein—the contiguous nucleotide sequence may consist of nucleotides selected from LNA oligonucleotides and non-LNA nucleotide analogues, such as 2'MOE or 2'Omethoxy nucleotide units. In various embodiments, the non-LNA nucleotide analogues may be 2' modified nucleotides, such as nucleotides which comprise a 2' substituent selected from the group consisting of 2'-F, 2'-OCH$_2$ (2'-OMe) or a 2'-O(CH$_2$)$_2$—OCH$_3$ (2'-O-methoxyethyl or 2'-MOE) substituent group.

The oligomer consists or comprises of a contiguous nucleotide sequence of 7-18 nucleotides, such as 8, 9, 10, 11, 12, 13, 14, 15, 16, 17, or 18 nucleotides in length, such as 7-12 or 10-18 nucleotides, or between 10-16 nucleotides, such as 10, 11, 12, 13, 14, 15 and 16 nucleotides, or 12-16, or 12-14 nucleotides. In some embodiments, the LNA oligomer, or contiguous nucleotide sequence thereof has a maximum length of 11, 12, 13 or 14 nucleotides. Micromir LNA oligomers or tiny LNA oligomers, may be between 7 and 10 nucleotides in length, such as 8 or 9 nucleotides in length. Typically gapmer LNA oligomers are at least 10 nucleotide in length, such as at least 12 nucleotides in length.

In some embodiments, the LNA oligomer may be in the form of a gapmer, a blockmer, a headmer, a tailmer, or a mixmer. In some embodiments, the LNA oligomer is a gapmer oligomer or a 'shortmer' oligomer. In some embodiments the LNA oligomer is a antimir or blockmir, and as such, may, in some embodiments be a mixmer or totalmer. In some embodiment the LNA oligomer is a tiny LNA, such as a micromiR.

In some embodiments, the LNA oligomer or contiguous nucleotide sequence thereof consists of a contiguous sequence of nucleotide analogues, such as affinity enhancing nucleotide analogues—referred to herein as a 'totalmer'.

The LNA oligomer may consist or comprise of a contiguous nucleotide sequence which is fully complementary to a sub-sequence of the target, such as a human mRNA or microRNA target, or, when base paired to the target RNA, in some embodiments comprise only a single mismatch to the sub-sequence of the mRNA target.

The LNA oligomer, may, for example, be in the form of an antisense oligonucleotide, an antimiR, a microRNA blockmir (i.e. an oligo which targets the microRNA recognition site on an mRNA target, such as the anti-seed region), an aptamer, a spiegelmer or a siRNA, such as the sense or antisense strand of the siRNA. In a preferable embodiment, the LNA oligomer is an antisense oligonucleotide which targets (i.e. is complementary or essentially complementary to a sequence present in an mRNA or microRNA.

Therefore, the therapeutic LNA oligomer may, in various embodiments, target either i) target nucleic acids, for example mRNAs (antisense oligomers) or microRNA (antimiRs) or ii) target proteins in the subject (aptamers and spiegelmers).

In various embodiments, the LNA oligomer does not comprise RNA (units). It is preferred that the compound according to the invention is a linear molecule or is synthesised as a linear molecule. Such LNA oligomers are single stranded molecules, and preferably does not comprise short regions of, for example, at least 3, 4 or 5 contiguous nucleotides, which are complementary to equivalent regions within the same oligomer (i.e. duplexes)—in this regards, the oligomer is not in some embodiments (essentially) double stranded. In some embodiments, the oligomer is essentially not double stranded, such as is not a siRNA. In various embodiments, the oligomer of the invention may consist entirely of the contiguous nucleotide region. Thus, the oligomer is not, in some embodiments, substantially self-complementary.

The cytosine residues of the LNA oligomer, such as the nucleotide analogues and/or nucleotides, may be methylated—such as comprise a 5-methyl.

The LNA oligomer may, in some embodiments, have at least one modified internucleoside linkage, as described herein, such as phosphorothioate linkages. In some embodiments, all the internucleoside linkages may be phosphorothioate internucleoside linkages.

In some embodiments, the LNA oligomer targets ApoB-100 or PSCK9 or microRNA-122. In some embodiments, the medicament composition is for the use in treatment of hyperlipidemia or an associated disorder. In some embodiments, the LNA oligomer targets microRNA-122. In some embodiments, the LNA oligomer targets a microRNA and the LNA oligomer is a antimiR or a micromiR which targets said microRNA.

Antisense Oligomers

In some embodiments, the LNA oligomer is an LNA antisense oligomer (also referred to as an LNA antisense oligonucleotide) of between 7 and 18 nucleotides in length. In addition to the LNA units, if other nucleotides are present, they may nucleotides may be selected from naturally occurring nucleotides, such as DNA or RNA, as well as non-naturally occurring nucleotides, i.e. nucleotide analogues. In some embodiments, the nucleotides are selected from LNA and DNA units.

The antisense oligomer is preferably perfectly complementary or essentially complementary (such as comprises no more than a single mismatch) to a target nucleic acid naturally present in the subject, such as a target RNA or subsequence thereof, such as an mRNA or microRNA sequence.

In some embodiments the antisense oligomer is in the form of a gapmer, a headmer or a tailmer. Gapmer designs are typically used to target mRNA targets. However, it is also recognised that the antisense oligomer may operate via non RNAse(H) mechanisms. The antisense oligomer may, in some embodiments, be in the form of a mixmer or totamer.

RNAse H Recruitment

In some embodiments, an oligomer functions via non-RNase-mediated degradation of a target mRNA, such as by steric hindrance of translation, or other mechanisms; however, in various embodiments, oligomers of the invention are capable of recruiting an endo-ribonuclease (RNase), such as RNase H.

Typically, the oligomer, comprises a region of at least 6, such as at least 7 contiguous monomers, such as at least 8 or at least 9 contiguous monomers, including 7, 8, 9, 10, 11, 12, 13, 14, 15 or 16 contiguous monomers, which, when forming a duplex with the target region of the target RNA, is capable of recruiting RNase. The region of the oligomer which is capable of recruiting RNAse may be region B, as referred to in the context of a gapmer as described herein. In some embodiments, the region of the oligomer which is capable of recruiting RNAse, such as region B, consists of 8, 9, 10, 11, or 12 nucleotides.

EP 1 222 309 provides in vitro methods for determining RNaseH activity, which may be used to determine the ability of the oligomers of the invention to recruit RNaseH. An oligomer is deemed capable of recruiting RNaseH if, when contacted with the complementary region of the RNA target, it has an initial rate, as measured in pmol/l/min, of at least 1%, such as at least 5%, such as at least 10% or more than 20% of the initial rate determined using an oligonucleotide having the same base sequence but containing only DNA monomers, with no 2' substitutions, with phosphorothioate linkage groups between all monomers in the oligonucleotide, using the methodology provided by Examples 91-95 of EP 1 222 309, incorporated herein by reference.

In some embodiments, an oligomer is deemed essentially incapable of recruiting RNaseH if, when contacted with the complementary target region of the RNA target, and RNaseH, the RNaseH initial rate, as measured in pmol/l/min, is less than 1%, such as less than 5%, such as less than 10% or less than 20% of the initial rate determined using an oligonucleotide having the same base sequence, but containing only DNA monomers, with no 2' substitutions, with phosphorothioate linkage groups between all monomers in the oligonucleotide, using the methodology provided by Examples 91-95 of EP 1 222 309.

In other embodiments, an oligomer is deemed capable of recruiting RNaseH if, when contacted with the complementary target region of the RNA target, and RNaseH, the RNaseH initial rate, as measured in pmol/l/min, is at least 20%, such as at least 40%, such as at least 60%, such as at least 80% of the initial rate determined using an oligonucleotide having the same base sequence, but containing only DNA monomers, with no 2' substitutions, with phosphorothioate linkage groups between all monomers in the oligonucleotide, using the methodology provided by Examples 91-95 of EP 1 222 309.

Typically, the region of the oligomer which forms the duplex with the complementary target region of the target RNA and is capable of recruiting RNase contains DNA monomers and LNA monomers and forms a DNA/RNA-like duplex with the target region. The LNA monomers are preferably in the alpha-L configuration, particularly preferred being alpha-L-oxy LNA.

In various embodiments, the oligomer of the invention comprises both nucleosides and nucleoside analogues, and is in the form of a gapmer, a headmer or a mixmer.

Gapmer Design

Gapmer oligomers are a preferred design of oligomer for the targeting of mRNA targets, and as such, in some embodiments, the LNA oligomer is a gapmer oligomer.

A gapmer oligomer is an oligomer which comprises a contiguous stretch of nucleotides which is capable of recruiting an RNAse, such as RNAseH, such as a region of at least 6 or 7 DNA nucleotides, referred to herein in as region B, wherein region B is flanked both 5' and 3' by regions of affinity enhancing 1-6 nucleotide analogues 5' and 3' to the contiguous stretch of nucleotides which is capable of recruiting RNAse—these regions are referred to as regions A and C respectively.

In some embodiments, the nucleotides which are capable of recruiting RNAse are selected from the group consisting of DNA nucleotides, alpha-L-LNA nucleotides, C4' alkylayted DNA. (see PCT/EP2009/050349 hereby incorporated by reference), and UNA nucleotides (see Fluiter et al., Mol. Biosyst., 2009, 10, 1039 hereby incorporated by reference). In some embodiments, region B consists of a contiguous length of at least 6 or 7 DNA nucleotides, or nucleotides selected from the group consisting of DNA and alpha-L-LNA.

Preferably the gapmer comprises a (poly)nucleotide sequence of formula (5' to 3'), A-B-C, or optionally A-B-C-D or D-A-B-C, wherein; region A (5' region) consists or comprises of at least one LNA unit, such as between 1-6 LNA units, and; region B consists or comprises of at least five consecutive nucleotides which are capable of recruiting RNAse (when formed in a duplex with a complementary RNA molecule, such as the mRNA target), such as DNA nucleotides, and; region C (3' region) consists or comprises of at least one LNA unit, such as between 1-6 LNA units, and; region D, when present consists or comprises of 1, 2 or 3 nucleotide units, such as DNA nucleotides.

In various embodiments, region A consists of 1, 2, 3, 4, 5 or 6 LNA units, such as 2-5 2-5 LNA units, such as 3 or 4 3 or 4 LNA units; and/or region C consists of 1, 2, 3, 4, 5 or 6 LNA units, such as 2-5 2-5 LNA units, such as 3 or 4 3 or 4 LNA units.

In various embodiments B consists or comprises of 5, 6, 7, 8, 9, 10, 11 or 12 consecutive nucleotides which are capable of recruiting RNAse, or between 6-10, or between 7-9, such as 8 consecutive nucleotides which are capable of recruiting RNAse. In various embodiments region B consists or comprises at least one DNA nucleotide unit, such as 1-12 DNA units, preferably 4-12 DNA units, more preferably 6-10 DNA units, such as 7-10 DNA units, preferably 8, 9 or 10 DNA units.

In various embodiments region A consist of 3 or 4 LNA, region B consists of 7, 8, 9 or 10 DNA units, and region C consists of 3 or 4 LNA. Such designs include (A-B-C) 3-10-3, 3-10-4, 4-10-3, 3-9-3, 3-9-4, 4-9-3, 3-8-3, 3-8-4, 4-8-3, 3-7-3, 3-7-4, 4-7-3, and may further include region D, which may have one or 2 nucleotide units, such as DNA units.

Further gapmer designs are disclosed in WO2004/046160 and are hereby incorporated by reference. US provisional application, 60/977,409, hereby incorporated by reference, refers to 'shortmer' gapmer oligomers, which, in various embodiments may be the gapmer oligomer according to the present invention.

In various embodiments the oligomer is consisting of a contiguous nucleotide sequence of a total of 10, 11, 12, 13 or 14 nucleotide units, wherein the contiguous nucleotide sequence is of formula (5'-3'), A-B-C, or optionally A-B-C-D or D-A-B-C, wherein; A consists of 1, 2 or 3 such as LNA units; B consists of 7, 8 or 9 contiguous nucleotide units which are capable of recruiting RNAse when formed in a duplex with a complementary RNA molecule (such as a mRNA target); and C consists of 1, 2 or 3 LNA units. When present, D consists of a single DNA unit.

In various embodiments A consists of 1 LNA unit. In various embodiments A consists of 2 LNA units. In various embodiments A consists of 3 LNA units. In various embodiments C consists of 1 LNA unit. In various embodiments C consists of 2 LNA units. In various embodiments C consists of 3 LNA units. In various embodiments B consists of 7 nucleotide units. In various embodiments B consists of 8 nucleotide units. In various embodiments B consists of 9 nucleotide units. In various embodiments B comprises of between 1-9 DNA units, such as 2, 3, 4, 5, 6, 7 or 8 DNA units. In various embodiments B consists of DNA units. In various embodiments B comprises of at least one LNA unit which is in the alpha-L configuration, such as 2, 3, 4, 5, 6, 7, 8 or 9 LNA units in the alpha-L-configuration. In various embodiments B comprises of at least one alpha-L-oxy LNA unit or wherein all the LNA units in the alpha-L-configuration are alpha-L-oxy LNA units. In various embodiments the number of nucleotides present in A-B-C are selected from the group consisting of (nucleotide analogue units—region B—nucleotide analogue units): 1-8-1, 1-8-2, 2-8-1, 2-8-2, 3-8-3, 2-8-3, 3-8-2, 4-8-1, 4-8-2, 1-8-4, 2-8-4, or; 1-9-1, 1-9-2, 2-9-1, 2-9-2, 2-9-3, 3-9-2, 1-9-3, 3-9-1, 4-9-1, 1-9-4, or; 1-10-1, 1-10-2, 2-10-1, 2-10-2, 1-10-3, 3-10-1. In various embodiments the number of nucleotides in A-B-C are selected from the group consisting of: 2-7-1, 1-7-2, 2-7-2, 3-7-3, 2-7-3, 3-7-2, 3-7-4, and 4-7-3. In various embodiments both A and C consists of two LNA units each, and B consists of 8 or 9 nucleotide units, preferably DNA units.

Splice Switching Oligomers

In some embodiments, the LNA oligomer is a splice switching oligomer—i.e. an oligomer which targets the pre-mRNA causing an alternative splicing of the pre-mRNA.

Targets for the splice switching oligomer may include TNF receptor, for example the SSO may be one or more of the TNFR SSOs disclosed in WO2007/058894, WO08051306 A1 and PCT/EP2007/061211, hereby incorporated by reference.

Splice switching oligomers are typically (essentially) not capable of recruiting RNaseH and as such gapmer, tailmer or headmer designs are generally not desirable. However, mixmer and totalmers designs are suitable designs for SSOs.

mRNA Targets

The target of the LNA oligomer (antisense oligomer) may be a RNA of a gene which is associated with a disease or medical disorder—such as a mRNA, the down-regulation of the RNA target providing a therapeutic benefit. For treatment of disease or medical disorders, the LNA oligomer is typically administered in a therapeutically effective amount.

In some embodiments the LNA oligomer targets the ApoB100 mRNA, such as the oligomers disclosed in WO2007/031081 or WO2008/113830 or U.S. 61/186,388, which are hereby all incorporated by reference.

In some embodiments the LNA oligomer targets the PCSK9 mRNA, such as the oligomers disclosed in WO2008/043753, PCT/EP2009/054499 or U.S. 61/227,109, which are all hereby incorporated by reference.

In some embodiments, the LNA oligomer targets the TNFR-alpha mRNA, such as the oligomers disclosed in WO2007/058894 or WO2008/131807 (both disclose SSOs targeting TNFR1 and TNFR2) which are hereby all incorporated by reference. Such LNA oligomers may be used in the treatment of inflammatory disorders, such as arthritis (incl rheumatoid arthritis).

Mixmers

The term 'mixmer' refers to oligomers which comprise both naturally and non-naturally occurring nucleotides, where, as opposed to gapmers, tailmers, headmers and blockmers, there is no contiguous sequence of more than 5 naturally occurring nucleotides, such as DNA units.

The LNA oligomer may be a mixmer—indeed various mixmer designs are highly effective as LNA oligomers, particularly when targeting microRNA (antimiRs), microRNA binding sites on mRNAs (Blockmirs) or as splice switching oligomers (SSOs).

In some embodiments, the mixmer comprises or consists of a contiguous nucleotide sequence of repeating pattern of nucleotide analogue and naturally occurring nucleotides, or one type of nucleotide analogue and a second type of nucleotide analogues. The repeating pattern, may, for instance be every second or every third nucleotide is a nucleotide analogue, such as LNA, and the remaining nucleotides are naturally occurring nucleotides, such as DNA, or are a 2' substituted nucleotide analogue such as 2'MOE of 2' fluoro analogues as referred to herein, or, in some embodiments selected form the groups of nucleotide analogues referred to herein. It is recognised that the repeating pattern of LNA units, may be combined with nucleotide analogues at fixed positions—e.g. at the 5' or 3' termini.

In some embodiments the first nucleotide of the LNA oligomer, counting from the 3' end, is a nucleotide analogue, such as an LNA nucleotide.

In some embodiments, which maybe the same or different, the second nucleotide of the LNA oligomer, counting from the 3' end, is a nucleotide analogue, such as an LNA nucleotide.

In some embodiments, which maybe the same or different, the seventh and/or eighth nucleotide of the LNA oligomer, counting from the 3' end, are LNA nucleotides.

In some embodiments, which maybe the same or different, the ninth and/or the tenth nucleotides of the LNA oligomer oligomer, counting from the 3' end, are LNA nucleotides.

In some embodiments, which maybe the same or different, the 5' terminal of the LNA oligomer is a nucleotide analogue, such as an LNA nucleotide.

The above design features may, in some embodiments be incorporated into the mixmer design, such as antimiR mixmers.

In some embodiments, the mixmer does not comprise a region of more than 4 consecutive DNA nucleotide units or 3 consecutive DNA nucleotide units. In some embodiments, the mixmer does not comprise a region of more than 2 consecutive DNA nucleotide units.

In some embodiments, the mixmer comprises at least a region consisting of at least two consecutive nucleotide analogue units, such as at least two consecutive LNA units.

In some embodiments, the mixmer comprises at least a region consisting of at least three consecutive nucleotide analogue units, such as at least three consecutive LNA units.

In some embodiments, the mixmer of the invention does not comprise a region of more than 7 consecutive nucleotide analogue units, such as LNA units. In some embodiments, the mixmer of the invention does not comprise a region of more than 6 consecutive nucleotide analogue units, such as LNA units. In some embodiments, the mixmer of the invention does not comprise a region of more than 5 consecutive nucleotide analogue units, such as LNA units. In some embodiments, the mixmer of the invention does not comprise a region of more than 4 consecutive nucleotide analogue units, such as LNA units. In some embodiments, the mixmer of the invention does not comprise a region of more than 3 consecutive nucleotide analogue units, such as LNA units. In some embodiments, the mixmer of the invention does not comprise a region of more than 2 consecutive nucleotide analogue units, such as LNA units.

In the mixmer, such as antimiR or second oligomer embodiments, which refer to the modification of nucleotides in positions 3 to 8, counting from the 3' end, the LNA units may be replaced with other nucleotide analogues, such as those referred to herein. "X" may, therefore be selected from the group consisting of 2'-MOE, 2'-O-alkyl-RNA unit, 2'-OMe-RNA unit, 2'-amino-DNA unit, 2'-fluoro-DNA unit, 2'-MOE-RNA unit, LNA unit, PNA unit, HNA unit, INA unit. "x" is preferably DNA or RNA, most preferably DNA.

In some embodiments, the mixmer, such as an antimiR mixmer, is modified in positions 3 to 8—i.e. comprises at least one nucleotide analogue in positions 3 to 8, counting from the 3' end. The design of this sequence may be defined by the number of non-LNA units present or by the number of LNA units present. In some embodiments of the former, at least one, such as one, of the nucleotides in positions three to eight, counting from the 3' end, is a non-LNA unit. In some embodiments, at least two, such as two, of the nucleotides in positions three to eight, counting from the 3' end, are non-LNA units. In some embodiments, at least three, such as three, of the nucleotides in positions three to eight, counting from the 3' end, are non-LNA units. In some embodiments, at least four, such as four, of the nucleotides in positions three to eight, counting from the 3' end, are non-LNA units. In some embodiments, at least five, such as five, of the nucleotides in positions three to eight, counting from the 3' end, are non-LNA units. In some embodiments, all six nucleotides in positions three to eight, counting from the 3' end, are non-LNA units.

Alternatively defined, in some embodiments, the mixmer, such as an antimiR mixmer, according to the invention comprises at least one LNA unit in positions three to eight, counting from the 3' end. some embodiments, the mixmer, such as an antimiR mixmer, comprises one LNA unit in positions three to eight, counting from the 3' end. The substitution pattern for the nucleotides in positions three to eight, counting from the 3' end, may be selected from the group consisting of Xxxxxx, xXxxxx, xxXxxx, xxxXxx, xxxxXx and xxxxxX, wherein "X" denotes an LNA unit and "x" denotes a non-LNA unit.

In some embodiments, the mixmer, such as an antimiR mixmer, comprises at least two LNA units in positions three to eight, counting from the 3' end. In some embodiments thereof, the mixmer comprises two LNA units in positions three to eight, counting from the 3' end. The substitution pattern for the nucleotides in positions three to eight, counting from the 3' end, may be selected from the group consisting of XXxxxx, XxXxxx, XxxXxx, XxxxXx, XxxxxX, xXXxxx, xXxXxx, xXxxXx, xXxxxX, xxXXxx, xxXxXx, xxXxxX, xxxXXx, xxxXxX and xxxxXX, wherein "X" denotes an LNA unit and "x" denotes a non-LNA unit. In an embodiment, the substitution pattern for the nucleotides in positions three to eight, counting from the 3' end, is selected from the group consisting of XxXxxx, XxxXxx, XxxxXx, XxxxxX, xXxXxx, xXxxXx, xXxxxX, xxXxXx, xxXxxX and xxxXxX, wherein "X" denotes an LNA unit and "x" denotes a non-LNA unit. In some embodiments, the substitution pattern for the nucleotides in positions three to eight, counting from the 3' end, is selected from the group consisting of xXxXxx, xXxxXx, xXxxxX, xxXxXx, xxXxxX and xxxXxX, wherein "X" denotes an LNA unit and "x" denotes a non-LNA unit. In some embodiments, the substitution pattern for the nucleotides in positions three to eight, counting from the 3' end, is selected from the group consisting of xXxXxx, xXxxXx and xxXxXx, wherein "X" denotes an LNA unit and "x" denotes a non-LNA unit. In some embodiments, the substitution pattern for the nucleotides in positions three to eight, counting from the 3' end, is xXxXxx, wherein "X" denotes an LNA unit and "x" denotes a non-LNA unit.

In some embodiments, the mixmer, such as an antimiR mixmer, comprises at least three LNA units in positions three to eight, counting from the 3' end. In an embodiment thereof, the mixmer comprises three LNA units in positions three to eight, counting from the 3' end. The substitution pattern for the nucleotides in positions three to eight, counting from the 3' end, may be selected from the group consisting of XXXxxx, xXXXxx, xxXXXx, xxxXXX, XXxXxx, XXxxXx, XXxxxX, xXXxXx, xXXxxX, xxXXxX, XxXXxx, XxxXXx, XxxxXX, xXxXXx, xXxxXX, xxXxXX, XxXxXx, xXxXxX and XxXxxX, wherein "X" denotes an LNA unit and "x" denotes a non-LNA unit. In some embodiments, the substitution pattern for the nucleotides in positions three to eight, counting from the 3' end, is selected from the group consisting of XXXxXx, XXxxXx, XXxxxX, xXXxXx, xXXxxX, xxXXxX, XxXXxx, XxxXXx, XxxxXX, xXxXXx, xXxxXX, xxXxXX, xXxXXx, xXxxXX, xxXxXX, xXxXxX and XxXxxX, wherein "X" denotes an LNA unit and "x" denotes a non-LNA unit. In some embodiments, the substitution pattern for the nucleotides in positions three to eight, counting from the 3' end, is selected from the group consisting of xXXxXx, xXXxxX, xxXXxX, xXxXXx, xXxxXX and xxXxXX, wherein "X" denotes an LNA unit and "x" denotes a non-LNA unit. In some embodiments, the substitution pattern for the nucleotides in positions three to eight, counting from the 3' end, is xXxXxX or XxXxXx, wherein "X" denotes an LNA unit and "x" denotes a non-LNA unit. In some embodiments, the substitution pattern for the nucleotides in positions three to eight, counting from the 3' end, is xXxXxX, wherein "X" denotes an LNA unit and "x" denotes a non-LNA unit.

In some embodiments, the mixmer comprises at least four LNA units in positions three to eight, counting from the 3' end. In some embodiments thereof, the mixmer comprises four LNA units in positions three to eight, counting from the 3' end. The substitution pattern for the nucleotides in positions three to eight, counting from the 3' end, may be selected from the group consisting of xxXXXX, xXxXXX, xXXxXX, xXXXxX, xXXXXx, XxxXXX, XxXxXX, XxXXxX, XxXXXx, XXxxXX, XXxXxX, XXxXXx, XXXxxX, XXXxXx and XXXXxx, wherein "X" denotes an LNA unit and "x" denotes a non-LNA unit.

In some embodiments, the mixmer according to the present invention comprises at least five LNA units in positions three to eight, counting from the 3' end. In some embodiments thereof, the mixmer comprises five LNA units in positions three to eight, counting from the 3' end. The substitution pattern for the nucleotides in positions three to eight, counting from the 3' end, may be selected from the group consisting of xXXXXX, XxXXXX, XXxXXX, XXXxXX, XXXXxX and XXXXXx, wherein "X" denotes an LNA unit and "x" denotes a non-LNA unit.

In some embodiments, said non-LNA unit is another nucleotide analogue unit.

In some mixmer embodiments the substitution pattern for the nucleotides from position 11, counting from the 3' end, to the 5' end may include nucleotide analogue units (such as LNA) or it may not. In some embodiments, the mixmer comprises at least one nucleotide analogue unit (such as LNA), such as one nucleotide analogue unit, from position 11, counting from the 3' end, to the 5' end. In some embodiments, the mixmer comprises at least two nucleotide analogue units, such as LNA units, such as two nucleotide analogue units, from position 11, counting from the 3' end, to the 5' end.

In some embodiments which refer to the modification of nucleotides in the nucleotides from position 11 to the 5' end of the oligomer, the LNA units may be replaced with other nucleotide analogues, such as those referred to herein. "X" may, therefore be selected from the group consisting of 2'-MOE, 2'-O-alkyl-RNA unit, 2'-OMe-RNA unit, 2'-amino-DNA unit, 2'-fluoro-DNA unit, LNA unit, PNA unit, HNA unit, INA unit. "x" is preferably DNA or RNA, most preferably DNA.

In some embodiments, the mixmer has the following substitution pattern, which is repeated from nucleotide eleven, counting from the 3' end, to the 5' end: xXxX or XxXx, wherein "X" denotes an LNA unit and "x" denotes a non-LNA unit. In another embodiment, the mixmer has the following substitution pattern, which is repeated from nucleotide eleven, counting from the 3' end, to the 5' end: XXxXxx, XXxxXx or XxXxxX, wherein "X" denotes an LNA unit and "x" denotes a non-LNA unit. In yet another embodiment, the mixmer has the following substitution pattern, which is repeated from nucleotide eleven, counting from the 3' end, to the 5' end: XXXxXXXx, XXxXxXxX, XXXxxxXX or XXxXxxXX, wherein "X" denotes an LNA unit and "x" denotes a non-LNA unit.

The specific substitution pattern for the nucleotides from position 11, counting from the 3' end, to the 5' end depends on the number of nucleotides in the mixmer. In a preferred embodiment, the mixmer contains 12 nucleotides and the substitution pattern for positions 11 to 12, counting from the 3' end, is selected from the group consisting of xX and Xx, wherein "X" denotes an LNA unit and "x" denotes a non-LNA unit. In some embodiments, the substitution pattern for positions 11 to 12, counting from the 3' end, is xX, wherein "X" denotes an LNA unit and "x" denotes a non-LNA unit.

Alternatively, no LNA units are present in positions 11 to 12, counting from the 3' end, i.e. the substitution pattern is xx.

In some embodiments, the mixmer contains 12 nucleotides and the substitution pattern for positions 10 to 12, counting from the 3' end, is selected from the group consisting of Xxx, xXx, xxX, XXx, XxX, xXX and XXX, wherein "X" denotes an LNA unit and "x" denotes a non-LNA unit. In some embodiments thereof, the substitution pattern for positions 10 to 12, counting from the 3' end, is selected from the group consisting of xXx, xxX and xXX, wherein "X" denotes an LNA unit and "x" denotes a non-LNA unit. In some embodiments, the substitution pattern for positions 10 to 12, counting from the 3' end, is xxX, wherein "X" denotes an LNA unit and "x" denotes a non-LNA unit. Alternatively, no LNA units are present in positions 10 to 12, counting from the 3' end, i.e. the substitution pattern is xxx.

In some embodiments, the mixmer contains an LNA unit at the 5' end. In some embodiments, the mixmer contains an LNA unit at the first two positions, counting from the 5' end. The mixmer may also contain one or more of the structural features which are specified in the context of the antimiR herein—either the context that the mixmer contains a similar pattern and number of nucleotides/nucleotide analogues (e.g. X and x or X and Y). In some embodiments where the contiguous nucleotide sequence of the mixmer (as a second oligomer) is complementary to the contiguous nucleotide sequence of antimiR (the LNA oligomer) or sub-sequence thereof, the corresponding pattern of nucleotide analogues may be such so that one or more, such as 2, 3, 4, 5, 6, 7, 8, 9, 10, 11, 12 of even all the nucleotide analogues present in the second oligomer form hydrogen bonds with complementary nucleotide analogues in the LNA oligomer. As is discussed herein, this is desirable as it results in a very stable duplex between the two oligomers which effectively results in deactivation of the LNA oligomer (and therefore reduction in bioavailability).

As is described herein, the design of the mixmer antidote (second oligomers), is preferably coordinated with the position of nucleotide analogues in the LNA oligomer. In some embodiments the LNA oligomer comprises one or more 2' substituted nucleotide analogues such as a nucleotide analogue selected from the group consisting of, 2'-MOE, 2'-O-alkyl-RNA unit, 2'-OMe-RNA unit, 2'-amino-DNA unit, 2'-fluoro-DNA unit, 2'-MOE-RNA unit—/the second oligomer may therefore comprise a similar 2' substituted nucleotide analogue or, preferably LNA, at the corresponding position in the second oligomer. When the LNA oligomer is a mixmer, the second oligomer may also be a mixmer which has nucleotide analogues (such as LNA) at the corresponding positions to the nucleotide analogues in the LNA oligomer. When the LNA oligomer is a gapmer—the second oligomer may be a mixmer which comprises at least one nucleotide analogue, such as 2 or 3 nucleotide analogues, in a position (or positions) which corresponds to a nucleotide analogue(s) in region A or C of the gapmer.

In some embodiments, the mixmer comprises of a contiguous nucleotide sequence which consists of nucleotides independently selected from X (LNA) and x (non-LNA nucleotide analogues), wherein the pattern of 'X' and 'x' residues is as referred to herein, The non-nucleotide analogues may, for example be independently, or selected from the group consisting of, 2'-MOE, 2' fluoro or 2'OMe. In some embodiments the contiguous nucleobases sequence comprises only LNA (X) and 2'MOE (x) nucleoside units. In some embodiments the contiguous nucleobases sequence comprises only LNA (X) and 2'Fluoro (x) nucleoside units. In some embodiments the contiguous nucleobases sequence comprises only LNA (X) and non-LNA nucleoside analogue units selected from the group consisting of 2'MOE and 2' fluoro (x) nucleoside units. In some embodiments the contiguous nucleobases sequence comprises LNA (X), 2' fluoro and 2'MOE (x) nucleoside units.

Tailmers and Headmers

A headmer is defined by a contiguous stretch of nucleotide analogues at the 5'-end followed by a contiguous stretch of DNA (or modified nucleotides units recognizable and cleavable by the RNase, such as RNAseH) towards the 3'-end (such as at least 6 or at least 7 of such nucleotides), and a tailmer is defined by a contiguous stretch of DNA (or modified monomers recognizable and cleavable by the RNase, such as RNaseH), at the 5'-end (such as at least 6 or at least 7 such nucleotides), followed by a contiguous stretch of nucleotide analogues towards the 3'-end.

Totalmers

A totalmer is a single stranded oligomer which only comprises non-naturally occurring nucleotides.

The LNA oligomer according to the invention may be a totalmer—indeed various totalmer designs are highly effective as LNA oligomers, particularly when targeting microRNA (antimiRs) or as splice switching oligomers (SSOs). The second oligomer may also be a totalmer and indeed, due to their ability to effectively and specifically bind to their target, the use of totalmers as second oligomers are considered to be particularly effective in decreasing the bioavailability of the LNA oligomer.

In some embodiments, the totalmer comprises or consists of at least one XYX or YXY sequence motif, such as a repeated sequence XYX or YXY, wherein X is LNA and Y is an alternative (i.e. non LNA) nucleotide analogue, such as a 2'-OMe RNA unit and 2'-fluoro DNA unit. The above sequence motif may, in some embodiments, be XXY, XYX, YXY or YYX for example.

In some embodiments, the totalmer may comprise or consist of a contiguous nucleotide sequence of between 8 and 16 nucleotides, such as 9, 10, 11, 12, 13, 14, or 15 nucleotides, such as between 8 and 12 nucleotides.

In some embodiments, the totalmer may comprise or consist of a contiguous nucleotide sequence of between 7 and 10 nucleotides, such as 7, 8 or 9 nucleotides.

In some embodiments, the contiguous nucleotide sequence of the totalmer comprises of at least 30%, such as at least 40%, such as at least 50%, such as at least 60%, such as at least 70%, such as at least 80%, such as at least 90%, such as 95%, such as 100% LNA units. The remaining units may be selected from the non-LNA nucleotide analogues referred to herein in, such those selected from the group consisting of 2'-O_alkyl-RNA unit, 2'-OMe-RNA unit, 2'-amino-DNA unit, 2'-fluoro-DNA unit, LNA unit, PNA unit, HNA unit, INA unit, and a 2'MOE RNA unit, or the group 2'-OMe RNA unit and 2'-fluoro DNA unit.

In some embodiments the totalmer consist of only LNA units, such as comprises of a contiguous nucleotide sequence which consists only of LNA units. In some embodiments, the totalmer (as the LNA oligomer) may be targeted against a microRNA (i.e. be antimiRs)—as referred to in U.S. provisional applications 60/979,217 and 61/028,062, and PCT/DK2008/000344, all of which are hereby incorporated by reference.

microRNA Modulating Oligomers.

In some embodiments the anti-microRNA oligomer may have a gapmer structure as herein described. However, as explained in WO2007/112754 and WO2007/112753, other designs, such as mixmers, or totalmers, such as the AntimiR or micromiRdesigns, are preferable The oligomer may, in some embodiments, target a microRNA. MicroRNAs (miRNAs) are an abundant class of short endogenous RNAs that act as post-transcriptional regulators of gene expression by base-pairing with their target mRNAs. The mature miRNAs are processed sequentially from longer hairpin transcripts by the RNAse III ribonucleases Drosha. Mature microRNAs (miRs) typically between 20 and 25 contiguous RNA nucleotides. It is now widely established that several microRNAs are associated with medical conditions and disease, and several companies are developing therapeutics based on oligomers which either mimic microRNAs or specifically hybridse to specific microRNAs associated with disease phenotypes—such oligomers are referred to, herein, as microRNA mimics and anti-microRNA oligomers (such as antimiRs) respectfully, and the oligomer, in some embodiments may be such microRNA modulating oligomers.

In some embodiments, the oligomer may be a microRNA modulating oligomer, such as an anti-microRNA oligomer, a microRNA blockmer oligomer or a microRNA mimic. The microRNA modulating oligomer may be an LNA oligomer, such as an antimiR or micromiR, or may be based upon an alternative chemistry, such as the antagomir or 2' substituted chemistries referred to herein, for example the 2'MOE/2' fluoro anti-microRNA oligomers and designs disclosed in Davis et al., Nucleic Acid Research 2009, Vol 37 (1), hereby incorporated by reference (including the supplementary data).

Krutzfeldt et al., NAR 2007, Vol 35, No 9, and Krutzfeldt et al., and Krutzfeldt et al., Nature, 2005, 438(7068):685-9, both hereby incorporated by reference, report on a class of anti-microRNA oligomers called antagomirs. Antagomirs are fully 2'OMe modified compounds which are complementary to the mature microRNA sequence, and conjugated at the 3' OH with a cholesterol moiety—the cholesterol moiety may be linked via a hydroxyprolinol linkage. The antagomirs may be partially or fully phosphorothioates—the partial phosphorothioates may, for example, have 2 or 3 phosphorothioate linkages between the 3-4 terminal nucleosides at each end.

Esau et al., Cell Metab. 3 (2006) 87-98, hereby incorporated by reference, also reports on anti-microRNA oligomer which are fully 2'MOE modified, which were not conjugated and had a fully phosphorothioate backbone.

AntimiR oligomers

The LNA oligomer may, in some embodiments, be an antimir (including micromirs) which targets (i.e. comprises or consists of a contiguous nucleotide sequence which is fully complementary to (a corresponding region of) one of the microRNAs listed herein or comprises of no more than a single mismatch thereto.

Oligomers which are complementary to a microRNA target comprise of a sequence of at least seven contiguous nucleotides which are complementary to a part of, or the entire microRNA sequence.

Hence, some aspects of the invention relates to the treatment of a disease associated with the expression of microRNAs selected from the group consisting of infectious diseases such as viral diseases such as hepatitis C virus and HIV, fragile X mental retardation, inflammatory diseases, cancer, such as chronic lymphocytic leukemia, breast cancer, lung cancer and colon cancer.

In some embodiments the oligomer, or LNA oligomer, according to the invention, consists or comprises of a contiguous nucleotide sequence which corresponds to or is fully complementary to a microRNA sequence, such as a mature microRNA sequence, such as the human microRNAs published in miRBase (http://microma.sanger.ac.uk/cgi-bin/sequences/mima_summary.pl?org=hsa). In some embodiment the microRNA is a viral microRNA. At the time of writing, in miRBase Release 14, there are 721 human miRNA sequences in miRBase which are all hereby incorporated by reference, including the mature microRNA sequence of each human microRNA. Other human microRNAs which may be targeted by the oligomer, such as the LNA oligomer, include those disclosed in WO2008040355, hereby incorporated by reference. In some embodiments the oligomer, such as the LNA oligomer according to the invention, consists or comprises of a contiguous nucleotide sequence which corresponds to or is fully complementary to a microRNA sequence selected from the group consisting of hsa-miR19b, hsa-miR21, hsa-miR 122, hsa-miR 142 a7b, hsa-miR 155, and hsa-miR 375. In some embodiments the LNA oligomer according to the invention, consists or comprises of a contiguous nucleotide sequence which corresponds to or is fully complementary to a microRNA sequence selected from the group consisting of hsa-miR221 and hsa-miR222. In some embodiments the LNA oligomer according to the invention, consists or comprises of a contiguous nucleotide sequence which corresponds to part of, or is fully complementary to hsa-miR122 (5'-UGGAGUGUGACAAUGGUGUUUG-3'). LNA oligomer 'antimiR' designs and oligomers are disclosed in WO2007/112754, WO2007/112753, PCT/DK2008/000344 and U.S. provisional applications 60/979,217 and 61/028, 062, all of which are hereby incorporated by reference. Specifically we hereby incorporate the table on page 48-49 of WO2007/112754 entitled 'designs for specific microRNAs) and Table 2 of WO2007/112754 pages 94-105. In some embodiments, the LNA oligomer is an antimiR which is a mixmer or a totalmer.

AntimiR oligomers are LNA oligomers which consist or comprise of a contiguous nucleotide sequence which is fully complementary to, or essentially complementary to (i.e. may comprise no more than one or two mismatches), to a microRNA sequence, or a corresponding sub-sequence thereof. In this regards it is considered that the antimiR may be comprise a contiguous nucleotide sequence which is complementary or essentially complementary to the entire mature microRNA, or the antimiR may be comprise a contiguous nucleotide sequence which is complementary or essentially complementary to a sub-sequence of the mature microRNA or pre-microRNA—such a sub-sequence (and therefore the corresponding contiguous nucleotide sequence) is typically at least 7 or at least 8 nucleotides in length, such as between 8 and 25 nucleotides, such as 9, 10, 11, 12, 13, 14, 15, 16, 17, 18, 19, 20, 21, 22, 23, 24 nucleotides in length, such as between 10-17 or 10-16 nucleotides, such as between 12-15 nucleotides.

Numerous designs of anitmiRs have been suggested, and typically antimiRs for therapeutic use, such as the contiguous nucleotide sequence thereof comprise one or more LNA nucleotide analogues units.

WO2007/112754 and WO2007/112753, both hereby incorporated by reference, provide antimiR oligomers and antimiR oligomer designs where the oligomers which are complementary to mature microRNA In some embodiments, a subsequence of the anti-microRNA oligomer, such as AntimiR or micromiR, corresponds to the miRNA seed region. In some embodiments, the first or second 3' nucleobase of the oligomer corresponds to the second 5' nucleotide of the microRNA sequence.

In some embodiments, nucleobase units 1 to 6 (inclusive) of the oligomer as measured from the 3' end the region of the oligomer are complementary to the microRNA seed region sequence.

In some embodiments, nucleobase units 1 to 7 (inclusive) of the oligomer as measured from the 3' end the region of the oligomer are complementary to the microRNA seed region sequence.

In some embodiments, nucleobase units 2 to 7 (inclusive) of the oligomer as measured from the 3' end the region of the oligomer are complementary to the microRNA seed region sequence.

In some embodiments, the antimiR oligomer comprises at least one nucleotide analogue unit, such as at least one LNA unit, in a position which is within the region complementary to the miRNA seed region. The antimiR oligomer may, in some embodiments comprise at between one and 6 or between 1 and 7 nucleotide analogue units, such as between 1 and 6 and 1 and 7 LNA units, in a position which is within the region complementary to the miRNA seed region.

In some embodiments, the antimiR of the invention is 7, 8 or 9 nucleotides long, and comprises a contiguous nucleotide sequence which is complementary to a seed region of a human or viral microRNA, and wherein at least 80%, such as 85%, such as 90%, such as 95%, such as 100% of the nucleotides are LNA.

In some embodiments, the antimiR of the invention is 7, 8 or 9 nucleotides long, and comprises a contiguous nucleotide sequence which is complementary to a seed region of a human or viral microRNA, and wherein at least 80% of the nucleotides are LNA, and wherein at least 80%, such as 85%, such as 90%, such as 95%, such as 100% of the internucleotide bonds are phosphotioate bonds.

In some embodiments, the antimiR comprises one or two LNA units in positions three to eight, counting from the 3' end. This is considered advantageous for the stability of the A-helix formed by the oligo:microRNA duplex, a duplex resembling an RNA:RNA duplex in structure.

The table on pages 48 line 15 to page 51, line 9 of WO2007/112754 provides examples of anti microRNA oligomers (i.e. antimiRs which may be the LNA oligomer) and is hereby specifically incorporated by reference.

TinyLNAs and MicromiRs

In some highly beneficial embodiments of the invention, the LNA oligomer is a micromiR or Tiny LNA. Tiny LNAs are disclosed in WO2009/043353, hereby incorporated by reference—they are an oligomers of a contiguous sequence of 7, 8, 9 or 10 nucleotide units in length, wherein at least 70%, such as at least 80% of the nucleotide units of the oligomer are selected from the group consisting of LNA units and 2' substituted nucleotide analogues. Table 1 (page 90-107) and Table 2 (Example 1) of WO2009/043353 are hereby specifically incorporated by reference and provides both antimiR and micromir LNA oligomers which may be used in the oral composition of the present invention. Table 4 of WO2009/043353 provides some preferred antimir and micromir compounds:

TABLE 4

LNA_antimiR & MicromiR sequences

| microRNA | sequence | SEQ ID NO |
|---|---|---|
| miR-21 | TcAGtCTGaTaAgCT GATAAGCT | 1 |
| miR-155 | TcAcAATtaGCAtTA TAGCATTA | 2 |

TABLE 4-continued

LNA_antimiR & MicromiR sequences

| microRNA | sequence | SEQ ID NO |
|---|---|---|
| miR-122 | CcAttGTcaCaCtCC CACACTCC | 3 |

Capital letters are LNA units, such as beta-D-oxy LNA. Lower case letters are DNA units.
Internucleoside linkages are preferably phosphorothioate. LNA cytosines are all
preferably methylated/5-methyl cytosine.

Tiny LNAs are remarkably effective for use in reducing the effective amount of a microRNA target in a cell or an organism. Tiny LNAs typically have a LNA content, as measured by the proportion of nucleotide units being LNA, of at least 50%, such as at least 60%, such as at least 70%, such as at least 89%, such as at least 90% or all of the nucleotide units of the oligomer are LNA units. Suitably, the contiguous nucleotide sequence of the micromir LNA is complementary (i.e. 100% complementary) to a corresponding nucleotide sequence found in mammalian or viral microRNA. Alternatively stated, the micromir LNA contiguous nucleotide sequence is identical to (i.e. 100% homologous) to the reverse complement of a contiguous nucleotide sequence found in a mammalian or viral microRNA.

In the context of the present invention, it is, in some embodiments, advantageous to have short oligonucleotides of 7, 8, 9, 10 nucleotides, such as 7, 8 or 9 nucleotides, wherein at least 50%, such as 55%, 60%, 65%, 70%, 75%, 80%, 85%, 90%, 95% or such as 100% of the nucleotide units of the oligomer are (preferably high affinity) nucleotide analogues, such as a Locked Nucleic Acid (LNA) nucleotide unit. Such tiny LNAs are found to be surprisingly robust when administered orally and are found to be effectively absorbed in a therapeutically or physiologically active form in the small intestine.

AntimiR Design—The Seed Region and Seedmers

The inventors of WO 2009/043353 have found that carefully designed short single stranded oligonucleotides comprising or consisting of nucleotide analogues, such as high affinity nucleotide analogues such as locked nucleic acid (LNA) units, show significant silencing of microRNAs, resulting in reduced microRNA levels. It was found that tight binding of said oligonucleotides to the so-called seed sequence, typically nucleotides 2 to 8 or 2 to 7, counting from the 5' end, of the target microRNAs was important. Nucleotide 1 of the target microRNAs is a non-pairing base and is most likely hidden in a binding pocket in the Ago 2 protein. In some embodiments, the antimir/micromiR LNA oligomer does not contain a nucleotide at the 3' end corresponding to this non-paired nucleotide 1. In some embodiments, the antimir/micromiR LNA oligomer has at least two LNA units in the 3' end of the oligonucleotides. In some embodiments, the first or second 3' nucleotide of the antimir/micromiR LNA oligomer corresponds to the second 5' nucleotide of the microRNA sequence, and may be a nucleotide analogue, such as LNA. In some embodiments, nucleotide units 1 to 6 (inclusive) of the antimir/micromiR LNA oligomer as measured from the 3' end the region of the antimir/micromiR LNA oligomer are complementary to the microRNA seed region sequence, and may all be nucleotide analogues, such as LNA. In some embodiments, nucleotide units 1 to 7 (inclusive) of the antimir/micromiR LNA oligomer as measured from the 3' end the region of the antimir/micromiR LNA oligomer are complementary to the microRNA seed region sequence, and may all be nucleotide analogues, such as LNA. In some embodiments, nucleotide units 2 to 7 (inclusive) of the antimir/micromiR LNA oligomer as measured from the 3' end the region of the oligomer are complementary to the microRNA seed region sequence, and may all be nucleotide analogues, such as LNA. In some embodiments, the antimir/micromiR LNA oligomer comprises at least one nucleotide analogue unit, such as at least one LNA unit, in a position which is within the region complementary to the miRNA seed region. The antimir/micromiR LNA oligomer may, in some embodiments comprise at between one and 6 or between 1 and 7 nucleotide analogue units, such as between 1 and 6 and 1 and 7 LNA units, in a position which is within the region complementary to the miRNA seed region. In some embodiments, the contiguous nucleotide sequence consists of or comprises a sequence which is complementary (such as 100% complementary) to the seed sequence of said microRNA. In some embodiments, the contiguous nucleotide sequence consists of or comprises a sequence selected from any one of the seedmer sequences listed in table 1 of WO2009/043353—hereby specifically incorporated by reference. In some embodiments, the 3' nucleotide of the antimir/micromiR LNA oligomer (or seedmer) forms the 3' most nucleotide of the contiguous nucleotide sequence, wherein the contiguous nucleotide sequence may, optionally, comprise one or two further nucleotide 5' to the seedmer sequence. In some embodiments, the oligomer does not comprise a nucleotide which corresponds to the first nucleotide present in the microRNA sequence counted from the 5' end. In some embodiments, the antimir/micromiR LNA oligomer according to the invention does not comprise a nucleotide at the 3' end that corresponds to the first 5' end nucleotide of the target microRNA.

MicroRNA Sequences

In some embodiments the antimiR or micromiR contiguous nucleotide sequence is complementary (such as 100% complementary—i.e. perfectly complementary) to a corresponding region of a mammalian, human or viral microRNA (miRNA) sequence, preferably a human or viral miRNA sequence. Alternatively stated, the antimiR or micromiR contiguous nucleotide sequence is identical to (i.e. 100% homologous) to the reverse complement of a contiguous nucleotide sequence found in a mammalian or viral microRNA. The microRNA sequence may suitably be a mature microRNA. In some embodiments the microRNA may be a microRNA precursor. The human microRNA sequence may be selected from SEQ ID No 1-558 as disclosed in WO2008/046911, which are all hereby and specifically incorporated by reference. As described in WO2008/046911, these microRNAs are associated with cancer. The viral microRNA sequence may, in some embodiments, be selected from the group consisting of Herpes simplex virus 1, Kaposi sarcoma-associated herpesvirus, Epstein Barr virus and Human cytomegalovirus.

In some embodiments, the contiguous nucleotide sequence is complementary (such as 100% complementary) to a corresponding region of a miRNA sequence selected from the group of miRNAs listed in table 1 of WO2009/043353. Table 1 of WO2009/043353 provides 7mer, 8mer and 9mer oligomers which target human and viral microRNAs published in miRBase (Release 12.0—http://microrna.sanger.ac.uk/sequences/).

In some embodiments, the oligomers according to the invention may consist of or comprise a contiguous nucleotide sequence which is complementary to a corresponding microRNA sequence selected from the group consisting of miR-1, miR-10b, miR-17-3p, miR-18, miR-19a, miR-19b, miR-20, miR-21, miR-34a, miR-93, miR-106a, miR-106b, miR-122, miR-133, miR-134, miR-138, miR-155, miR-192, miR-194, miR-221, miR-222, miR-375.

Therefore, in some embodiments, the miRNA (i.e target miRNA) is selected from the group consisting of miR-1, miR-10b, miR-17-3p, miR-18, miR-19a, miR-19b, miR-20, miR-21, miR-34a, miR-93, miR-106a, miR-106b, miR-122, miR-133, miR-134, miR-138, miR-155, miR-192, miR-194, miR-221, miR-222, and miR-375.

In some embodiments, the miRNA target is a member of the miR 17-92 cluster, such as miR 17, miR106a, miR106b, miR 18, miR19a, miR19b/1, miR19b/2, miR20/93, miR92/1, miR92/2 and miR25.

In some embodiments the contiguous nucleotide sequence is complementary to a corresponding region of a microRNA (miRNA) sequence selected from the group consisting of miR-21, miR-155, miR-221, mir-222, and mir-122.

In some embodiments said miRNA is selected from the group consisting of miR-1, miR-10miR-29, miR-125b, miR-126, miR-133, miR-141, miR-143, miR-200b, miR-206, miR-208, miR-302, miR-372, miR-373, miR-375, and miR-520c/e.

In some embodiments the contiguous nucleotide sequence is complementary to a corresponding region of a microRNA (miRNA) sequence present in the miR 17-92 cluster, such as a microRNA selected from the group consisting of miR-17-5p, miR-20a/b, miR-93, miR-106a/b, miR-18a/b, miR-19a/b, miR-25, miR-92a, miR-363.

In some embodiments, the miRNA (i.e target miRNA) is miR-21, such as hsa-miR-21. In some embodiments, the miRNA (i.e target miRNA) is miR-122, such as hsa-miR-122. In some embodiments, the miRNA (i.e target miRNA) is miR-19b, such as hsa-miR-19b. In some embodiments, the miRNA (i.e target miRNA) is miR-155, such as hsa-miR-155. In some embodiments, the miRNA (i.e target miRNA) is miR-375, such as hsa-miR-375. In some embodiments, the miRNA (i.e target miRNA) is miR-375, such as hsa-miR-106b.

Suitably, the contiguous nucleotide sequence may be complementary to a corresponding region of the microRNA, such as a hsa-miR selected from the group consisting of 19b, 21, 122, 155 and 375.

In a highly preferred embodiment, the microRNA target of the LNA oligomer is microRNA-122, preferably the mature form of hsa-miR122. Santaris Pharma A/S is developing a LNA antimiR, SPC3649 (compound B) which targets miR-122.

The invention provides for a method for the treatment of hepatitis C in a subject who is suffering from HCV infection, said method comprising the oral administration of a therapeutically effective amount of a miR-122 antagonist, such as an anti-microRNA oligomer, such as an LNA oligomer, targeting (i.e. complementary to) microRNA-122, such as SPC3649.

Tumor suppressor gene tropomysin 1 (TPM1) mRNA has been indicated as a target of miR-21. Myotrophin (mtpn) mRNA has been indicated as a target of miR 375.

Complementary to has-miR-122

In some embodiment the oligomer is complementary to miR-122. Oligomers which are complementary to microRNA-122 may be used as anti-microRNA oligomers, particularly for use in the treatment of diseases such as HCV or hyperlipidemia.

Oligomers which are complementary to miR-122 comprise of a sequence of at least seven contiguous nucleotides which are complementary to a part of, or the entire has-miR-122 sequence. In this context a part of is at least 6, such as at least 7 or at least 8 contiguous nucleotides which are 100% complementary to a sequence found within microRNA 122 sequence, such as the mature has-miR-122 sequence.

It is preferred that oligomers which are complementary to miR-122 comprise a contiguous nucleotide sequence which is complementary to the has-miR-122 seed sequence, i.e. comprises the contiguous nucleotide sequence 5'-CACTCC-3'-referred to herein as the seed match region.

In some embodiments, the sequence 5'-CACTCC-3' is positioned at positions 1-6, 2-7 or 3-8 of the oligomer, counting from the 3' end. In some embodiments, the sequence 5'-CACTCCA-3' is positioned at positions 1-7 or 2-8 of the oligomer.

An oligomer which consists of a contiguous nucleotide sequence may further comprise non-nucleotide components, such as a 5' or 3' non nucleotide conjugation group. In some embodiments, the oligomer consists of just the contiguous nucleotide sequence.

Oligomers which are complementary to miR-122 may comprise or consist of a contiguous sequence of 7, 8, 9, 10, 11, 12, 13, 14, 15, 16, 17, 18, 19, 20, 21 or 22 nucleotides which are complementary to a part, or the entire, has-miR-122 sequence.

Complementary oligomers which are complementary to the entire miR-122 are at least 22 nts long—i.e. the length of the has-miR-122 sequence and in some instances may comprise further sequences—flanking sequences—which may be complementary to the regions of the pre-has-miR-122 which flank the mature has-miR-122 sequence. Complementary oligomers which are complementary to the entire mature has-miR-122 may therefore be longer than 22 nts on length, such as 23, 24, 25, 26, 27, 28, 29 or 30 nts in length.

Oligomers which are complementary to only a part of the has-miR-122 sequence may be less than 22 nts long, and may comprise a contiguous nucleotide sequence which consists of the complement of a part of the miR-has-miR122 sequence (i.e. a contiguous nucleotide sequence which is complementary to a corresponding region of has-miR-122). In some embodiments, oligomers which are complementary to only a part of the has-miR-122 sequence may comprise flanking sequences which, for example, which may be complementary to the regions of the pre-has-miR-122 which flank the mature has-miR-122 sequence. Complementary oligomers which are complementary to part of the mature has-miR-122 may therefore be longer than 22 nts on length, such as 23, 24, 25, 26, 27, 28, 29 or 30 nts in length. However, in some embodiments, oligomers which are complementary to part of the has-miR-122 are less than 22 nts in length.

In some embodiments, the oligomer may consist of the contiguous nucleotide sequence.

In some embodiments the oligomers which are complementary to miR-122 consists or comprises the contiguous nucleotide sequence 5'-ACACTCC-3'. In some embodiments the oligomers which are complementary to miR-122 consists or comprises the contiguous nucleotide sequence 5'-CACACTCC-3'. In some embodiments the oligomers which are complementary to miR-122 consists or comprises the contiguous nucleotide sequence 5'-CACACTCC-3'. In some embodiments the oligomers which are complementary to miR-122 consists or comprises the contiguous nucleotide sequence 5'-TCACACTCC-3'. In some embodiments the oligomers which are complementary to miR-122 consists or comprises the contiguous nucleotide sequence 5'-GTCACACTCC-3'. (SEQ ID 4). In some embodiments the oligomers which are complementary to miR-122 consists or comprises the contiguous nucleotide sequence 5'-TGTCACACTCC-3'. (SEQ ID 5). In some embodiments the oligomers which are complementary to miR-122 consists or comprises the contiguous nucleotide sequence 5'-ATTGT-CACACTCC-3'. (SEQ ID 6). In some embodiments the oligomers which are complementary to miR-122 consists or comprises the contiguous nucleotide sequence 5'-CATTGT-CACACTCC-3'. (SEQ ID 7).

In some embodiments the oligomers which are complementary to miR-122 consists or comprises the contiguous nucleotide sequence 5'-CCATTGTCACACTCC-3'. (SEQ ID 8)

In some embodiments the oligomers which are complementary to miR-122 consists or comprises the contiguous nucleotide sequence 5'-ACCATTGTCACACTCC-3'. (SEQ ID 9). In some embodiments the oligomers which are complementary to miR-122 consists or comprises the contiguous nucleotide sequence 5'-CACCATTGTCACACTCC-3'. (SEQ ID 10). In some embodiments the oligomers which are complementary to miR-122 consists or comprises the contiguous nucleotide sequence 5'-ACACCATTGTCA-CACTCC-3'. (SEQ ID 11). In some embodiments the oligomers which are complementary to miR-122 consists or comprises the contiguous nucleotide sequence 5'-AACAC-CATTGTCACACTCC-3'. (SEQ ID 12)

In some embodiments the oligomers which are complementary to miR-122 consists or comprises the contiguous nucleotide sequence 5'-AAACACCATTGTCACACTCC-3'. (SEQ ID 13). In some embodiments the oligomers which are complementary to miR-122 consists or comprises the contiguous nucleotide sequence 5'-CAAACACCATTGTCA-CACTCC-3'. (SEQ ID 14). In the above list of embodiments, the 3' cytosine nucleotide may, in some embodiments, be the 3' terminal nucleotide. In some embodiments, there may be a single further nucleoside, such as an adenosine nucleotide 3' to the 3' cytosine in the above sequences. In some embodiments the oligomers which are complementary to miR-122 consists or comprises the contiguous nucleotide sequence 5'-(C)(A)(A)(A)(C)(A)(C)(C)(A)(T)(T)(G)(T)(C) ACACTCC-3', wherein the nucleotides in brackets are optional. In some embodiments the oligomers which are complementary to miR-122 consists or comprises the contiguous nucleotide sequence 5'-(C)(A)(A)(A)(C)(A)(C)(C) (A)(T)(T)(G)(T)(C)ACACTCCA-3', wherein the nucleotides in brackets are optional. Whilst it is preferable that the oligomers which are complementary to miR-122 comprise of the seed match region, it is envisaged that in some embodiments, the seed match region may be truncated by no more than 2 nucleotides from the 3' end. In some embodiments the oligomers which are complementary to miR-122 consists or comprises the contiguous nucleotide sequence 5'-(C)(A)(A) (A)(C)(A)(C)(C)(A)(T)(T)(G)(T)CACACTC-3', wherein the nucleotides in brackets are optional. In some embodiments the oligomers which are complementary to miR-122 consists or comprises the contiguous nucleotide sequence 5'-(C)(A)(A)(A)(C)(A)(C)(C)(A)(T)(T)(G)TCACACT-3', wherein the nucleotides in brackets are optional. In some embodiments the oligomers which are complementary to miR-122 consists or comprises the contiguous nucleotide sequence 5'-CACACTC-3'. In some embodiments the oligomers which are complementary to miR-122 consists or comprises the contiguous nucleotide sequence 5'-TCACACT-3'. In some embodiments the oligomers which are complementary to miR-122 consists or comprises the contiguous nucleotide sequence 5'-TCACACTC-3'. In some embodiments the oligomers which are complementary to miR-122 consists or comprises the contiguous nucleotide sequence 5'-TCA-CACT-3'. In some embodiments the oligomers which are complementary to miR-122 consists or comprises the contiguous nucleotide sequence 5'-GTCACACTC-3'.

In some embodiments the oligomers which are complementary to miR-122 consists or comprises the contiguous nucleotide sequence 5'-GTCACACT-3'.

In some embodiments the oligomers which are complementary to miR-122 consists or comprises the contiguous nucleotide sequence 5'-TGTCACACTC-3'. (SEQ ID 15)

In some embodiments the oligomers which are complementary to miR-122 consists or comprises the contiguous nucleotide sequence 5'-TGTCACACT-3'.

In some embodiments the oligomers which are complementary to miR-122 consists or comprises the contiguous nucleotide sequence 5'-ATTGTCACACTC-3'. (SEQ ID 16)

In some embodiments the oligomers which are complementary to miR-122 consists or comprises the contiguous nucleotide sequence 5'-ATTGTCACACT-3'. (SEQ ID 17)

In some embodiments the oligomers which are complementary to miR-122 consists or comprises the contiguous nucleotide sequence 5'-CATTGTCACACTC-3'. (SEQ ID 18)

In some embodiments the oligomers which are complementary to miR-122 consists or comprises the contiguous nucleotide sequence 5'-CATTGTCACACT-3'. (SEQ ID 19)

In some embodiments the oligomers which are complementary to miR-122 consists or comprises the contiguous nucleotide sequence 5'-CCATTGTCACACTC-3'. (SEQ ID 20)

In some embodiments the oligomers which are complementary to miR-122 consists or comprises the contiguous nucleotide sequence 5'-CCATTGTCACACT-3'. (SEQ ID 21)

In some embodiments the oligomers which are complementary to miR-122 consists or comprises the contiguous nucleotide sequence 5'-ACCATTGTCACACTC-3'. (SEQ ID 22). In some embodiments the oligomers which are complementary to miR-122 consists or comprises the contiguous nucleotide sequence 5'-ACCATTGTCACACT-3'. (SEQ ID 23)

In some embodiments the oligomers which are complementary to miR-122 consists or comprises the contiguous nucleotide sequence 5'-CACCATTGTCACACTC-3'. (SEQ ID 24). In some embodiments the oligomers which are complementary to miR-122 consists or comprises the contiguous nucleotide sequence 5'-CACCATTGTCACACT-3'. (SEQ ID 25). In some embodiments the oligomers which are complementary to miR-122 consists or comprises the contiguous nucleotide sequence 5'-ACACCATTGTCACACTC-3'. (SEQ ID 26). In some embodiments the oligomers which are complementary to miR-122 consists or comprises the contiguous nucleotide sequence 5'-ACACCATTGTCACACT-3'. (SEQ ID 27). In some embodiments the oligomers which are complementary to miR-122 consists or comprises the contiguous nucleotide sequence 5'-AACACCATTGTCACACTC-3'. (SEQ ID 28). In some embodiments the oligomers which are complementary to miR-122 consists or comprises the contiguous nucleotide sequence 5'-AACACCATTGTCACACT-3'. (SEQ ID 29). In some embodiments the oligomers which are complementary to miR-122 consists or comprises the contiguous nucleotide sequence 5'-AAACACCATTGTCACACTC-3'. (SEQ ID 30). In some embodiments the oligomers which are complementary to miR-122 consists or comprises the contiguous nucleotide sequence 5'-AAACACCATTGTCACACT-3'. (SEQ ID 31). In some embodiments the oligomers which are complementary to miR-122 consists or comprises the contiguous nucleotide sequence 5'-CAAACACCATTGTCACACTC-3'. (SEQ ID 32). In some embodiments the oligomers which are complementary to miR-122 consists or comprises the contiguous nucleotide sequence 5'-CAAACACCATTGTCACACT-3'. (SEQ ID 33). In some embodiments the oligomers which are complementary to miR-122 consists or comprises the contiguous nucleotide sequence 5'-CAAACACCATTGTCACACTCCA-3'. (SEQ ID 34)

It should be understood that for RNA nucleotides (e.g. with 2'MOE-RNA units), the T residues can be substituted by U residues, and cytosines may be 5-methyl cytosine.

2' Substituted Anti-microRNA Oligomers

In some embodiments the oligomer may comprise of 2' substituted nucleosides, such as 2'MOE, 2'OMe and/or 2' fluoro:

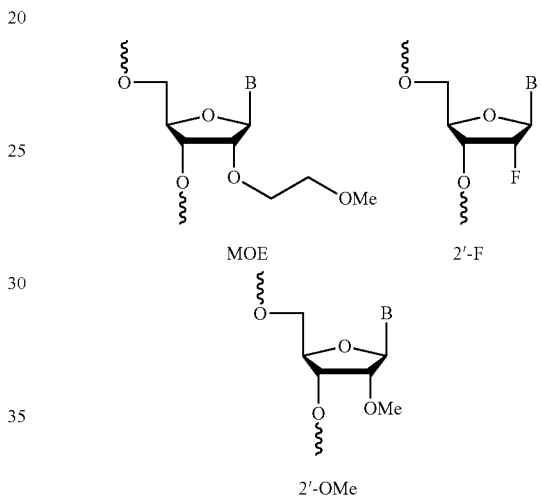

By way of example, Davis et al, NAR 2008 Vol 37, No 1, discloses 2'-fluoro/2'-methoxyethyl (2'MOE) modified ASO motif with dramatically improved in vivo potency. Davis et al., is hereby incorporated by reference.

The 2'MOE/2' fluoro mixmer may, in some embodiments be 12, 13, 14, 15, 17, 17, 18, 19, 20, 21 or 22 nucleotides in length. The following table illustrates how the 2'MOE and 2' fluoro sugar modifications can be incorporated into an oligomer of up to 22 nucleotides in length such as the oligomers whose sequence is provided above:

| 5' | | | | | | | | | | | | | | | | | | | | | 3' |
|---|---|---|---|---|---|---|---|---|---|---|---|---|---|---|---|---|---|---|---|---|---|
| 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| M | M | M | M | M | M | M | M | M | M | M | M | M | M | M | M | M | M | M | M | M | M |
| F | F | F | F | F | F | F | F | F | F | F | F | F | F | F | F | F | F | F | F | F | F |

M represents a 2'-methoxyethyl (2'MOE), F represents a 2' fluoro nucleoside unit. The sequence 1-22 is provided 5'-3': Internucleoside linkages may be as described herein—for example a fully phosphorothioate backbone may be used. The above sequence may, for example be the reverse complement of the mature human has-miR-122 sequence, or part thereof (see above list of anti-miR-122 oligonucleotide sequences). The oligonucleotide may, optionally be conjugated, e.g. by a 3' cholesterol conjugate. Cytosines may be 5-methyl cytosine. In some embodiments, the 1st nucleotide is a 2'MOE nucleotide. In some embodiments, the 1st nucleotide is a 2' fluoro nucleotide. In some embodiments, the 2nd nucleotide is a 2'MOE nucleotide. In some embodiments, the $2^{nd}$ nucleotide is a 2' fluoro nucleotide. In some embodiments, the 3rd nucleotide is a 2'MOE nucleotide. In some embodiments, the 3rd nucleotide is a 2' fluoro nucleotide. In some embodiments, the $4^{th}$ nucleotide is a 2'MOE nucleotide. In some embodiments, the 4th nucleotide is a 2' fluoro nucleotide. In some embodiments, the 5th nucleotide is a 2'MOE nucleotide. In some embodiments, the 5th nucleotide is a 2' fluoro nucleotide. In some embodiments, the 6th nucleotide is a 2'MOE nucleotide. In some embodiments, the 6th nucleotide is a 2' fluoro nucleotide. In some embodiments, the 7th nucleotide is a 2'MOE nucleotide. In some embodiments, the 7th nucleotide is a 2' fluoro nucleotide. In some embodiments, the 8th nucleotide is a 2'MOE nucleotide. In some embodiments, the 8th nucleotide is a 2' fluoro nucleotide. In some embodiments, the 9th nucleotide is a 2'MOE nucleotide. In some embodiments, the 9th nucleotide is a 2' fluoro nucleotide. In some embodiments, the 10th nucleotide is a 2'MOE nucleotide. In some embodiments, the 10th nucleotide is a 2' fluoro nucleotide. In some embodiments, the 11th nucleotide is a 2'MOE nucleotide. In some embodiments, the 11th nucleotide is a 2' fluoro nucleotide. In some embodiments, the 12th nucleotide is a 2'MOE nucleotide. In some embodiments, the 12th nucleotide is a 2' fluoro nucleotide. In some embodiments, the 13th nucleotide, when present, is a 2'MOE nucleotide. In some embodiments, the 13th nucleotide, when present, is a 2' fluoro nucleotide. In some embodiments, the 14th nucleotide, when present, is a 2'MOE nucleotide. In some embodiments, the 14th nucleotide, when present, is a 2' fluoro nucleotide. In some embodiments, the 15th nucleotide, when present, is a 2'MOE nucleotide. In some embodiments, the 15th nucleotide, when present, is a 2' fluoro nucleotide. In some embodiments, the 16th nucleotide, when present, is a 2'MOE nucleotide. In some embodiments, the 16th nucleotide, when present, is a 2' fluoro nucleotide. In some embodiments, the 17th nucleotide, when present, is a 2'MOE nucleotide. In some embodiments, the 17th nucleotide, when present, is a 2' fluoro nucleotide. In some embodiments, the 18th nucleotide, when present, is a 2'MOE nucleotide. In some embodiments, the 18th, when present, nucleotide is a 2' fluoro nucleotide. In some embodiments, the 19th nucleotide, when present, is a 2'MOE nucleotide. In some embodiments, the 19th nucleotide, when present, is a 2' fluoro nucleotide. In some embodiments, the 20th nucleotide, when present, is a 2'MOE nucleotide. In some embodiments, the $20^{th}$ nucleotide, when present, is a 2' fluoro nucleotide. In some embodiments, the 21st nucleotide, when present, is a 2'MOE nucleotide. In some embodiments, the $21^{st}$ nucleotide, when present, is a 2' fluoro nucleotide. In some embodiments, the 22nd nucleotide, when present, is a 2'MOE nucleotide. In some embodiments, the $22^{nd}$ nucleotide, when present, is a 2' fluoro nucleotide. In some embodiments the oligomer consists of 1 2'MOE/2' fluoro designs based on those disclosed in Davis et al., 2009, such as shortened versions, or version with more or less 2'MOE flanks surrounding the 2'F core regions, such as: MFFFFFFFFFFM, MMFFFFFFFFMM, MMMFFFFFFMMM, MFFFFFFFFFFM, MMFFFFFFFFMM, MMMFFFFFFMMM, MFFFFFFFFFFFM, MMFFFFFFFFFMM, MMMFFFFFFFMMM, MFFFFFFFFFFFFM, MMFFFFFFFFFFMM, MMMFFFFFFFFMMM, MFFFFFFFFFFFFFM, MMFFFFFFFFFFFMM, MFFFFFFFFFFFFFFM, MMFFFFFFFFFFFFMM, MMMFFFFFFFFFMMM, MFFFFFFFFFFFFFM, MMFFFFFFFFFFFFMM, MMMFFFFFFFFFFMMM, MFFFFFFFFFFFFFFM, MMFFFFFFFFFFFFFMM, MMMFFFFFFFFFFMMM, MFFFFFFFFFFFFFFFM, MMFFFFFFFFFFFFFMM, MMMFFFFFFFFFFFMMM, MFFFFFFFFFFFFFFFFM, MMFFFFFFFFFFFFFFMM, MMMFFFFFFFFFFFMMM, MFFFFFFFFFFFFFFFFM, MMFFFFFFFFFFFFFFMM, MMMFFFFFFFFFFFFMMM, MFFFFFFFFFFFFFFFFFM, MMFFFFFFFFFFFFFFFMM, or MMMFFFFFFFFFFFFFMMM.

MicroRNA Mimics

In some embodiments the oligomer is in the form of a miRNA mimic which can be introduced into a cell to repress the expression of one or more mRNA target(s). miRNA mimics are typically fully complementary to the full length miRNA sequence. miRNA mimics are compounds comprising a contiguous nucleotide sequence which are homologous to a corresponding region of one, or more, of the miRNA sequences provided or referenced to herein. The use of miRNA mimics or antimiRs can be used to (optionally) further repress the mRNA targets, or to silence (down-regulate) the miRNA, thereby inhibiting the function of the endogenous miRNA, causing derepression and increased expression of the mRNA target. The invention therefore provides for a method for the derepression of a mRNA target in a subject, said method comprising the step of administering a second oligomer according to the invention, wherein the mRNA target is repressed by the presence of a microRNA mimic (which has been administered prior to the administration of the second oligomer), where in the second oligomer conmprises or consists of a contiguous nucleotide sequence which is complementary to, or essentially complementary to, a contiguous nucleotide sequence of the miRNA mimic or subsequence thereof (i.e. corresponds to said miRNA mimic contiguous nucleotide sequence.

Aptamers

In some embodiments the LNA oligomer may be an aptamer, a spiegelmer. Aptamers (also referred to as Spiegelmers) in the context of the present invention as nucleic acids of between 20 and 50 nucleotides in length, which have been selected on the basis of their conformational structure rather than the sequence of nucleotides—they elicit their therapeutic effect by binding with a target protein directly in vivo and they do not, therefore, comprise of the reverse complement of their target—indeed their target is not a nucleic acid but a protein. Specific aptamers which may be the LNA oligomer include Macugen (OSI Pharmaceuticals) or ARC1779, (Archemix, Cambridge, Mass.). In some embodiments, the LNA oligomer is not an aptamer. In some embodiments the LNA oligomer is not an aptamer or a spiegelmer.

Bioavailability Determination

Enhanced bioavailability of biologically active substances is also achieved via the oral administration of the compositions and methods of the present invention. The term "bioavailability" refers to a measurement of what portion of an administered drug reaches the circulatory system when a non-parenteral mode of administration is used to introduce the drug into an animal. The term is used for drugs whose efficacy is related to the blood concentration achieved, even if the drug's ultimate site of action is intracellular (van Berge-Henegouwen et al., Gastroenterol., 1977, 73, 300).

Traditionally, bioavailability studies determine the degree of intestinal absorption of a drug by measuring the change in peripheral blood levels of the drug after an oral dose—relative to an i.v. administration (DiSanto, Chapter 76 In: Remington's Pharmaceutical Sciences, 18th Ed., Gennaro, ed., Mack Publishing Co., Easton, Pa., 1990, pages 1451-1458). The area under the curve (AUCO) is divided by the area under the curve after an intravenous (i.v.) dose (AUCiv) and the quotient is used to calculate the fraction of drug absorbed.

Therefore, oral bioavailability (Oral BAV) is calculated by reference to intravenous injection (IV) of the oligonucleotide at a suitable dose and determining the concentration of oligonucleotide in plasma samples, typically by use of a hybridisation Elisa using a detection probe and a capture probe. The bioavailability is measured by determining the total bioavailability (exposure)—i.e. by an Area Under the Curve analysis (AUC)—comparing the bioavailability from orally administered to IV administered oligonucleotide ($AUC_{oral}/AUC_{IV}$): Oral bioavailability $(F)=(AUC_0^\infty{}_{oral}/AUC_0^\infty{}_{iv}) \times (dose_{iv}/dose_{oral})$.

A suitable dose may be selected as a dose where oligonucleotide AUC is proportional with respect to dosage—typically for LNA oligonucleotides, IV proportioanlity in mammals is typically found between, for example 0.1-100 mg/kgs, such as 1-10 mg/kg, such as 2-8 mg/kg—suitably a level of 3 or 4 mg/kg of LNA oligomer may be used. Typically, plasma AUCs can be estimated suitably from samples obtained at 0.5, 1, 2, 3, 4, 8, 24 and 48 hours. Urine can be collected over 24-h intervals following administration. If information is required regarding intestinal stability or organ accumulation of an oligonucleotide, selected animals can be humanely euthanized at 1 to 24 h after dose administration.

Bioavailability may be determined in a model species, such as a rodent, including mouse or rat, for example, or in another mammal model species, such as dog or pig, for example, or a primate, such as a monkey. Preferably, the bioavailability may be determined in one or more subjects—such as a population of subjects, such as the participants of a clinical trial. The population of animals/subjects may, for example be at least 2, such as at least 5, or at least 10, such as at least 20.

Due to genetic variability between individuals, it is, in some embodiments, appropriate to determine bioavailability by determining the average bioavailability between individuals participating in the trial. The term average or mean bioavailability may therefore be used in place of bioavailability herein.

In some embodiments the bioavailability is tested by comparing ($AUC_{LJ}/AUC_{IV}$), wherein the $AUC_{LJ}$ is determined by administration of the oligomer directly to the jejunum cavity. In this context the description of oral bioavailability herein applies.

Our data indicates that the presence of food in the digestive tract does not significantly affect oral bioavailability. In some embodiments, oral bioavailability may be determined in fasting subjects (i.e. food does not accompany the oligomer through the digestive tract). In some embodiments, the oligomer is administered with food.

In some embodiments the oral bioavailability of the LNA oligomer in a primate, such as a monkey or a human, preferably average oral bioavailability is at least 5%, such as at least 6%, such as at least 7%, such as at least 8%, such as at least 9%, such as at least 10%, such as at least 11%, such as at least 12%, such as at least 13%, such as at least 14%, such as at least 15%, such as at least 16%, such as at least 17%, such as at least 18%, such as at least 19% such as at least 20%, such as at least 22%.

It has been recognized that the oral bioavailability may differ between individuals and between species (Geary et al., Drug Metabolism and Disposition 2003; 31: 1419-1428. For example in a rodent, such as a rat the oral bioavailability may be 2-4 times higher than a human, and therefore, the average oral bioavailability of the LNA oligomer in a rodent, such as a mouse or rat is at least 10%, such as at least 15%, such as at least 16%, such as at least 18%, such as at least 20%, such as at least 22%, such as at least 24%, such as at least 26%, such as at least 28%, such as at least 30% such as at least 32%, such as at least 34%.

In some embodiments when the oral bioavailability of the LNA oligomer in dog, preferably average oral bioavailability is at least 5%, such as at least 6%, such as at least 7%, such as at least 8%, such as at least 9%, such as at least 10%, such as at least 11%, such as at least 12%, such as at least 13%, such as at least 14%, such as at least 15%, such as at least 16%, such as at least 17%, such as at least 18%, such as at least 19% such as at least 20%, such as at least 22%.

In some embodiments, when the oral bioavailability of the LNA oligomer is determined in a pig, preferably average oral bioavailability is at least 0.5%, such as at least 0.6%, such as at least 0.7%, such as at least 0.8%, such as at least 0.9%, such as at least 1.0%, such as at least 1.1%, such as at least 1.2%, such as at least 1.3%, such as at least 1.4%, such as at least 1.5%, such as at least 1.6%, such as at least 1.7%, such as at least 1.8%, such as at least 1.9% such as at least 2.0%, or at least 3.0%.

LNA oligomers delivered by oral administration, in some embodiments may have a higher proportional accumulation of oligomer in the liver as compared to the same LNA oligomer administered by IV. Therefore, in some embodiments, the oligomer may have enhanced biodistribution to the liver when delivered by oral, as compared to IV administration.

The bioavailability may be measured with co-administration of penetration enhancers, such as sodium caprate (C10). The amount of penetration enhancer may be, for example 25 mg/kg. In some embodiments, no penetration enhancer is used. In some embodiments, the amount of penetration enhancer is less than 50 mg/kg, such as 25 mg/kg or less than 25 mg/kg, such as 10 mg/kg, or less than 10 mg/kg, such as 5 mg/kg, or less than 5 mg/kg.

Penetration Enhancer

Penetration enhancers include, but are not necessarily limited to, members of molecular classes such as surfactants, fatty acids, bile acids, chelating agents, non-chelating non-surfactant molecules, and salts thereof. (Lee et al., Critical Reviews in Therapeutic Drug Carrier Systems, 1991, p. 92).

In some embodiments, the penetration enhancer is selected from the group consisting of a fatty acid, bile acid, chelating agent, anionic, cationic or nonionic surfactant or non-chelating non-surfactant, or pharmaceutically acceptable salt thereof.

Fatty acids and their derivatives which act as penetration enhancers and may be used in compositions of the present invention include C8-C20 saturated or unsaturated, linear, branched or cyclic compounds, for example, oleic acid, lauric acid, capric acid (n-decanoic acid) (C10), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glyceryl 1-monocaprate, 1-dodecylazacycloheptan-2-one, acylcarnitines, acylcholines and mono- and di-glycerides thereof and/or physiologically acceptable salts thereof (i.e., oleate, laurate, caprate, myristate, palmitate, stearate, linoleate, etc.) (Lee et al., Critical Reviews in Therapeutic Drug Carrier Systems, 1991, page 92; Muranishi, Critical Reviews in Therapeutic Drug Carrier Systems, 1990, 7, 1; El-Hariri et al., J. Pharm. Pharmacol., 1992, 44, 651). In some embodiments, the fatty acid is arachidonic acid, oleic acid, lauric acid, capric acid, caprylic acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, a monoglyceride or a pharmaceutically acceptable salt thereof. Fatty acids include those with 8-20 carbon atoms, either saturated or having one or more unsaturated bonds, and salts and glycerides thereof.

A variety of bile acids and salts also function as penetration enhancers to facilitate the uptake and bioavailability of drugs. The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al., eds., McGrawHill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (CDCA, sodium chenodeoxycholate), ursodeoxycholic acid (UDCA), sodium tauro-24, 25-dihydro-fusidate (STDHF) and sodium glycodihydrofusidate (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1; Yamamoto et al., J. Pharm. Exp. Ther., 1992, 263, 25; Yamashita et al., J. Pharm. Sci., 1990, 79, 579).

In some embodiments, the bile acid is cholic acid, dehydrocholic acid, deoxycholic acid, glucholic acid, glycholic acid, glycodeoxycholic acid, taurocholic acid, taurodeoxycholic acid, chenodeoxycholic acid, ursodeoxycholic acid, sodium tauro-24,25-dihydrofusidate, sodium glycodihydrofusidate, or a pharmaceutically acceptable salt thereof. In one aspect of this preferred embodiment, the chelating agent is EDTA, EGTA, citric acid, a salicylate, an N-acyl derivative of collagen, an N-amino acyl derivative of a beta-diketone or a mixture thereof.

It is, in some embodiments, desired to select penetration enhancers which facilitate the uptake of drugs, particularly oligonucleotides, without interfering with the activity of the drug and in a manner such that the same can be introduced into the body of an animal without unacceptable side-effects such as toxicity, irritation or allergic response.

In some embodiments, the amount of penetration enhancer may be, for example (about) 25 mg/kg. In some embodiments, no penetration enhancer is used. In some embodiments, the amount of penetration enhancer is less than 50 mg/kg, such as (about) 25 mg/kg or less than 25 mg/kg, such as (about) 10 mg/kg, or less than 10 mg/kg, such as (about) 5 mg/kg, or less than 5 mg/kg. In some embodiments, the penetration enhancer is sodium caprate (C10).

Water Content

For administration by IV, LNA oligomers are typically formulated in an aqueous saline solution. However, such formulations may be unsuitable for oral administration. In some embodiments, the water content of the oral formulation of the invention is less than (about 90%) w/w, such as less than (about) 75% w/w, such as less than (about) 50% w/w, such as less than (about) 25% w/w, such as less than (about) 10% w/w. In some embodiments, the oral composition comprises sufficient water to ensure the stability of the solif or semi-solid formulation.

In some embodiments, the oligomer or oral formulation thereof is to me taken in a solid formulation in conjunction with water. The solid formulation may, in some embodiments be pre-dissolved or dispersed in a liquid prior to administration—such as in the form of a drink.

The liquid may be water or a saline solution for example. In some embodiments, the solid formulation may be taken in conjunction with a separate drink—for example to aid swallowing and to ensure sufficient dilution of the oral formulation once ingested.

In some embodiments, the oral formulation or unit dose form thereof may be formulated as a liquid, a gel or a powder. Such formulations may, in some embodiments facilitate dilution of the LNA oligomer either prior to administration or once ingested.

In some embodiments, the oligomers are formulated in an aqueous oral formulation prior to administration, such as in the form of a drink. In this regardsm the final concentration of oligmer may be less than 5%, such as less than 1%, such as less than 0.1% (w/w) in the liquid formulation immediately prior to oral administration.

In some embodiments, the oral administration of the oligomer is taken in conjunction with a meal—for example within 30 minutes or with 15 minutes of a meal (before or after) or immediately prior to, during or immediately after a meal, such as within 1 minutes, or within 2 minutes or within 3 minutes or within 4 minutes or within 5 minutes of the meal.

Carriers

Carriers are typically inert molecules that may be included in the compositions of the present invention to interfere with processes that may lead to reduction in the levels of bioavailable drug.

Pharmaceutically acceptable organic or inorganic carrier substances suitable for oral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, mannitol, lactose and other sugars and sugar derivatives, amylose, magnesium stearate, talc, silicic acid, viscous paraffin, colloidal silicon dioxide, hydroxymethylcellulose, polyvinylpyrrolidone and the like. The formulations can be sterilized and, if desired, mixed with auxiliary agents, e.g., lubricants, preservatives, flavorants, stabilizers, wetting agents, emulsifiers, salts for influencing osmotic pressure, buffers, bulking agents, colorings flavorings and/or aromatic substances and the like which do not deleteriously interact with the nucleic acid (s) of the formulation.

In some embodiments, the oral formulation of the invention is a solid formulation. In some embodiments, the oral formulation of the invention is in a solid form—such as a capsule or a pill.

The compositions of the present invention may additionally comprise other adjunct components conventionally found in pharmaceutical compositions, at their art-established usage levels. Thus, the compositions may contain additional, compatible, pharmaceutically-active materials such as, for example, antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, do not unduly interfere with the biological activities of the components of the compositions of the present invention.

In some embodiments, the formulation is a capsule, tablet, compression coated tablet, bilayer tablet, trilayer tablet, sachet, liquid-filled capsule or capsule comprising both liquid and solid components. In some embodiments, bioadhesive carrier particles are utilized. Advantageously, the carrier particles comprise poly-amino acids, polyimines, polyacrylates, polyalkylacrylates, polyoxethanes, polyalkylcyanoacrylates, cationized gelatins, albumins, starches, acrylates, polyethylene glycol, DEAE-derivatized polyimines, pollulans, celluloses, chitosan, poly-L-lysine, polyhistidine, polyornithine, polyspermines, protamine, polyvinylpyridine, polythiodiethylamino-methylene P (TDAE), polyaminostyrene, poly (methylcyanoacrylate), poly (ethylcyanoacrylate), poly (butylcyanoacrylate), poly (isobutylcyanoacrylate), poly (isohexylcyanoacrylate), DEAE-methacrylate, DEAE-ethyhexylacrylate, DEAE-acrylamide, DEAE-albumin, DEAE-dextran, polymethylacrylate, polyhexylacrylate, poly (D, L-lactic acid), poly (DL-lactic-coglycolic acid) (PLGA) or polyethylene glycol (PEG). In some embodiments, the carrier particles are cationic. In some embodiments, the carrier particles comprise a complex of poly-L-lysine and alginate, a complex of protamine and alginate, lysine, dilysine, trilysine, calcium, albumin, glucosamine, arginine, galactosamine, nicotinamide, creatine, lysine-ethyl ester or arginine ethyl ester. Preferably, the delayed release coating or matrix is acetate phthalate, propylene glycol, sorbitan monoleate, cellulose acetate phthalate (CAP), cellulose acetate trimellitate, hydroxypropyl methyl cellulose phthalate (HPMCP), methacrylates, chitosan, guar gum, polyethylene glycol (PEG), hydroxypropylmethylcellulose (HPMC), hydroxypropylethylcellulose, ethylcellulose or hydroxypropylmethylcellulose acetate succinate (HPMC-AS).

Surfactants

In connection with the present invention, surfactants (or-"surface-active agents") are chemical entities which, when dissolved in an aqueous solution, reduce the surface tension of the solution or the interfacial tension between the aqueous solution and another liquid, with the result that absorption of oligonucleotides through the alimentary mucosa and other epithelial membranes is enhanced. In addition to bile acids, fatty acids and their salts, surfactants include, for example, sodium lauryl sulfate, polyoxyethylene-9-lauryl ether and polyoxyethylene-20-cetyl ether (Lee et al., Critical Reviews in Therapeutic Drug Carrier Systems, 1991, page 92); and perfluorochemical emulsions, such as FC-43 (Takahashi et al., J. Pharm. Pharmacol., 1988, 40, 252).

Surfactants include anionic, cationic and non-ionic surfactants such as ethylene and/or propylene oxide derivatives, polyoxyethylene alkyl ethers and esters, polysorbates, poloxamers, sodium alkyl sulfates and polyethylene glycol derivatives In some embodiments, the non-chelating non-surfactant is an unsaturated cyclic urea, 1-alkyl-alkanone, 1-alkenylazacycloalkanone, steroid anti-inflammatory agent or mixtures thereof.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the"head") provides the most useful means for categorizing the different surfactants used in formulations (Rieger, in Pharmaceutical Dosage Forms. Disperse Systems, Vol. 1, Lieberman, Rieger and Banker, Eds., Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic ethers and esters such as ethylene glycol esters, propylene glycol ethers and esters, glyceryl esters, polyglyceryl ethers and esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include qu ernary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

Chelating Agents

Chelating agents, as used in connection with the present invention, can be defined to be compounds that remove metallic ions from solution by forming complexes therewith, with the result that absorption of oligonucleotides through the alimentary and other mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315). Chelating agents of the invention include, but are not limited to, disodium ethylenediaminetetraacetate (EDTA), EGTA, citric acid, salicylates (e.g., sodium salicylate, 5-methoxysalicylate and homovanilate), N-acyl derivatives of collagen and N-amino acyl derivatives of beta-diketones (enamines) (Lee et al., Critical Reviews in Therapeutic Drug Carrier Systems, 1991, page 92; Muranishi, Critical Reviews in Therapeutic Drug Carrier Systems, 1990, 7, 1; Buur et al., J. Control Rel., 1990, 14, 43).

As used herein, non-chelating non-surfactant penetration enhancers may be defined as compounds that demonstrate insignificant activity as chelating agents or as surfactants but that nonetheless enhance absorption of oligonucleotides through the alimentary and other mucosal membranes (Muranishi, Critical Reviews in Therapeutic Drug Carrier Systems, 1990, 7, 1). This class of penetration enhancers includes, but is not limited to, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621).
Uptake Enhancers Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al. PCT Application WO 97/30731), can be used.

The formulations of the invention may further comprise a mucolytic substance which serves to degrade or erode mucin, partially or completely, at the site of the mucosal membrane to be traversed. Mucolytic substances are well known in the formulation art and include Nacetylcysteine, dithiothreitol, pepsin, pilocarpine, guaifenesin, glycerol guaiacolate, terpin hydrate, ammonium chloride, guattenesin, ambroxol, bromhexine, carbocysteine, domiodol, letosteine, mecysteine, mesna, sobrerol, stepronin, tiopronin and tyloxapol.
Enteric Formulations The oral formulation into which the oligonucleotide is incorporated may be, for example, a capsule, tablet, compression coated tabletor bilayer tablet. In some embodiments, these formulations comprise an enteric outer coating which resists degradation in the stomach and dissolves in the intestinal lumen. In a preferred embodiment, the formulation comprises an enteric material effective in protecting the nucleic acid from pH extremes of the stomach, or in releasing the nucleic acid over time to optimize the delivery thereof to a particular mucosal site. Enteric materials for acid-resistant tablets, capsules and caplets are known in the art and typically include acetate phthalate, propylene glycol, sorbitan monoleate, cellulose acetate phthalate (CAP), cellulose acetate trimellitate, hydroxypropyl methyl cellulose phthalate (HP-MCP), methacrylates, chitosan, guar gum, pectin, locust bean gum and polyethylene glycol (PEG). One particularly useful type of methacrylate are the Eudragits™. These are anionic polymers that are water-impermeable at low pH, but become ionized and dissolve at intestinal pH. EUDRAGITS™ L100 and S100 are copolymers of methacrylic acid and methyl methacrylate.

Capsules used for oral delivery may include formulations that are well known in the art.

Enteric materials may be incorporated within the dosage form or may be a coating substantially covering the entire surface of tablets, capsules or caplets. Enteric materials may also be accompanied by plasticizers that impart flexible resiliency to the material for resisting fracturing, for example during tablet curing or aging. Plasticizers are known in the art and typically include diethyl phthalate (DEP), triacetin, dibutyl sebacate (DBS), dibutyl phthalate (DBP) and triethyl citrate (TEC).
Excipients The compositions may also comprise an excipient. Typical pharmaceutical excipients include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB); and wetting agents (e.g., sodium lauryl sulphate, etc.). It is preferable that excipients with significant peroxide impurities are avoided.

It is also contemplated that these pharmaceutical compositions are capable of enhancing absorption of biologically active substances when administered via the rectal, vaginal, nasal or pulmonary routes. It is also contemplated that release of the biologically active substance can be achieved in any part of the gastrointestinal tract.
Delayed Release In some embodiments, the composition of the invention is covered or encapsulated in a simple enteric coating—such as pH controlled polymers listed herein—for example on page 5. In some embodiments the LNA oligomer composition/formulation of the invention are not formulated for delayed release of LNA oligomers.

Although it is not considered a requirement of the present invention that LNA oligomers are formulated in a delayed release formula, in some embodiments, the LNA oligomers are in a delayed release formulation.

There are three main practical mechanisms by which a pharmaceutical formulation can be targeted into the intestine (small intestine or colon) following oral administration: activation by colonic bacterial enzymes or reducing environment created by the microflora, pH-dependent coating and time-dependent coating (coating thickness).

Delayed release coatings, and the properties which influence their dissolution, are well known in the art and are described in, for example, Bauer et al., Coated Pharmaceutical Dosage Forms, Medpharm Scientific Publishers, CRC Press, New York, 1998 and by Watts et al., Drug Devel, Indust. Pharm. 23: 893-913, 1997, the entire contents of which are incorporated herein by reference.

Further, multicompartment hard capsules with controlled release properties as described by Digenis et al., U.S. Pat. No. 5,672,359, and water permeable capsules with a multi-stage drug delivery system as described by Amidon et al., U.S. Pat. No. 5,674,530 may also be used to formulate the compositions of the present invention. Capsules may be filled with powders, granules, beads or other multiparticulates, semi-solids, liquids, tablets, solid compacts, emulsions or any combination of these or similar compositions.
Mucosal Delivery In some embodiments of the invention, one or more LNA oligomers are administered via mucosal delivery. Compositions for mucosal administration include powders or granules, beads, suspensions or solutions in water or non-aqueous media, capsules, sachets, troches, tablets or SECs (soft elastic capsules or"caplets"). Thickeners, flavoring agents, colorants, emulsifiers, dispersing aids, carrier substances or binders may be desirably added to such formulations. A tablet may be made by compression or molding, optionally with one or more accessory ingredients.

Formulations for mucosal administration may include sterile and non-sterile aqueous solutions or suspensions, non-aqueous solutions in common solvents such as alcohols, or solutions or suspensions in liquid or solid oil bases. The solutions may also contain buffers, diluents and other suitable additives. Suspensions may contain substances that increase the viscosity of the suspension including, for example, sodium carboxymethylcellulose, sorbitol and/or dextran. The suspension may also contain stabilizers.
Parenteral Pre-Dose Administration The oral administration of the oligomer, in some embodiments, is used to maintain an effective dose of the oligomer in the subject. The build up of the effective dose may me achieved via oral administration, or via an alternative administration route, such as via one or more parenteral dosages.

In some embodiments, the initial establishment of an effective dosage level is by other means of administration than oral, such as in non-limiting example by parenteral administration, such as via intra venous injection, sub cutaneous injection, intra muscular injection or by intra arterial injection.

In some embodiments, the oral administration is preceded by at least one parenteral administration of the oligomer. The initial parenteral dose may, in some embodiments, be administered at least one day, or at least two days, or at least three days prior to the oral administration, or at least a week prior, such as at least two weeks, such as at least three weeks, such as at least four weeks prior to the oral administration.

Over the course of treatment, the oligomer is typically administered to the subject in an effective dose—which may for example be determined by a dose which is sufficient to down-regulate the target RNA, or activity thereof, to a significant level over the time period between successive administration dosages, such as a level which is a therapeutic benefit to the subject. In some embodiments, the target RNA, or activity thereof is down-regulated by at least 10%, such as at least 20%, at least 30%, at least 40%, at least 50%, at least 60%, at least 70% or at least 80% or at least 90% during the time period between successive administration dosages. The effectiveness of the dosages may in example be measured by observation of a disease parameter indicative of the state of the disease, or may depending on the target tissue, be measurable by observation of various tissue parameters, such as activity of the target RNA or amount of viral genome, or in alternative example on a measurable disease state dependent parameter in plasma. However, in some diseases, in non limiting example such a disease could be a viral disease, such as HCV, after the build up phase, a maintenance dosage could be given for a time period wherein the purpose is to maintain a relatively high activity or concentration of the compound in the target tissue, while e.g. the viral titre is decreased or other disease parameters are improved, after which the interval between each dosing could be increased or the dosage given at each dosing could be decreased or both, in order to maintain the disease at the new low level using the minimal needed effective dosage and at the same time obtain minimum side effects and the least inconvenience for the patient by having a high time interval in between administrations.

In some embodiments, after the build up phase, the maintenance dosage will be orally administered wherein the purpose is to maintain an effective concentration in the target tissue, in order to obtain the desired effect on important disease parameters.

In some embodiments a concentration of the oligomer in circulation in the subject, such as in the blood plasma, is maintained at a level of between 0.04 and 25 nM, such as between 0.8 and 20 nM.

In some embodiments, the parenteral (pre-dosage) administration of the compound administered at each dosing, such as unit dose, is within the range of 0.01 mg/kg-25 mg/kg. In some embodiments, each pre-dosage, of the compound administered at each dosing is within the range of 0.05 mg/kg-20 mg/kg. In some embodiments, the each pre-dosage of the compound administered at each dosing is within the range of 0.1 mg/kg-15 mg/kg. In some embodiments, the each pre-dosage of compound administered at each dosing is within the range of 1 mg/kg-15 mg/kg. In some embodiments, the each pre-dosage compound administered at each dosing is within the range of 1 mg/kg-10 mg/kg. In some embodiments, each pre-dosage of the compound administered at each dosing is within the range of 0.01 mg/kg-25 mg/kg, such as about 0.01, 0.05, 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10, 10.25, 10.5, 10.75, 11, 11.25, 11.5, 11.75, 12, 12.25, 12.5, 12.75, 13, 13.25, 13.5, 13.75, 14, 14.25, 14.5, 14.75, 15, 16, 17, 18, 19, 20, 21, 22, 23, 24 or such as about 25 mg/kg, each of which are individual embodiments. In some embodiments, the each predosage compound administered at each dosing is within the range of 25 mg/kg-75 mg/kg.

Therapeutic Application

The compositions and methods of the invention may be useful therapeutically, i.e., to provide therapeutic, palliative or prophylactic relief to an animal, including a human, having or suspected of having or of being susceptible to, a disease or disorder that is treatable in whole or in part with one or more LNA oligomers. The term "disease or disorder" (1) includes any abnormal condition of an organism or part, especially as a consequence of infection, inherent weakness, environmental stress, that impairs normal physiological functioning; (2) excludes pregnancy per se but not autoimmune and other diseases associated with pregnancy; and (3) includes cancers and tumors. The term "having or suspected of having or of being susceptible to" indicates that the subject animal has been determined to be, or is suspected of being, increased risk, relative to the general population of such animals, of developing a particular disease or disorder as herein defined.

For example, a subject animal could have a personal and/or family medical history that includes frequent occurrences of a particular disease or disorder. As another example, a subject animal could have had such a susceptibility determined by genetic screening according to techniques known in the art (see, e.g., U.S. Congress, Office of Technology Assessment, Chapter 5In: Genetic Monitoring and Screening in the Workplace, OTA-BA-455, U.S. Government Printing Office, Washington, D.C., 1990, pages 75-99). The term "a disease or disorder that is treatable in whole or in part with one or more LNA oligomers "refers to a disease or disorder, as herein defined, (1) the management, modulation or treatment thereof, and/or (2) therapeutic, palliative and/or prophylactic relief therefrom, can be provided via the administration of more nucleic acids. In a preferred embodiment, such a disease or disorder is treatable in whole or in part with an antisense oligonucleotide.

In general, for therapeutic applications, a patient (i.e, an animal, including a human) having or predisposed to a disease or disorder is administered one or more drugs, preferably nucleic acids, including oligonucleotides, in accordance with the invention in a pharmaceutically acceptable carrier in doses ranging from (about) 0.01 ug to (about) 1 gm; such as (about) 1 mg to (about) 100 mg per kg of body weight depending on the age of the patient and the severity of the disorder or disease state being treated. In the context of the invention, the term "treatment regimen" is meant to encompass therapeutic, palliative and prophylactic modalities. Following treatment, the patient is monitored for changes in his/her condition and for alleviation of the symptoms of the disorder or disease state The dosage of the drug may either be increased if the patient does not respond significantly to current dosage levels, or the dose may be decreased if an alleviation of the symptoms of the disorder or disease state is observed, or if the disorder or diasase state has been abated.

The term "therapeutically effective amount, "for the purposes of the invention, refers to the amount of LNA oligomer formulation that is effective to achieve an intended purpose without undesirable side effects (such as toxicity, irritation or allergic response). Although individual needs may vary, optimal ranges for effective amounts of formulations can be readily determined by one of ordinary skill in the art. Human doses can be extrapolated from animal studies (Katocs et al., Chapter 27 In. Remington's Pharmaceutical Sciences, 18th Ed., Gennaro, ed., Mack Publishing Co., Easton, Pa., 1990). Generally, the dosage required to provide an effective amount of a formulation, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect (s) (Nies et al., Chapter 3 In: Goodman & Gilman's The Pharmacological Basis of Therapeutics, 9th Ed., Hardman et al., eds., McGraw-Hill, New York, N.Y., 1996).

In some embodiments, the disease or disorder is hyperlipidemia or a related disorder. By way of example, in such embodiments, the LNA oligomer may be an oligomer which targets ApoB-100 or PSCK9 or microRNA-122.

In some aspects, the invention provides for the use of an oral composition according to the invention for the manufacture of a medicament for the treatment of a disease selected from the group consisting of: atherosclerosis, hypercholesterolemia and hyperlipidemia; cancer, glioblastoma, breast cancer, lymphoma, lung cancer; diabetes, metabolic disorders; myoblast differentiation; immune disorders.

The invention provides for a method of treating a subject suffering from a disease or condition selected from the group consisting of: atherosclerosis, hypercholesterolemia and hyperlipidemia; cancer, glioblastoma, breast cancer, lymphoma, lung cancer; diabetes, metabolic disorders; myoblast differentiation; immune disorders, the method comprising the step of administering In some aspects, the invention provides for the use of a oral composition of the invention to the subject in need thereof.

Cancer

In some aspects, the present invention relates to the use of an oral composition according to the invention for the manufacture of a medicament for the treatment of cancer. In another aspect, the present invention concerns a method for treatment of, or prophylaxis against, cancer, said method comprising administering an oral composition of the invention or a pharmaceutical composition of the invention to a patient in need thereof. In non-limiting example, such a treatment may comprise an anti microRNA-21 oligonucleotide.

Alternatively stated, the invention is furthermore directed to a method for treating cancer, said method comprising administering a oral composition of the invention or a pharmaceutical composition according to the invention to a patient in need thereof and further comprising the administration of a further chemotherapeutic agent. Said further administration may be such that the further chemotherapeutic agent is conjugated to the compound of the invention, is present in the pharmaceutical composition, or is administered in a separate formulation.

Infectious Diseases

It is contemplated that, depending on the target of the LNA oligomer, the oral compositions of the invention may be applicable to a broad range of infectious diseases, such as diphtheria, tetanus, pertussis, polio, hepatitis B, hepatitis C, *hemophilus influenza*, measles, mumps, and rubella.

Hsa-miR122 is indicated in hepatitis C infection and as such oligonucleotides according to the invention which target miR-122 may be used to treat Hepatitis C infection.

Accordingly, in yet another aspect the present invention relates the use of an oral composition according to the invention for the manufacture of a medicament for the treatment of an infectious disease, as well as to a method for treating an infectious disease, said method comprising administering an oligonucleotide according to the invention or a pharmaceutical composition according to the invention to a patient in need thereof. In a preferred embodiment, when the LNA oligomer targets miR-122, the infectious disease is hepatitis C.

Inflammatory Diseases

The inflammatory response is an essential mechanism of defense of the organism against the attack of infectious agents, and it is also implicated in the pathogenesis of many acute and chronic diseases, including autoimmune disorders. In spite of being needed to fight pathogens, the effects of an inflammatory burst can be devastating. It is therefore often necessary to restrict the symptomatology of inflammation with the use of anti-inflammatory drugs. Inflammation is a complex process normally triggered by tissue injury that includes activation of a large array of enzymes, the increase in vascular permeability and extravasation of blood fluids, cell migration and release of chemical mediators, all aimed to both destroy and repair the injured tissue.

In some aspects, the present invention relates to the use of an oligonucleotide according to the invention for the manufacture of a medicament for the treatment of an inflammatory disease, as well as to a method for treating an inflammatory disease, said method comprising administering an oligonucleotide according to the invention or a pharmaceutical composition according to the invention to a patient in need thereof.

In some aspects of the invention, the inflammatory disease is a rheumatic disease and/or a connective tissue diseases, such as rheumatoid arthritis, systemic lupus erythematous (SLE) or Lupus, scleroderma, polymyositis, inflammatory bowel disease, dermatomyositis, ulcerative colitis, Crohn's disease, vasculitis, psoriatic arthritis, exfoliative psoriatic dermatitis, pemphigus vulgaris and Sjorgren's syndrome, in particular inflammatory bowel disease and Crohn's disease.

Alternatively, the inflammatory disease may be a non-rheumatic inflammation, like bursitis, synovitis, capsulitis, tendinitis and/or other inflammatory lesions of traumatic and/or sportive origin.

Metabolic Diseases

A metabolic disease is a disorder caused by the accumulation of chemicals produced naturally in the body. These diseases are usually serious, some even life threatening. Others may slow physical development or cause mental retardation. Most infants with these disorders, at first, show no obvious signs of disease. Proper screening at birth can often discover these problems. With early diagnosis and treatment, metabolic diseases can often be managed effectively.

In some embodiments, the present invention relates to the use of an oral composition according to the invention or a conjugate thereof for the manufacture of a medicament for the treatment of a metabolic disease, as well as to a method for treating a metabolic disease, said method comprising administering an oligonucleotide according to the invention or a conjugate thereof, or a pharmaceutical composition according to the invention to a patient in need thereof.

In some embodiments, the metabolic disease is hyperlipidemia or a related disorder.

Liver Disorders

In some embodiments, the present invention relates to the use of an oligonucleotide according to the invention or a conjugate thereof for the manufacture of a medicament for the treatment of a liver disorder, as well as to a method for treating a liver disorder, said method comprising administering an oral composition according to the invention or a conjugate thereof, or a pharmaceutical composition according to the invention to a patient in need thereof. In one preferred embodiment of the invention, the liver disorder is selected from the group consisting of Biliary Atresia, Alagille Syndrome, Alpha-1 Antitrypsin, Tyrosinemia, Neonatal Hepatitis, Hepatitis C virus infection, Hepatitis B virus infection, Hepatitis A virus infection, and Wilson Disease.

Hypercholesterolemia and Related Disorders

Hypercholesterolemia and Related Disorders includes or may be selected from the following medical conditions: different types of HDL/LDL cholesterol imbalance; dyslipidemias, e.g., familial combined hyperlipidemia (FCHL), acquired hyperlipidemia, hypercholesterolemia, statin-resistant hypercholesterolemia; coronary artery disease (CAD), coronary heart disease (CHD), atherosclerosis.

In animal studies LNA oligomers targeting ApoB-100 and PCSK9 have been shown to be effective in treating hypercholesterolemia when administered by IV. LNA oligomers targeting microRNA 122 have been shown to be effective in treating hypercholesterolemia and related disorders. Previously, we have demonstrated that a LNA-antimiR, targeting miR-122a reduces plasma cholesterol levels. Therefore, in some embodiments, the invention is use of an oral composition comprising a LNA oligomer targeting miR-122 as a medicament. In some embodiments of the invention is use of the above described oral composition comprising an LNA oligomer targeting miR-122a for the preparation of a medicament for treatment of increased plasma cholesterol levels (or hypercholesterolemia or a related disorders). Increased plasma cholesterol levels is undesirable as it increases the risk of various conditions, e.g. atherosclerosis.

Still another aspect of the invention is use of the above described oral composition comprising an LNA oligomer targeting miR-122a for upregulating the mRNA levels of Nrdg3, Aldo A, Bckdk or CD320 in a subject.

In some embodiments, the invention provides for an oral composition or combination treatment providing an oral composition comprising an anti miR-122 LNA oligomer in combination with an inhibitor of VLDL assembly, such as an inhibitor of apoB, or of MTP.

In some embodiments the LNA oligomer targets ApoB100. Suitably the contiguous nucleotide sequence of the LNA oligomer which targets ApoB is at least 80% (e.g., 85%, 90%, 95%, 98%, or 99%) homologous to a region corresponding to the reverse complement of a mammalian APO-B100 gene or mRNA, such as the human (genbank accession No: NM_000384 or genbank accession No: NG_011793) or naturally occurring variant thereof. Thus, for example, the oligomer hybridizes, suitably under high stringency, to a single stranded nucleic acid molecule having the sequence of APOB-100 mRNA or APOB-100 gene sequences—or a corresponding region thereof.

The Genbank sequences referred to herein are available in the Genbank release 173.0, and are hereby incorporated by reference.

In some embodiments the LNA oligomer targets PCSK9. Suitably the contiguous nucleotide sequence of the LNA oligomer which targets PCSK9 is at least 80% (e.g., 85%, 90%, 95%, 98%, or 99%) homologous to a region corresponding to the reverse complement of a mammalian PCSK9 gene or mRNA, such as the human (genbank accession No: NM_174936-NARC-1) or naturally occurring variant thereof. Thus, for example, the oligomer hybridizes, suitably under high stringency, to a single stranded nucleic acid molecule having the sequence of PCSK9 sequences—or a corresponding region thereof.

In some embodiments, the invention provides for an LNA oligomer targeting ApoB-100, for use as a medicament, such as for the treatment of diseases associated with apolipoproteinB activity, such as in non-limiting example, different types of HDL/LDL cholesterol imbalance; dyslipidemias, e.g., familial combined hyperlipidemia (FCHL), acquired hyperlipidemia, hypercholesterolemia, statin-resistant hypercholesterolemia; coronary artery disease (CAD), coronary heart disease (CHD), atherosclerosis, wherein the LNA oligomer is for oral administration, such as is in the oral composition according to the invention.

In some embodiments, the invention provides for the use of an LNA oligomer targeting ApoB-100, for the manufacture of a medicament for the treatment of diseases associated with apolipoproteinB activity, such as in non-limiting example, different types of HDL/LDL cholesterol imbalance; dyslipidemias, e.g., familial combined hyperlipidemia (FCHL), acquired hyperlipidemia, hypercholesterolemia, statin-resistant hypercholesterolemia; coronary artery disease (CAD), coronary heart disease (CHD), atherosclerosis, wherein the LNA oligomer is for oral administration, such as is in the oral composition according to the invention.

In some embodiments, the invention provides for a method of treating diseases associated with apolipoproteinB activity, such as in non-limiting example, different types of HDL/LDL cholesterol imbalance; dyslipidemias, e.g., familial combined hyperlipidemia (FCHL), acquired hyperlipidemia, hypercholesterolemia, statin-resistant hypercholesterolemia; coronary artery disease (CAD), coronary heart disease (CHD), atherosclerosis, said method comprising administering an e.g. effective dose of, an LNA oligomer to a patient suffering from, or likely to suffer from diseases associated with apolipoproteinB activity, such as in non-limiting example, different types of HDL/LDL cholesterol imbalance; dyslipidemias, e.g., familial combined hyperlipidemia (FCHL), acquired hyperlipidemia, hypercholesterolemia, statin-resistant hypercholesterolemia; coronary artery disease (CAD), coronary heart disease (CHD), atherosclerosis, wherein the LNA oligomer is for oral administration.

Suitable LNA oligomers targeting ApoB-100 are disclosed in WO2007/031081 or WO2008/113830 or U.S. 61/186,388, which are hereby all incorporated by reference. Preferred LNA oligomers targeting ApoB-100 are illustrated in the examples, such as any one of the compounds with SEQ ID NO's: 28, 29, 44 or 45 and any one of SEQ ID NO's: 3, 4, 19 or 20 as listed in U.S. 61/186,388.

In some embodiments the LNA oligomer targets the PCSK9 mRNA, such as the oligomers disclosed in WO2008/043753, PCT/EP2009/054499 or U.S. 61/227,109, which are all hereby incorporated by reference.

Preferred LNA oligomers targeting PCSK9 mRNA, are those listed in U.S. 61/227,109 with SEQ ID NO's: 1, 2, 3 or 4, as well as compounds comprising the sequence 5'-$G_s^{\circ} T_s^{\circ} c_s t_s g_s g_s g_s a_s a_s G_s^{\circ m}C_s^{\circ} G^{\circ}$-3' (SEQ ID NO 35), where $_s$ are Phosphothioate internucleotide bonds, $^{\circ}$ indicate oxy LNA, such as beta-D-oxy-LNA, and $^m$ indicate 5' methylation (in connection with cytosines), and where Capitals are LNA nucleotides, and Small letters are DNA nucleotides.

MicroRNA—Therapeutic Indications

In some embodiments, the first oligomer is an antimiR, which comprises or consists of a contiguous nucleotide sequence which is corresponds to or is fully complementary to the entire mature microRNA. The use of the present invention in controlling the in vivo activity of microRNA is considered of primary importance due to the fact that microRNAs typically regulate numerous mRNAs in the subject. The ability to inactivate therapeutic antimiRs is therefore very desirable.

The physiological effect of microRNA modulation can be routinely assayed by determining the degree of microRNA target depression (i.e. mRNAs whose expression is modulated by the microRNA)—in the case of microRNA antimirs or micromirs, the affect of microRNA inhibition is alleviation of mRNA repression—i.e. an increase in the microRNA target mRNA level.

Numerous microRNAs are related to a number of diseases. For example:

| microRNA | Possible medical indications |
|---|---|
| miR-1 | Cardiac arythmia |
| miR-21 | Glioblastoma, breast cancer, hepatocellular carcinoma, colorectal cancer, sensitization of gliomas to cytotoxic drugs. |
| miR-21, miR-200b and miR-141 | Response to chemotherapy and regulation of cholangiocarcinoma growth |
| miR-122 | hypercholesterolemia, hepatitis C infection, hemochromatosis |
| miR-19b | lymphoma and other tumour types |
| miR-26a | Osteoblast differentiation of human stem cells |
| miR-155 | lymphoma, pancreatic tumor development, breast and lung cancer |
| miR-203 | Psoriasis |
| miR-375 | diabetes, metabolic disorders, glucose-induced insulin secretion from pancreatic endocrine cells |
| miR-181 | myoblast differentiation, auto immune disorders |
| miR-10b | Breast cancer cell invasion and metastasis |
| miR-125b-1 | Breast, lung, ovarian and cervical cancer |
| miR-221 and 222 | Prostate carcinoma, human thyroid papillary car, human hepatocellular carcinoma |
| miRNA-372 and -373 | testicular germ cell tumors. |
| miR-142 | B-cell leukemia |
| miR-17 - 19b cluster | B-cell lymphomas, lung cancer, hepatocellular carcinoma |

In some embodiments, the disease or disorder is characterized by being sensitive to downregulation of a microRNA, such as, but not limited to a disease selected from the list of cardiac arythmia, cardiac hypertrophy, cancer, hypercholesterolemia, metabolic disorders, psoriasis, diabetes, auto immune disorders, hemochromatosis, or hepatitis C infection.

Dosage Regimens

The dosage of the oral composition is dependent on severity and responsiveness of the disease state to be treated, and the course of treatment lasting from several days to several months, or until a cure is effected or a diminution of the disease state is achieved. Optimal dosing schedules can be calculated from measurements of drug accumulation in the body of the patient. Optimum dosages may vary depending on the relative potency of individual oligonucleotides. Generally it can be estimated based on $EC_{50}$s found to be effective in vitro and in vivo animal models. In general, dosage is from 0.01 µg to 1 g per kg of body weight, and may be given once or more daily, weekly, monthly, for example. The repetition rates for dosing can be estimated based on measured residence times and concentrations of the drug in bodily fluids or tissues. Following successful treatment, it may be desirable to have the patient undergo maintenance therapy to prevent the recurrence of the disease state.

In general, dosage is from 0.01 mg to 10 g per kg of body weight, and may be given once or more daily, (about) weekly, (about) monthly, (about) bimonthly etc. An optimal dosing schedule is used to deliver a therapeutically effective amount of the drug being administered via a particular mode of administration.

The LNA oligomer may, in some embodiments, be administered at regular intervals (Dose intervals, DI), such as twice daily, daily, or a period of between 2 or 3 days and two weeks, such as 4, 5, 6, 7, 8, 9, 10, 11, 12, 13 days, such as about 1 week, such as 6, 7 or 8 days. Suitably at least two doses are provided with a DI period between the two dosages, such as 3, 4, 5, 6, 7, 8, 9 or 10 dosages, each with a dose interval (DI) between each dose of LNA oligomer. The DI period between each dosage may the same, such as between 3 days and two weeks, such as 4, 5, 6, 7, 8, 9, 10, 11, 12, 13 days, such as about 1 week, such as 6, 7 or 8 days.

WO2009/109665 discloses some preferred dosage regimens for LNA oligomers, and is hereby incorporated in its entirety. In some embodiments, such as when the LNA oligomer is an antimir, a mixmer or a micromir or tinyLNA, at least two dosages are administered to the primate with a time interval between each administration of at least (about) two weeks, such as at least (about) three or (about) four weeks. In some embodiments, the administrations are administered with a time interval between each administration of at least 30 days or at least 40 days. In some embodiments, the LNA oligomer is a mixmer or totalmer, or a antimir or micromir—such as the anti-miR-122 oligomer having the sequence: 5'-CcAttGTcaCaCtCC-3' (compound B—SEQ ID NO 36), wherein capitals are LNA, and small letters are DNA.

The number of administrations may be more than 2, such as 3, 4, 5, 6, 7, 8, 9, 10, 11, 12, 13, 14, 15, 16 or more treatments. As described herein, the actual number of administrations will depend on the nature of disease or disorder, for example. Diseases which may be cured will provide a definite end point to the administration regimen, whereas a disease or disorder may be treated over an extended period of time, effectively controlling symptoms, but may, in some embodiments not provide a cure. In such instances routine/regular administration may be continued for several months or years, until treatment is no longer desirable as determined by the medical practitioner. It will be noted that in some embodiments, administration regimens may be interrupted by a treatment pause, such a period of more than 125 days, or in some embodiments, a period of more than 2, 3, 5, or 6 months.

In one embodiment, the oral administration is for maintenance of an already established effective dosage level.

Further Therapeutic Agents

In some embodiments the method of treatment according to the invention further comprises the administration of at least one further therapeutic compound, such as a therapeutic compound for the treatment of hyperlipidemia or a related disorder, such as a statin.

In some embodiments, the LNA oligomer and the further therapeutic agent are within the same oral formulation.

In some embodiments, the LNA oligomer and the further therapeutic agent may be in different pharmaceutical formulations.

In some embodiments, the LNA oligomer and the further therapeutic agent may be administered concurrently—i.e. so that the therapeutic benefit of each agent is achieved simultaneously during the treatment of the disease or disorder. As such, the oral composition of the invention may be administered prior to, concurrent with, or subsequent to the further therapeutic agent. In some embodiments, the at least one further therapeutic compound is administered prior to, concurrent to, or subsequent to, the administration of the LNA oligomer.

In some embodiments, when the medical disease or disorder is a viral infection, such as hepatitis C, the at least one further therapeutic agent may interferon, such as interferon alpha. In such embodiments, the LNA oligomer, may, for example, target miR-122.

Interferon alpha is a major treatment of choice in HCV infected patients. In some embodiments, such as when the LNA oligomer targets hsa-miR-122 the further therapeutic agent is interferon alpha. Such a combination treatment may be used in the treatment of hepatitis C.

The statins (or HMG-CoA reductase inhibitors) are a class of drugs that lower cholesterol levels in people with or at risk of cardiovascular disease. They lower cholesterol by inhibiting the enzyme HMG-CoA reductase, which is the rate-limiting enzyme of the mevalonate pathway of cholesterol synthesis. Inhibition of this enzyme in the liver results in decreased cholesterol synthesis as well as increased synthesis of LDL receptors, resulting in an increased clearance of low-density lipoprotein (LDL) from the bloodstream. Examples of statins may be selected from the group consisting of: Atorvastatin, Cerivastatin, Fluvastatin, Lovastatin, Mevastatin, Pitavastatin, Pravastatin, Rosuvastatin, and Simvastatin.

In some embodiments, such as when the LNA oligomer is targeting ApoB-100, PCSK-9 or miR-122, for example, the further therapeutic agent may be an inhibitor of the VLDL assembly pathway, such as an ApoB inhibitor, or an MTP inhibitor, such as a statin.

In a certain embodiments, the present invention provides pharmaceutical compositions containing (a) one or more antisense compounds and (b) one or more other chemotherapeutic agents which function by a non-antisense mechanism. When used with the compounds of the invention, such chemotherapeutic agents may be used individually (e.g. mithramycin and oligonucleotide), sequentially (e.g. mithramycin and oligonucleotide for a period of time followed by another agent and oligonucleotide), or in combination with one or more other such chemotherapeutic agents or in combination with radiotherapy. All chemotherapeutic agents known to a person skilled in the art are here incorporated as combination treatments with compound according to the invention.

In another embodiment, compositions of the invention may contain one or more antisense compounds, particularly oligonucleotides, targeted to a first nucleic acid and one or more additional antisense compounds targeted to a second nucleic acid target. Two or more combined compounds may be used together or sequentially. i.e. the compound according to the invention may be used prior to, during or subsequent to one or more of the other therapeutic agents referred to herein.

The pharmaceutical composition of the invention may constitute a pro-drug. Therefore, in some embodiments of the invention the compound of the invention may be in the form of a pro-drug. Oligonucleotides are by virtue negatively charged ions. Due to the lipophilic nature of cell membranes the cellular uptake of oligonucleotides are reduced compared to neutral or lipophilic equivalents. This polarity "hindrance" can be avoided by using the pro-drug approach (see e.g. Crooke, R. M. (1998) in Crooke, S. T. Antisense research and Application. Springer-Verlag, Berlin, Germany, vol. 131, pp. 103-140). In this approach the oligonucleotides are prepared in a protected manner so that the oligo is neutral when it is administered. These protection groups are designed in such a way that so they can be removed then the oligo is taken up be the cells. Examples of such protection groups are S-acetylthioethyl (SATE) or S-pivaloylthioethyl (t-butyl-SATE). These protection groups are nuclease resistant and are selectively removed intracellulary.

In some embodiments, the oral composition of the invention further comprises anti-inflamatory compounds and/or antiviral compounds.

The Target

In some embodiments, the oligomer of the invention is capable of down-regulating expression of a target nucleic acid, typically by antagonising a mRNA or a microRNA. In this regards, the oligomer of the invention can effect the inhibition of a therapeutically relevant mRNA or microRNA target, typically in a mammalian such as a human cell. In some embodiments, the oligomers of the invention bind to the target nucleic acid and effect inhibition of expression of at least 10% or 20% compared to the normal expression level, more preferably at least a 30%, 40%, 50%, 60%, 70%, 80%, 90% or 95% inhibition compared to the normal expression level. In some embodiments, such modulation is seen when using between 0.04 and 25 nM, such as between 0.8 and 20 nM concentration of the compound of the invention. In the same or a different embodiment, the inhibition of expression is less than 100%, such as less than 98% inhibition, less than 95% inhibition, less than 90% inhibition, less than 80% inhibition, such as less than 70% inhibition. Modulation of expression level may be determined by measuring protein levels, e.g. by the methods such as SDS-PAGE followed by western blotting using suitable antibodies raised against the target protein. Alternatively, modulation of expression levels can be determined by measuring levels of mRNA, e.g. by northern blotting or quantitative RT-PCR. When measuring via mRNA levels, the level of down-regulation when using an appropriate dosage, such as between 0.04 and 25 nM, such as between 0.8 and 20 nM concentration, is, in some embodiments, typically to a level of between 10-20% the normal levels in the absence of the compound of the invention. As used herein, the phrase "potent inhibitor" refers to an oligomer with an 1050 of less than 5 nM as determined by the lipofectamin transfection assay. In some embodiments, the 1050 is less than 4 nM, such as less than 2 nM.

In some embodiments, the invention therefore provides a method of down-regulating or inhibiting the expression of a target nucleic acid in a subject which is expressing said target nucleic acid, said method comprising administering an effective amount of the oral composition of the invention to said said subject to down-regulate or inhibit the expression of said target nucleic acid in the subject.

The term "naturally occurring variant thereof" refers to variants of the target nucleic acid sequence which exist naturally within the defined taxonomic group, such as mammalian, such as mouse, monkey, and preferably human. Typically, when referring to "naturally occurring variants" of a polynucleotide the term also may encompass any allelic variant of the target nucleic acid. "Naturally occurring variants" may also include variants derived from alternative splicing of the target nucleic acid mRNA. When referenced to a specific polypeptide sequence, e.g., the term also includes naturally occurring forms of the protein which may therefore be processed, e.g. by co- or post-translational modifications, such as signal peptide cleavage, proteolytic cleavage, glycosylation, etc.

In determining the degree of "complementarity" between oligomers of the invention (or regions thereof) and the target region of a nucleic acid the degree of "complementarity" (also, "homology" or "identity") is expressed as the percentage identity (or percentage homology) between the sequence of the oligomer (or region thereof) and the sequence of the target region (or the reverse complement of the target region) that best aligns therewith. The percentage is calculated by counting the number of aligned bases that are identical between the 2 sequences, dividing by the total number of contiguous monomers in the oligomer, and multiplying by 100. In such a comparison, if gaps exist, it is preferable that such gaps are merely mismatches rather than areas where the number of monomers within the gap differs between the oligomer of the invention and the target region.

As used herein, the terms "homologous" and "homology" are interchangeable with the terms "identity" and "identical".

The terms "corresponding to" and "corresponds to" refer to the comparison between the nucleotide sequence of the oligomer (i.e. the nucleobase or base sequence) or contiguous nucleotide sequence (a first region) and the equivalent contiguous nucleotide sequence of a further sequence selected from either i) a sub-sequence of the reverse complement of the nucleic acid target, and/or ii) the sequence of nucleotides provided herein, or sub-sequence thereof. Nucleotide analogues are compared directly to their equivalent or corresponding nucleotides. A first sequence which corresponds to a further sequence under i) or ii) typically is identical to that sequence over the length of the first sequence (such as the contiguous nucleotide sequence) or, as described herein may, in some embodiments, is at least 80% homologous to a corresponding sequence, such as at least 85%, at least 90%, at least 91%, at least 92% at least 93%, at least 94%, at least 95%, at least 96% homologous, such as 100% homologous (identical).

The terms "corresponding nucleotide analogue" and "corresponding nucleotide" are intended to indicate that the nucleotide in the nucleotide analogue and the naturally occurring nucleotide are identical. For example, when the 2-deoxyribose unit of the nucleotide is linked to an adenine, the "corresponding nucleotide analogue" contains a pentose unit (different from 2-deoxyribose) linked to an adenine.

The terms "reverse complement", "reverse complementary" and "reverse complementarity" as used herein are interchangeable with the terms "complement", "complementary" and "complementarity".

Nucleosides and Nucleoside Analogues

In some embodiments, the terms "nucleoside analogue" and "nucleotide analogue" are used interchangeably.

The term "nucleotide" as used herein, refers to a glycoside comprising a sugar moiety, a base moiety and a covalently linked group (linkage group), such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogues" herein. Herein, a single nucleotide (unit) may also be referred to as a monomer or nucleic acid unit.

In field of biochemistry, the term "nucleoside" is commonly used to refer to a glycoside comprising a sugar moiety and a base moiety, and may therefore be used when referring to the nucleotide units, which are covalently linked by the internucleotide linkages between the nucleotides of the oligomer. In the field of biotechnology, the term "nucleotide" is often used to refer to a nucleic acid monomer or unit, and as such in the context of an oligonucleotide may refer to the base—such as the "nucleotide sequence", typically refer to the nucleobase sequence (i.e. the presence of the sugar backbone and internucleoside linkages are implicit). Likewise, particularly in the case of oligonucleotides where one or more of the internucleoside linkage groups are modified, the term "nucleotide" may refer to a "nucleoside" for example the term "nucleotide" may be used, even when specifiying the presence or nature of the linkages between the nucleosides.

As one of ordinary skill in the art would recognise, the 5' terminal nucleotide of an oligonucleotide does not comprise a 5' internucleotide linkage group, although may or may not comprise a 5' terminal group.

Non-naturally occurring nucleotides include nucleotides which have modified sugar moieties, such as bicyclic nucleotides or 2' modified nucleotides, such as 2' substituted nucleotides.

"Nucleotide analogues" are variants of natural nucleotides, such as DNA or RNA nucleotides, by virtue of modifications in the sugar and/or base moieties. Analogues could in principle be merely "silent" or "equivalent" to the natural nucleotides in the context of the oligonucleotide, i.e. have no functional effect on the way the oligonucleotide works to inhibit target gene expression. Such "equivalent" analogues may nevertheless be useful if, for example, they are easier or cheaper to manufacture, or are more stable to storage or manufacturing conditions, or represent a tag or label. Preferably, however, the analogues will have a functional effect on the way in which the oligomer works to inhibit expression; for example by producing increased binding affinity to the target and/or increased resistance to intracellular nucleases and/or increased ease of transport into the cell. Specific examples of nucleoside analogues are described by e.g. Freier & Altmann; *Nucl. Acid Res.*, 1997, 25, 4429-4443 and Uhlmann; *Curr. Opinion in Drug Development*, 2000, 3(2), 293-213, and in Scheme 1:

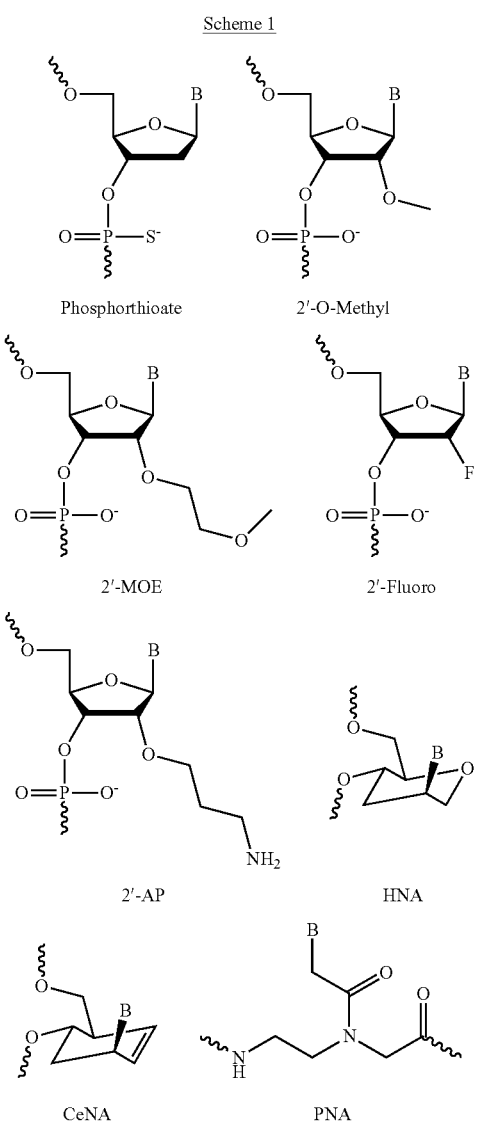

Scheme 1

Phosphorthioate

2'-O-Methyl

2'-MOE

2'-Fluoro

2'-AP

HNA

CeNA

PNA

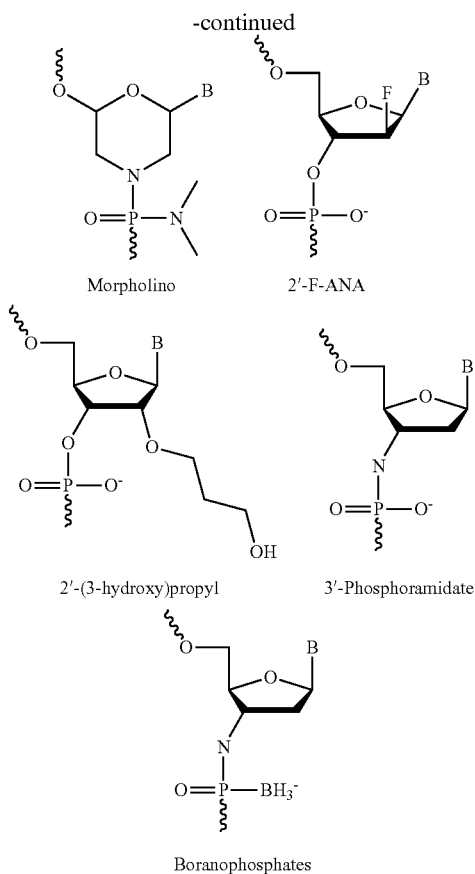

Morpholino 2'-F-ANA

2'-(3-hydroxy)propyl 3'-Phosphoramidate

Boranophosphates

The oligomer may thus comprise or consist of a simple sequence of natural occurring nucleotides—preferably 2'-deoxynucleotides (referred to here generally as "DNA"), but also possibly ribonucleotides (referred to here generally as "RNA"), or a combination of such naturally occurring nucleotides and one or more non-naturally occurring nucleotides, i.e. nucleotide analogues. Such nucleotide analogues may suitably enhance the affinity of the oligomer for the target sequence.

Examples of nucleotide analogues are provided by WO2007/031091 or are referenced therein.

Incorporation of affinity-enhancing nucleotide analogues in the oligomer, such as LNA or 2'-substituted sugars, can allow the size of the specifically binding oligomer to be reduced, and may also reduce the upper limit to the size of the oligomer before non-specific or aberrant binding takes place.

In addition to the at least on LNA unit, in some embodiments, the oligomer comprises at least 1 nucleoside analogue. In some embodiments the oligomer comprises at least 2 nucleotide analogues. In some embodiments, the oligomer comprises from 3-8 nucleotide analogues, e.g. 6 or 7 nucleotide analogues. In the by far most preferred embodiments, at least one of said nucleotide analogues is a locked nucleic acid (LNA); for example at least 3 or at least 4, or at least 5, or at least 6, or at least 7, or 8, of the nucleotide analogues may be LNA. In some embodiments all the nucleotides analogues may be LNA.

It will be recognised that when referring to a preferred nucleotide sequence motif or nucleotide sequence, which consists of only nucleotides, the oligomers of the invention which are defined by that sequence may comprise a corresponding nucleotide analogue in place of one or more of the nucleotides present in said sequence, such as LNA units or other nucleotide analogues, which raise the duplex stability/$T_m$ of the oligomer/target duplex (i.e. affinity enhancing nucleotide analogues).

In some embodiments, any mismatches between the nucleotide sequence of the oligomer and the target sequence are preferably found in regions outside the affinity enhancing nucleotide analogues, such as region B as referred to herein, and/or region D as referred to herein, and/or at the site of non modified such as DNA nucleotides in the oligonucleotide, and/or in regions which are 5' or 3' to the contiguous nucleotide sequence.

Examples of such modification of the nucleotide include modifying the sugar moiety to provide a 2'-substituent group or to produce a bridged (locked nucleic acid) structure which enhances binding affinity and may also provide increased nuclease resistance.

A preferred nucleotide analogue is LNA, such as oxy-LNA (such as beta-D-oxy-LNA, and alpha-L-oxy-LNA), and/or amino-LNA (such as beta-D-amino-LNA and alpha-L-amino-LNA) and/or thio-LNA (such as beta-D-thio-LNA and alpha-L-thio-LNA) and/or ENA (such as beta-D-ENA and alpha-L-ENA). Most preferred is beta-D-oxy-LNA.

In some embodiments the nucleotide analogues present within the oligomer of the invention (such as in regions A and C mentioned herein) are independently selected from, for example: 2'-O-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units and 2'MOE units. In some embodiments there is only one of the above types of nucleotide analogues present in the oligomer of the invention, or contiguous nucleotide sequence thereof.

In some embodiments the nucleotide analogues are 2'-O-methoxyethyl-RNA (2'MOE), 2'-fluoro-DNA monomers or LNA nucleotide analogues, and as such the oligonucleotide of the invention may comprise nucleotide analogues which are independently selected from these three types of analogue, or may comprise only one type of analogue selected from the three types. In some embodiments at least one of said nucleotide analogues is 2'-MOE-RNA, such as 2, 3, 4, 5, 6, 7, 8, 9 or 10 2'-MOE-RNA nucleotide units. In some embodiments at least one of said nucleotide analogues is 2'-fluoro DNA, such as 2, 3, 4, 5, 6, 7, 8, 9 or 10 2'-fluoro-DNA nucleotide units.

In some embodiments, the oligomer according to the invention comprises at least one Locked Nucleic Acid (LNA) unit, such as 1, 2, 3, 4, 5, 6, 7, or 8 LNA units, such as from 3-7 or 4 to 8 LNA units, or 3, 4, 5, 6 or 7 LNA units. In some embodiments, all the nucleotide analogues are LNA. In some embodiments, the oligomer may comprise both beta-D-oxy-LNA, and one or more of the following LNA units: thio-LNA, amino-LNA, oxy-LNA, and/or ENA in either the beta-D or alpha-L configurations or combinations thereof. In some embodiments all LNA cytosine units are 5' methyl-Cytosine. In some embodiments of the invention, the oligomer may comprise both LNA and DNA units. In some embodiments the combined total of LNA and DNA units is 7-18, such as 10-16, or 7-10. In some embodiments of the invention, the nucleotide sequence of the oligomer, such as the contiguous nucleotide sequence consists of at least one LNA and the remaining nucleotide units are DNA units. In some embodiments the oligomer comprises only LNA nucleotide analogues and naturally occurring nucleotides (such as RNA or DNA, most preferably DNA nucleotides), optionally with modified internucleotide linkages such as phosphorothioate.

The term "nucleobase" refers to the base moiety of a nucleotide and covers both naturally occurring a well as non-naturally occurring variants. Thus, "nucleobase" covers not only the known purine and pyrimidine heterocycles but also heterocyclic analogues and tautomeres thereof.

Examples of nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments, at least one of the nucleobases present in the oligomer is a modified nucleobase selected from the group consisting of 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

LNA

The term "LNA" refers to a bicyclic nucleoside analogue, known as "Locked Nucleic Acid". It may refer to an LNA monomer, or, when used in the context of an "LNA oligonucleotide", LNA refers to an oligonucleotide containing one or more such bicyclic nucleotide analogues. LNA nucleotides are characterised by the presence of a linker group (such as a bridge) between C2' and C4' of the ribose sugar ring—for example as shown as the biradical $R^{4*}$-$R^{2*}$ as described below.

The LNA used in the oligonucleotide compounds of the invention preferably has the structure of the general formula I

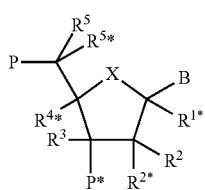

Formula 1 wherein for all chiral centers, asymmetric groups may be found in either R or S orientation;

wherein X is selected from —O—, —S—, —N($R^{N*}$)—, —C($R^6R^{6*}$)—, such as, in some embodiments —O—;

B is selected from hydrogen, optionally substituted $C_{1-4}$-alkoxy, optionally substituted $C_{1-4}$-alkyl, optionally substituted $C_{1-4}$-acyloxy, nucleobases including naturally occurring and nucleobase analogues, DNA intercalators, photochemically active groups, thermochemically active groups, chelating groups, reporter groups, and ligands; preferably, B is a nucleobase or nucleobase analogue;

P designates an internucleotide linkage to an adjacent monomer, or a 5'-terminal group, such internucleotide linkage or 5'-terminal group optionally including the substituent $R^5$ or equally applicable the substituent $R^{5*}$; P* designates an internucleotide linkage to an adjacent monomer, or a 3'-terminal group;

$R^{4*}$ and $R^{2*}$ together designate a bivalent linker group consisting of 1-4 groups/atoms selected from —C($R^aR^b$)—, —C($R^a$)=C($R^b$)—, —C($R^a$)=N—, —O—, —Si($R^a$)$_2$—, —S—, —SO$_2$—, —N($R^a$)—, and >C=Z, wherein Z is selected from —O—, —S—, and —N($R^a$)—, and $R^a$ and $R^b$ each is independently selected from hydrogen, optionally substituted $C_{1-12}$-alkyl, optionally substituted $C_{2-12}$-alkenyl, optionally substituted $C_{2-12}$-alkynyl, hydroxy, optionally substituted $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$), wherein for all chiral centers, asymmetric groups may be found in either R or S orientation, and; each of the substituents $R^{1*}$, $R^2$, $R^3$, $R^5$, $R^{5*}$, $R^6$ and $R^{6*}$, which are present is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted, and where two geminal substituents together may designate oxo, thioxo, imino, or optionally substituted methylene; wherein $R^N$ is selected from hydrogen and $C_{1-4}$-alkyl, and where two adjacent (non-geminal) substituents may designate an additional bond resulting in a double bond; and $R^{N*}$, when present and not involved in a biradical, is selected from hydrogen and $C_{1-4}$-alkyl; and basic salts and acid addition salts thereof. For all chiral centers, asymmetric groups may be found in either R or S orientation.

In some embodiments, $R^{4*}$ and $R^{2*}$ together designate a biradical consisting of a groups selected from the group consisting of C($R^aR^b$)—C($R^aR^b$)—, C($R^aR^b$)—O—, C($R^aR^b$)—NR$^a$—, C($R^aR^b$)—S—, and C($R^aR^b$)—C($R^aR^b$)—O—, wherein each $R^a$ and $R^b$ may optionally be independently selected. In some embodiments, $R^a$ and $R^b$ may be, optionally independently selected from the group consisting of hydrogen and $C_{1-6}$alkyl, such as methyl, such as hydrogen.

In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$-aminoalkyl. For all chiral centers, asymmetric groups may be found in either R or S orientation.

In some embodiments, $R^{4*}$ and $R^{2*}$ together designate the biradical —O—CH(CH$_2$OCH$_3$)— (2'O-methoxyethyl bicyclic nucleic acid—Seth at al., 2010, J. Org. Chem.)—in either the R— or S— configuration.

In some embodiments, $R^{4*}$ and $R^{2*}$ together designate the biradical —O(CH$_2$CH$_3$)— (2'O-ethyl bicyclic nucleic acid—Seth at al., 2010, J. Org. Chem.)—in either the R— or S— configuration.

In some embodiments, $R^{4*}$ and $R^{2*}$ together designate the biradical —O—CH(CH$_3$)— in either the R— or S— configuration. In some embodiments, $R^{4*}$ and $R^{2*}$ together designate the biradical —O—CH$_2$—O—CH$_2$—(Seth at al., 2010, J. Org. Chem.).

In some embodiments, $R^{4*}$ and $R^{2*}$ together designate the biradical —O—NR—CH$_3$—(Seth at al., 2010, J. Org. Chem.).

In some embodiments, the LNA units have a structure selected from the following group:

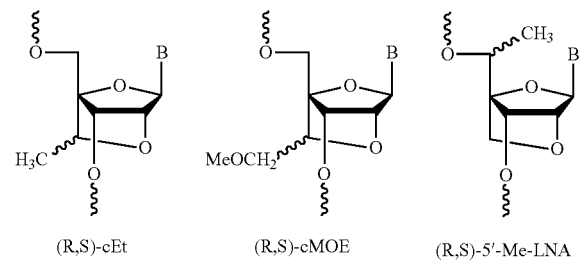

(R,S)-cEt   (R,S)-cMOE   (R,S)-5'-Me-LNA

In some embodiments, $R^{1*}$, $R^2$, $R^3$, $R^5$, $R^{5*}$ are hydrogen. In some embodiments, the MeOCH$_2$ group of the cMOE is replaced with an alkyl, such as a methyl group, and in this embodiment, $R^{1*}$, $R^2$, $R^3$, $R^5$, $R^{5*}$ any all be hydrogen.

In some embodiments, $R^{1*}$, $R^2$, $R^3$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$-aminoalkyl. For all chiral centers, asymmetric groups may be found in either R or S orientation.

In some embodiments, $R^{1*}$, $R^2$, $R^3$ are hydrogen. In some embodiments, $R^5$ and $R^{5*}$ are each independently selected from the group consisting of H, —CH$_3$, —CH$_2$—CH$_3$, —CH$_2$—O—CH$_3$, and —CH=CH$_2$. Suitably in some embodiments, either $R^5$ or $R^{5*}$ are hydrogen, where as the other group ($R^5$ or $R^{5*}$ respectively) is selected from the group consisting of $C_{1-5}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl or substituted acyl (—C(=O)—); wherein each substituted group is mono or poly substituted with substituent groups independently selected from halogen, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, OJ$_1$, SJ$_1$, NJ$_1$J$_2$, N$_3$, COOJ$_1$, CN, O—C(=O)NJ$_1$J$_2$, N(H)C(=NH)NJ$_1$J$_2$ or N(H)O(=X)N(H)J$_2$ wherein X is O or S; and each J$_1$ and J$_2$ is, independently, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{1-6}$-aminoalkyl, substituted $C_{1-6}$-aminoalkyl or a protecting group. In some embodiments either $R^5$ or $R^{5*}$ is substituted $C_{1-6}$alkyl. In some embodiments either $R^5$ or $R^{5*}$ is substituted methylene wherein preferred substituent groups include one or more groups independently selected from F, NJ$_1$J$_2$, N$_3$, CN, OJ$_1$, SJ$_1$, O—C(=O)NJ$_1$J$_2$, N(H)O(=NH)NJ, J$_2$ or N(H)C(O)N(H)J$_2$. In some embodiments each J$_1$ and J$_2$ is, independently H or $C_{1-6}$ alkyl. In some embodiments either $R^5$ or $R^{5*}$ is methyl, ethyl or methoxymethyl. In some embodiments either $R^5$ or $R^{5*}$ is methyl. In a further embodiment either $R^5$ or $R^{5*}$ is ethylenyl. In some embodiments either $R^5$ or $R^{5*}$ is substituted acyl. In some embodiments either $R^5$ or $R^{5*}$ is C(=O)NJ$_1$J$_2$. For all chiral centers, asymmetric groups may be found in either R or S orientation. Such 5' modified bicyclic nucleotides are disclosed in WO 2007/134181, which is hereby incorporated by reference in its entirety.

In some embodiments B is a nucleobase, including nucleobase analogues and naturally occurring nucleobases, such as a purine or pyrimidine, or a substituted purine or substituted pyrimidine, such as a nucleobase referred to herein, such as a nucleobase selected from the group consisting of adenine, cytosine, thymine, adenine, uracil, and/or a modified or substituted nucleobase, such as 5-thiazolo-uracil, 2-thio-uracil, 5-propynyl-uracil, 2' thio-thymine, 5-methyl cytosine, 5-thiozolo-cytosine, 5-propynyl-cytosine, and 2,6-diaminopurine.

In some embodiments, $R^{4*}$ and $R^{2*}$ together designate a biradical selected from —C($R^aR^b$)—O—, —C($R^aR^b$)—C($R^cR^d$)—O—, —C($R^aR^b$)—C($R^cR^d$)—C($R^eR^f$)—O—, —C($R^aR^b$)—O—C($R^cR^d$)—, —C($R^aR^b$)—O—C($R^cR^d$)—O—, —C($R^aR^b$)—C($R^cR^d$)—, —C($R^aR^b$)—C($R^cR^d$)—C($R^eR^f$)—, —C($R^a$)=C($R^b$)—C($R^cR^d$)—, —C($R^eR^b$)—N($R^c$)—, —C($R^eR^b$)—C($R^cR^d$)—N($R^e$)—, —C($R^eR^b$)—N($R^c$)—O—, and —C($R^aR^b$)—S—, —C($R^aR^b$)—C($R^cR^d$)—S—, wherein $R^a$, $R^b$, $R^c$, $R^d$, $R^e$, and $R^f$ each is independently selected from hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=CH$_2$). For all chiral centers, asymmetric groups may be found in either R or S orientation.

In a further embodiment $R^{4*}$ and $R^{2*}$ together designate a biradical (bivalent group) selected from —CH$_2$—O—, —CH$_2$—S—, —CH$_2$—NH—, —CH$_2$—N(CH$_3$)—, —CH$_2$—CH$_2$—O—, —CH$_2$—CH(CH$_3$)—, —CH$_2$—CH$_2$—S—, —CH$_2$—CH$_2$—NH—, —CH$_2$—CH$_2$—CH$_2$—, —CH$_2$—CH$_2$—CH$_2$—O—, —CH$_2$—CH$_2$—CH(CH$_3$)—, —CH=CH—CH$_2$—, —CH$_2$—O—CH$_2$—O—, —CH$_2$—NH—O—, —CH$_2$—N(CH$_3$)—O—, —CH$_2$—O—CH$_2$—, —CH(CH$_3$)—O—, and —CH(CH$_2$—O—CH$_3$)—O—, and/or, —CH$_2$—CH$_2$—, and —CH=CH—For all chiral centers, asymmetric groups may be found in either R or S orientation.

In some embodiments, $R^{4*}$ and $R^{2*}$ together designate the biradical C($R^aR^b$)—N($R^c$)—O—, wherein $R^a$ and $R^b$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen, and; wherein $R^c$ is selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ together designate the biradical C($R^aR^b$)—O—C($R^cR^d$)—O—, wherein $R^a$, $R^b$, $R^c$, and $R^d$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$ alkoxyl, substituted $C_{1-6}$ alkoxyl, acyl, substituted acyl, $C_{1-6}$ aminoalkyl or substituted $C_{1-6}$ aminoalkyl, such as hydrogen.

In some embodiments, $R^{4*}$ and $R^{2*}$ form the biradical —CH(Z)—O—, wherein Z is selected from the group consisting of $C_{1-6}$ alkyl, $C_{2-6}$ alkenyl, $C_{2-6}$ alkynyl, substituted $C_{1-6}$ alkyl, substituted $C_{2-6}$ alkenyl, substituted $C_{2-6}$ alkynyl, acyl, substituted acyl, substituted amide, thiol or substituted thio; and wherein each of the substituted groups, is, independently, mono or poly substituted with optionally protected substituent groups independently selected from halogen, oxo, hydroxyl, $OJ_1$, $NJ_1J_2$, $SJ_1$, $N_3$, $OC(=X)J_1$, $OC(=X)NJ_1J_2$, $NJ^3C(=X)NJ_1J_2$ and CN, wherein each $J_1$, $J_2$ and $J_3$ is, independently, H or $C_{1-6}$ alkyl, and X is O, S or $NJ_1$. In some embodiments Z is $C_{1-6}$ alkyl or substituted $C_{1-6}$ alkyl. In some embodiments Z is methyl. In some embodiments Z is substituted $C_{1-6}$alkyl. In some embodiments said substituent group is $C_{1-6}$alkoxy. In some embodiments Z is $CH_3OCH_2$—. For all chiral centers, asymmetric groups may be found in either R or S orientation. Such bicyclic nucleotides are disclosed in U.S. Pat. No. 7,399,845 which is hereby incorporated by reference in its entirety. In some embodiments, $R^{1*}$, $R^2$, $R^3$, $R^5$, $R^{5*}$ are hydrogen. In some embodiments, $R^{1*}$, $R^2$, $R^{3*}$ are hydrogen, and one or both of $R^5$, $R^{5*}$ may be other than hydrogen as referred to above and in WO 2007/134181.

In some embodiments, $R^{4*}$ and $R^{2*}$ together designate a biradical which comprise a substituted amino group in the bridge such as consist or comprise of the biradical —$CH_2$—N($R^c$)—, wherein $R^c$ is $C_{1-12}$ alkyloxy. In some embodiments $R^{4*}$ and $R^{2*}$ together designate a biradical -$C_{q_3}q_4$-NOR—, wherein $q_3$ and $q_4$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$ alkoxyl, acyl, substituted acyl, $C_{1-6}$-aminoalkyl or substituted $C_{1-6}$ aminoalkyl; wherein each substituted group is, independently, mono or poly substituted with substituent groups independently selected from halogen, $OJ_1$, $SJ_1$, $NJ_1J_2$, $COOJ_1$, CN, O—C(=O)$NJ_1J_2$, N(H)C(=NH)$NJ_1J_2$ or N(H)C(=X=N(H)J_2$ wherein X is O or S; and each of $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group. For all chiral centers, asymmetric groups may be found in either R or S orientation. Such bicyclic nucleotides are disclosed in WO2008/150729 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$ alkoxyl, acyl, substituted acyl, $C_{1-6}$-aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181. In some embodiments $R^{4*}$ and $R^{2*}$ together designate a biradical (bivalent group) C($R^aR^b$)—O—, wherein $R^a$ and $R^b$ are each independently halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_1$, $SJ_1$, $SOJ_1$, $SO_2J_1$, $NJ_1J_2$, $N_3$, CN, C(=O)$OJ_1$, C(=O)$NJ_1J_2$, C(=O)$J_1$, O—C(=O)$NJ_1J_2$, N(H)C(=NH)$NJ_1J_2$, N(H)C(=O)$NJ_1J_2$ or N(H)C(=S)$NJ_1J_2$; or $R^a$ and $R^b$ together are =C(q3)(q4); $q_3$ and $q_4$ are each, independently, H, halogen, $O_1$—$C_{1-2}$alkyl or substituted $C_1$-$C_{12}$ alkyl; each substituted group is, independently, mono or poly substituted with substituent groups independently selected from halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ or N(H)C(=S)$NJ_1J_2$ and; each $J_1$ and $J_2$ is, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ aminoalkyl, substituted $C_1$-$C_6$ aminoalkyl or a protecting group. Such compounds are disclosed in WO2009006478A, hereby incorporated in its entirety by reference.

In some embodiments, $R^{4*}$ and $R^{2*}$ form the biradical -Q-, wherein Q is C($q_1$)($q_2$)C($q_3$)($q_4$), C($q_1$)=C($q_3$), C[=C($q_1$)($q_2$)]—C($q_3$)($q_4$) or C($q_1$)($q_2$)—C[=C($q_3$)($q_4$)]; $q_1$, $q_2$, $q_3$, $q_4$ are each independently. H, halogen, $C_{1-12}$ alkyl, substituted $C_{1-12}$ alkyl, $C_{2-12}$ alkenyl, substituted $C_{1-12}$ alkoxy, $OJ_1$, $SJ_1$, $SOJ_1$, $SO_2J_1$, $NJ_1J_2$, $N_3$, CN, C(=O)$OJ_1$, C(=O)—$NJ_1J_2$, C(=O) $J_1$, —C(=O)$NJ_1J_2$, N(H)C(=NH)$NJ_1J_2$, N(H)C(=O)$NJ_1J_2$ or N(H)C(=S)$NJ_1J_2$; each $J_1$ and $J_2$ is, independently, H, $C_{1-6}$ alkyl, $C_{2-6}$ alkenyl, $C_{2-6}$ alkynyl, $C_{1-6}$ aminoalkyl or a protecting group; and, optionally wherein when Q is C($q_1$)($q_2$)($q_3$)($q_4$) and one of $q_3$ or $q_4$ is $CH_3$ then at least one of the other of $q_3$ or $q_4$ or one of $g_1$ and $q_2$ is other than H. In some embodiments, $R^{1*}$, $R^2$, $R^3$, $R^5$, $R^{5*}$ are hydrogen. For all chiral centers, asymmetric groups may be found in either R or S orientation. Such bicyclic nucleotides are disclosed in WO2008/154401 which is hereby incorporated by reference in its entirety. In some embodiments, $R^{1*}$, $R^2$, $R^3$, $R^5$, $R^{5*}$ are independently selected from the group consisting of hydrogen, halogen, $C_{1-6}$ alkyl, substituted $C_{1-6}$ alkyl, $C_{2-6}$ alkenyl, substituted $C_{2-6}$ alkenyl, $C_{2-6}$ alkynyl or substituted $C_{2-6}$ alkynyl, $C_{1-6}$alkoxyl, substituted $C_{1-6}$alkoxyl, acyl, substituted acyl, $C_{1-6}$ aminoalkyl or substituted $C_{1-6}$ aminoalkyl. In some embodiments, $R^{1*}$, $R^2$, $R^3$, $R^5$, $R^{5*}$ are hydrogen. In some embodiments, $R^{1*}$, $R^2$, $R^3$ are hydrogen and one or both of $R^5$, $R^{5*}$ may be other than hydrogen as referred to above and in WO 2007/134181 or WO2009/067647 (alpha-L-bicyclic nucleic acids analogs).

In some embodiments the LNA used in the oligonucleotide compounds of the invention preferably has the structure of the general formula II:

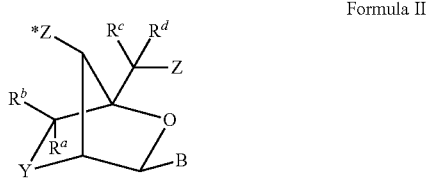

Formula II wherein Y is selected from the group consisting of —O—, —$CH_2$O—, —S—, —NH—, N($R^a$) and/or —$CH_2$—; Z and Z* are independently selected among an internucleotide linkage, $R^H$, a terminal group or a protecting group; B constitutes a natural or non-natural nucleotide base moiety optionally independently, selected from the group consisting of hydrogen, optionally substituted $C_{1-12}$-alkyl, optionally substituted $C_{2-12}$-alkenyl, optionally substituted $C_{2-12}$-alkynyl, hydroxy, $C_{1-12}$-alkoxy, $C_{2-12}$-alkoxyalkyl, $C_{2-12}$-alkenyloxy, carboxy, $C_{1-12}$-alkoxycarbonyl, $C_{1-12}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, DNA intercalators, photochemically active groups, thermochemically active groups, chelating groups, reporter groups, and ligands, where aryl and heteroaryl may be optionally substituted and where two geminal substituents $R^a$ and $R^b$ together may designate optionally substituted methylene (=$CH_2$); and $R^H$ is selected from hydrogen and $C_{1-4}$-alkyl. In some embodiments $R^a$, $R^bR^c$, $R^d$ and $R^e$ are, option ally independently, selected from the group consisting of hydrogen and $C_{1-6}$ alkyl, such as methyl. For all chiral centers, asymmetric groups may be found in either R or S orientation, for example, two exemplary stereochemical isomers include the beta-D and alpha-L isoforms, which may be illustrated as follows:

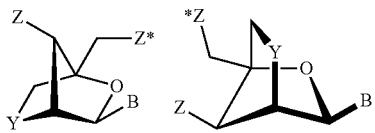

Specific exemplary LNA units are shown below:

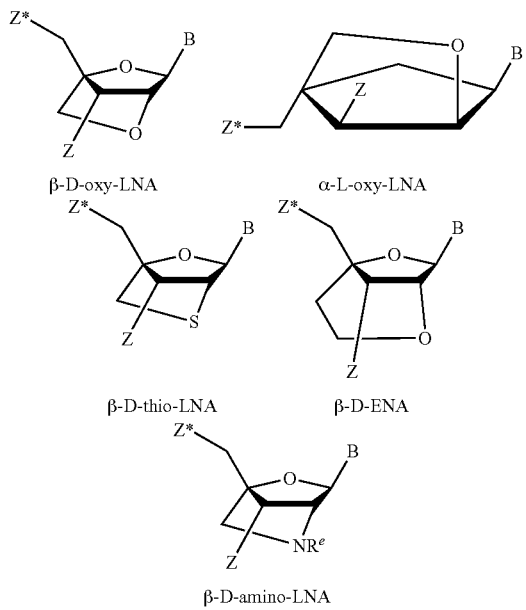

The term "thio-LNA" comprises a locked nucleotide in which Y in the general formula above is selected from S or —$CH_2$—S—. Thio-LNA can be in both beta-D and alpha-L-configuration.

The term "amino-LNA" comprises a locked nucleotide in which Y in the general formula above is selected from —N(H)—, N(R)—, $CH_2$—N(H)—, and —$CH_2$—N(R)— where R is selected from hydrogen and $C_{1-4}$-alkyl. Amino-LNA can be in both beta-D and alpha-L-configuration.

The term "oxy-LNA" comprises a locked nucleotide in which Y in the general formula above represents —O—. Oxy-LNA can be in both beta-D and alpha-L-configuration. The term "ENA" comprises a locked nucleotide in which Y in the general formula above is —$CH_2$—O— (where the oxygen atom of —$CH_2$—O— is attached to the 2'-position relative to the base B). $R^e$ is hydrogen or methyl.

In some exemplary embodiments LNA is selected from beta-D-oxy-LNA, alpha-L-oxy-LNA, beta-D-amino-LNA and beta-D-thio-LNA, in particular beta-D-oxy-LNA.

Internucleotide Linkages

The monomers of the LNA oligomers described herein are coupled together via linkage groups. Suitably, each monomer is linked to the 3' adjacent monomer via a linkage group.

The person having ordinary skill in the art would understand that, in the context of the present invention, the 5' monomer at the end of an oligomer does not comprise a 5' linkage group, although it may or may not comprise a 5' terminal group.

The terms "linkage group" or "internucleotide linkage" are intended to mean a group capable of covalently coupling together two nucleotides. Specific and preferred examples include phosphate groups and phosphorothioate groups.

The nucleotides of the oligomer of the invention or contiguous nucleotides sequence thereof are coupled together via linkage groups. Suitably each nucleotide is linked to the 3' adjacent nucleotide via a linkage group.

Suitable internucleotide linkages include those listed within WO2007/031091, for example the internucleotide linkages listed on the first paragraph of page 34 of WO2007/031091 (hereby incorporated by reference).

It is, in some embodiments, preferred to modify the internucleotide linkage from its normal phosphodiester to one that is more resistant to nuclease attack, such as phosphorothioate or boranophosphate—these two, being cleavable by RNase H, also allow that route of antisense inhibition in reducing the expression of the target gene.

Suitable sulphur (S) containing internucleotide linkages as provided herein may be preferred. Phosphorothioate internucleotide linkages are also preferred, particularly for the gap region (B) of gapmers. In gapmers for example, phosphorothioate linkages may also be used for the flanking regions (A and C, and for linking A or C to D, and within region D, as appropriate). Regions A, B and C, may, in some embodiments, comprise internucleotide linkages other than phosphorothioate, such as phosphodiester linkages, particularly, for instance when the use of nucleotide analogues protects the internucleotide linkages within regions A and C from endonuclease degradation—such as when regions A and C comprise LNA nucleotides.

The internucleotide linkages in the oligomer may be phosphodiester, phosphorothioate or boranophosphate so as to allow RNase H cleavage of targeted RNA. Phosphorothioate is preferred, for improved nuclease resistance and other reasons, such as ease of manufacture.

In one aspect of the oligomer of the invention, the nucleotides and/or nucleotide analogues are linked to each other by means of phosphorothioate groups.

It is recognised that the inclusion of phosphodiester linkages, such as one or two linkages, into an otherwise phosphorothioate oligomer, particularly between or adjacent to nucleotide analogue units (typically in region A and or C) can modify the bioavailability and/or bio-distribution of an oligomer—see WO2008/053314, hereby incorporated by reference.

In some embodiments, such as the embodiments referred to above, where suitable and not specifically indicated, all remaining linkage groups are either phosphodiester or phosphorothioate, or a mixture thereof.

In some embodiments all the internucleotide linkage groups are phosphorothioate.

When referring to LNA oligomers it will be understood that, in various embodiments, when the linkages are phosphorothioate linkages, alternative linkages, such as those disclosed herein may be used, for example phosphate (phosphodiester) linkages may be used, particularly for linkages between nucleotide analogues, such as LNA, units. Likewise, when referring to specific gapmer oligonucleotide sequences, such as those provided herein, when the C residues are annotated as 5' methyl modified cytosine, in various embodiments, one or more of the Cs present in the oligomer may be unmodified C residues.

Conjugates

In the context the term "conjugate" is intended to indicate a heterogenous molecule formed by the covalent attachment ("conjugation") of the oligomer as described herein to one or more non-nucleotide, or non-polynucleotide moieties. Examples of non-nucleotide or non-polynucleotide moieties include macromolecular agents such as proteins, fatty acid chains, sugar residues, glycoproteins, polymers, or combinations thereof. Typically proteins may be antibodies for a target protein. Typical polymers may be polyethylene glycol.

The oligomers of the invention may also be conjugated to active drug substances, for example, aspirin, ibuprofen, a sulfa drug, an antidiabetic, an antibacterial or an antibiotic.

In certain embodiments the conjugated moiety is a sterol, such as cholesterol.

In various embodiments, the conjugated moiety comprises or consists of a positively charged polymer, such as a positively charged peptides of, for example from 1-50, such as 2-20 such as 3-10 amino acid residues in length, and/or polyalkylene oxide such as polyethylglycol (PEG) or polypropylene glycol—see WO 2008/034123, hereby incorporated by reference. Suitably the positively charged polymer, such as a polyalkylene oxide may be attached to the oligomer of the invention via a linker such as the releasable inker described in WO 2008/034123.

By way of example, the following conjugate moieties may be used in the conjugates of the invention:

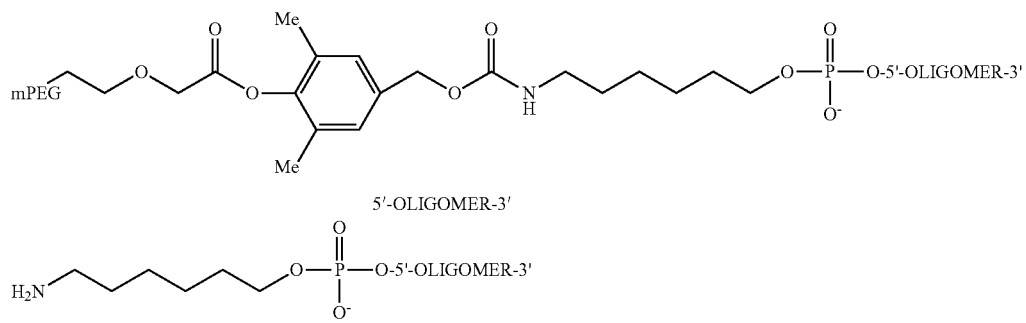

Therefore, in various embodiments, the oligomer of the invention may comprise both a polynucleotide region which typically consists of a contiguous sequence of nucleotides, and a further non-nucleotide region. When referring to the oligomer of the invention consisting of a contiguous nucleotide sequence, the compound may comprise non-nucleotide components, such as a conjugate component.

In various embodiments of the invention the oligomeric compound is linked to ligands/conjugates, which may be used, e.g. to increase the cellular uptake of oligomeric compounds. WO2007/031091 provides suitable ligands and conjugates, which are hereby incorporated by reference.

The invention also provides for a conjugate comprising the compound according to the invention as herein described, and at least one non-nucleotide or non-polynucleotide moiety covalently attached to said compound. Therefore, in various embodiments where the compound of the invention consists of a specified nucleic acid or nucleotide sequence, as herein disclosed, the compound may also comprise at least one non-nucleotide or non-polynucleotide moiety (e.g. not comprising one or more nucleotides or nucleotide analogues) covalently attached to said compound.

Conjugattion (to a conjugate moiety) may enhance the activity, cellular distribution or cellular uptake of the oligomer of the invention. Such moieties include, but are not limited to, antibodies, polypeptides, lipid moieties such as a cholesterol moiety, cholic acid, a thioether, e.g. Hexyl-s-tritylthiol, a thiocholesterol, an aliphatic chain, e.g., dodecandiol or undecyl residues, a phospholipids, e.g., di-hexadecyl-rac-glycerol or triethylammonium 1,2-di-o-hexadecyl-rac-glycero-3-h-phosphonate, a polyamine or a polyethylene glycol chain, an adamantane acetic acid, a palmityl moiety, an octadecylamine or hexylamino-carbonyl-oxycholesterol moiety.

Activated Oligomers

The term "activated oligomer," as used herein, refers to an oligomer of the invention that is covalently linked (i.e., functionalized) to at least one functional moiety that permits covalent linkage of the oligomer to one or more conjugated moieties, i.e., moieties that are adenine base, a spacer that is preferably hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999). Examples of suitable hydroxyl protecting groups include esters such as acetate ester, aralkyl groups such as benzyl, diphenylmethyl, or triphenylmethyl, and tetrahydropyranyl. Examples of suitable amino protecting groups include benzyl, alpha-methylbenzyl, diphenylmethyl, triphenylmethyl, benzyloxycarbonyl, tert-butoxycarbonyl, and acyl groups such as trichloroacetyl or trifluoroacetyl. In some embodiments, the functional moiety is self-cleaving. In other embodiments, the functional moiety is biodegradable. See e.g., U.S. Pat. No. 7,087,229, which is incorporated by reference herein in its entirety.

In some embodiments, oligomers of the invention are functionalized at the 5' end in order to allow covalent attachment of the conjugated moiety to the 5' end of the oligomer. In other embodiments, oligomers of the invention can be functionalized at the 3' end. In still other embodiments, oligomers of the invention can be functionalized along the backbone or on the heterocyclic base moiety. In yet other embodiments, oligomers of the invention can be functionalized at more than one position independently selected from the 5' end, the 3' end, the backbone and the base.

In some embodiments, activated oligomers of the invention are synthesized by incorporating during the synthesis one or more monomers that is covalently attached to a functional moiety. In other embodiments, activated oligomers of the invention are synthesized with monomers that have not been functionalized, and the oligomer is functionalized upon completion of synthesis. In some embodiments, the oligomers are functionalized with a hindered ester containing an aminoalkyl linker, wherein the alkyl portion has the formula $(CH_2)_w$, wherein w is an integer ranging from 1 to 10, preferably about 6, wherein the alkyl portion of the alkylamino group can be straight chain or branched chain, and wherein the functional group is attached to the oligomer via an ester group (—O—C(O)—$(CH_2)_w$NH).

In other embodiments, the oligomers are functionalized with a hindered ester containing a $(CH_2)_w$-sulfhydryl (SH) linker, wherein w is an integer ranging from 1 to 10, preferably about 6, wherein the alkyl portion of the alkylamino group can be straight chain or branched chain, and wherein the functional group attached to the oligomer via an ester group (—O—C(O)—$(CH_2)_w$SH)

In some embodiments, sulfhydryl-activated oligonucleotides are conjugated with polymer moieties such as polyethylene glycol or peptides (via formation of a disulfide bond).

Activated oligomers containing hindered esters as described above can be synthesized by any method known in the art, and in particular by methods disclosed in PCT Publication No. WO 2008/034122 and the examples therein, which is incorporated herein by reference in its entirety.

In still other embodiments, the oligomers of the invention are functionalized by introducing sulfhydryl, amino or hydroxyl groups into the oligomer by means of a functionalizing reagent substantially as described in U.S. Pat. Nos. 4,962,029 and 4,914,210, i.e., a substantially linear reagent having a phosphoramidite at one end linked through a hydrophilic spacer chain to the opposing end which comprises a protected or unprotected sulfhydryl, amino or hydroxyl group. Such reagents primarily react with hydroxyl groups of the oligomer. In some embodiments, such activated oligomers have a functionalizing reagent coupled to a 5'-hydroxyl group of the oligomer. In other embodiments, the activated oligomers have a functionalizing reagent coupled to a 3'-hydroxyl group. In still other embodiments, the activated oligomers of the invention have a functionalizing reagent coupled to a hydroxyl group on the backbone of the oligomer. In yet further embodiments, the oligomer of the invention is functionalized with more than one of the functionalizing reagents as described in U.S. Pat. Nos. 4,962,029 and 4,914,210, incorporated herein by reference in their entirety. Methods of synthesizing such functionalizing reagents and incorporating them into monomers or oligomers are disclosed in U.S. Pat. Nos. 4,962,029 and 4,914,210.

In some embodiments, the 5'-terminus of a solid-phase bound oligomer is functionalized with a dienyl phosphoramidite derivative, followed by conjugation of the deprotected oligomer with, e.g., an amino acid or peptide via a Diels-Alder cycloaddition reaction.

In various embodiments, the incorporation of monomers containing 2'-sugar modifications, such as a 2'-carbamate substituted sugar or a 2'-(O-pentyl-N-phthalimido)-deoxyribose sugar into the oligomer facilitates covalent attachment of conjugated moieties to the sugars of the oligomer. In other embodiments, an oligomer with an amino-containing linker at the 2'-position of one or more monomers is prepared using a reagent such as, for example, 5'-dimethoxytrityl-2'-O-(e-phthalimidylaminopentyl)-2'-deoxyadenosine-3'-N,N-diisopropyl-cyanoethoxy phosphoramidite. See, e.g., Manoharan, et al., Tetrahedron Letters, 1991, 34, 7171.

In still further embodiments, the oligomers of the invention may have amine-containing functional moieties on the nucleobase, including on the N6 purine amino groups, on the exocyclic N2 of guanine, or on the N4 or 5 positions of cytosine. In various embodiments, such functionalization may be achieved by using a commercial reagent that is already functionalized in the oligomer synthesis.

Some functional moieties are commercially available, for example, heterobifunctional and homobifunctional linking moieties are available from the Pierce Co. (Rockford, Ill.). Other commercially available linking groups are 5'-Amino-Modifier C6 and 3'-Amino-Modifier reagents, both available from Glen Research Corporation (Sterling, Va.). 5'-Amino-Modifier C6 is also available from ABI (Applied Biosystems Inc., Foster City, Calif.) as Aminolink-2, and 3'-Amino-Modifier is also available from Clontech Laboratories Inc. (Palo Alto, Calif.).

EMBODIMENTS

1. A medicament composition for oral administration to a subject in need of treatment, comprising an effective amount of at least one therapeutically effective LNA oligomer, and a pharmaceutically acceptable carrier.
2. The medicament composition according to embodiment 1 for use in medicine.
3. The medicament composition according to embodiment 1 or 2, wherein the medicament composition comprises less than 90% water.
4. The medicament composition according to any one of embodiments 1-3, wherein the composition comprises one or more penetration enhancers, such as sodium caprate (C10).
5. The medicament composition according to embodiment 4, wherein the penetration enhancer is dosed at a level less than 50 mgs per kg of body mass of the subject in need of treatment, such as less than 25 mgs/kg.
6. The medicament composition according to any one of embodiments 1-5, wherein the composition comprises a delayed release formulation of the at least one LNA oligomer.
7. The medicament according to any one of embodiments 1-6, wherein the pharmaceutically acceptable carrier is a solid.
8. The medicament composition according to any one of embodiments 1-7, wherein the composition comprises a pharmaceutically acceptable excipient.
9. The medicament composition according to any one of embodiments 1-8, wherein the composition is encapsulated or is otherwise coated in an enteric material.
10. The medicament composition according to any one of embodiments 1-9, wherein the at least one LNA oligomer is dosed at a level of between 1 mg/kg and 200 mg/kg, as determined per kg of body mass of the subject in need of treatment.
11. The medicament composition according to any one of embodiments 1-10 which further comprises at least one further therapeutically active compound.
12. The medicament composition of any one of embodiments 1-11, wherein the medicament is in a unit dose form, such as a tablet, a capsule or a pill.
13. The medicament composition according to any one of embodiments 1-12, wherein the oral bioavailability (F) of the LNA oligomer is at least 10%.

14. The medicament composition according to any one of embodiments 1-13, wherein the LNA oligomer targets ApoB-100 or PSCK9 or microRNA-122 or microRNA-21.
15. The medicament composition according to any one of embodiments 1-14, wherein the composition comprises at least one further therapeutic compound used in the treatment of hyperlipidemia or associated disorders, such as at least one statin compound.
16. The medicament composition according to embodiment 14 or 15, wherein the medicament composition is for the use in treatment of hyperlipidemia or an associated disorder.
17. The medicament composition according to embodiment 14, wherein the LNA oligomer targets microRNA-122.
18. The medicament composition according to embodiment 17, wherein the medicament composition comprises a further therapeutic compound used in the treatment of Hepatitis C, such as interferon.
19. The medicament composition according to embodiment 17 or 18, wherein the medicament composition is for the treatment of hepatitis C.
20. The medicament composition according to any one of embodiments 1-14, wherein the LNA oligomer targets a microRNA and the LNA oligomer is a antimiR or a micromiR which targets said microRNA.
21. A therapeutically effective LNA oligomer for use as a medicament for oral administration.
22. The therapeutically effective LNA oligomer according to embodiment 21, wherein the medicament is in the form of the medicament composition of any one of embodiments 1-20.
23. Use of a LNA oligomer for the manufacture of a medicament, wherein the medicament is for oral delivery.
24. The use according to embodiment 23, wherein the medicament is in the form of the medicament composition of any one of embodiments 1-20.
25. A method of treatment of a medical disease or disorder, said method comprising administering a therapeutically effective amount of a LNA oligomer to a subject in need of said treatment, wherein said administration is one or more oral administrations of said LNA oligomer.
26. The method according to embodiment 25, wherein said medical disease or disorder is hyperlipidemia or a related disorder.
27. The method according to embodiment 26, wherein said LNA oligomer is an oligomer which targets ApoB-100 or PSCK9 or microRNA-122.
28. The method according to any one of embodiments 25-26, wherein said method of treatment further comprises the administration of at least one further therapeutic compound, such as a therapeutic compound for the treatment of hyperlipidemia or a related disorder, such as a statin.
29. The method according to embodiment 25, wherein said medical disease or disorder is a viral infection, such as hepatitis C.
30. The method according to embodiment 29, wherein said LNA oligomer is an oligomer which targets microRNA-122.
31. The method according to any one of embodiments 29 or 30, wherein said method of treatment further comprises the administration of at least one further therapeutic compound, such as a therapeutic compound for the treatment of virus infection, such as hepatitis C infection, such as interferon.
32. The method according to embodiment 28 or 31, wherein the at least one further therapeutic compound is administered prior to, concurrent to, or subsequent to, the administration of the LNA oligomer.
33. The method according to embodiment 25, wherein said medical disease or disorder is associated with the expression or over-expression of a microRNA and wherein said LNA oligomer is a antimiR or micromiR targeted to said microRNA.
34. A method for modulating the expression of a gene in a mammal, comprising orally administering a LNA oligomer to the mammal.
35. The method according to embodiment 34, wherein the gene is a microRNA and the LNA oligomer is a antimiR or micromiR, which targets said microRNA.

EXAMPLES

Oligonucleotides

Beta-D-oxy LNA monomers: Capital letters; DNA monomers: Lower-case letters Internucleoside linkages: Subscript letters (s=phosphorothioates). LNA cytosines=5'-methyl cytosine.

SEQ ID NO 36
COMPOUND A (SPC3883) = 5'-$G_s{}^mC_sa_st_st_sg_sg_st_sa_st_sT{}^mC_sA$-3'
(compound A)

COMPOUND B =
(SEQ ID NO: 37)
5'-$^mC_sC_sA_st_st_sG_sT_sC_sa_s{}^mC_sa_s{}^mC_sT_s{}^mC_s{}^mC$-3'

Compound B is an anti-microRNA compound which specifically targets microRNA-122 (hsa-miR 122). Compound B is also a regulator of ApoB-100 and as such the assays provided above in relation to compound A analysis may also be used for compound B.

(SEQ ID NO 38)
COMPOUND C = 5'-$G_sT_st_sg_sa_sc_sa_sc_st_sg_sT_s{}^mC$-3'

Compound C is an improved LNA oligomer which also targets ApoB.

COMPOUND D = $G_sA_sT_sA_sA_sG_s{}^mC_sT$

Compound D is an anti-microRNA compound which specifically targets the microRNA-21 (hsa-miR 21) seed region.

Example 1

Mouse Studies

Materials and Methods
Animals

Inbred C57BL/6J female mice were obtained from Taconic (Denmark). All mice were fed ad libitum with a commercially pelleted mouse purified diet (C1000, Gentofte, Denmark) containing four weight percent fat for two weeks before initiation of the study. The animal room was illuminated to give a cycle of 12 hours light and 12 hours darkness and temperature control was 21° C.±2° C. and relative humidity 55±10%.

Weekly during the study retro-orbital sinus blood was collected in S-monovette Serum-Gel vials (Sarstedt, Numbrecht, Germany) for serum preparation. At sacrifice mice were anesthetized (70% $CO_2$/30% $O_2$) before blood sampling and cervical dislocated before livers and jejunums were collected in RNA later (Sigma-Aldrich) or snap frozen in liquid nitrogen.

All in vivo experiments were performed according to the principles stated in the Danish law on animal experiments and were approved by the Danish National Committee for Animal Experiments, Ministry of Justice, Denmark.

Treatment

At the start of the experimental treatment period all mice were switched to enriched diets. The enriched diets were based on C1000 with addition of eight weight percent sodium decanoate (Na-caprate) as penetration enhancer and one weight percent polyethylene glycol (PEG; Pluriol E3405, BASF) as binder. All animals were fed the enriched diet and for the group treated with orally administered SPC3833 the LNA oligonucleotide was mixed in the feed (0.1%, w/w). Enriched diet±SPC3833 was manufactured by Altromin GmbH & Co, Germany. As positive control, one group of animals on enriched diet without added SPC3833 were subcutaneously injected with SPC3833 (1.0 mg/kg/week) formulated in saline. All animals (n=10/group) were kept on the enriched diet (±orally or subcutaneously administered SPC3833) for six weeks. At day 42 after beginning of treatment five animals/group were sacrificed, whereas five animals/group were continued on enriched diet without SPC3833 for an additional two weeks as wash-out.

Serum Analyses

Serum total cholesterol, triglyceride, and alanine aminotransferase (ALT) content was analyzed using ABX Pentra Cholesterol CP, ABX Pentra Glycerides CP, and ALT CP reagents, respectively (Horiba ABX Diagnostics, France). All three assays were performed according to the manufacturer's instruction but adjusted to 96-well format, using dilutions series of MultiCal (ABX Pentra) as standards.

Analysis of serum lipoprotein fraction cholesterol content was performed using a Shimadzu FPLC (fast protein liquid chromatography) system with a knitted teflon coil (Supelco) as reaction chamber and a 25 ml Superose 6 column (GE Healthcare). The method used was adapted from Garber et al. In short, 10-15 µl aliquots of serum were injected by a Shimadzu autosampler and separated in lipoprotein fractions by size exclusion chromatography before entering the reaction chamber where it was mixed with colourimetric cholesterol reagent (Infinity reagent, TR13521, Thermo Trace). The reaction proceeded at 37° C. for five minutes resulting in full colour development followed by detection (480 nM) and quantification by LC solution software (Shimadzu). Area under curve (AUC) is directly proportional to cholesterol content/fraction and absolute levels were calculated by comparison with a control sample with known cholesterol concentration.

Quantitative RT-PC

Total RNA was extracted from cell lysates or liver tissue homogenate using the spin column method of RNeasy mini kit (Qiagen) according to the manufacturer's instructions. mRNA quantification of selected genes was carried out using commercially available TaqMan assays (Applied Biosystems). First strand cDNA was generated from total RNA by reverse transcription reaction using random decamers, 0.5 µg total RNA, and the M-MLV RT enzyme (Ambion) according to manufacturer's instructions. Applied Biosystems 7500Fast real-time PCR instrument was used for amplification. Data were analyzed and quantified using the 7500Fast SDS software. ApoB mRNA levels were normalized to GAPDH and presented relative to saline control.

Statistical Analysis:

Statistical analyses were performed using Student's t-test. P values of <0.05 were considered to be of statistical significance.

Figure 1:
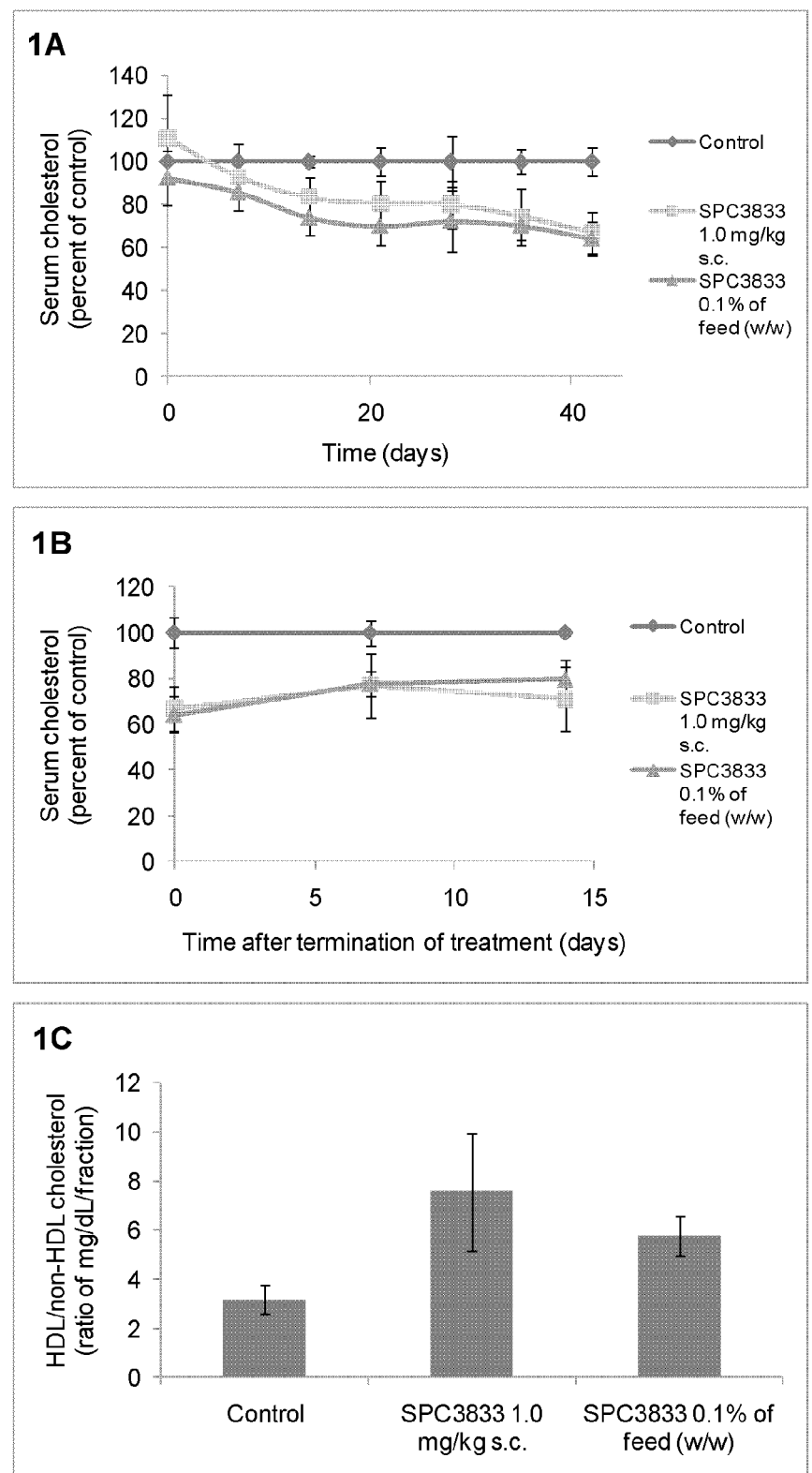
FIG. 1: Serum cholesterol levels

Results:

It has previously been shown that injection with anti-sense molecules directed against mouse apolipoprotein B (apoB) results in potent down-regulation of serum cholesterol. The present data clearly illustrates that an anti-apoB LNA oligonucleotide, SPC3833, decrease serum cholesterol when added together with a penetration enhancer directly into mouse feed. The down-regulation of serum cholesterol, compared to control animals, was significant already after the first week of treatment (15% down-regulation, P=0.0006). The down-regulation of serum cholesterol stayed significant compared to control throughout the six week treatment period (FIG. 1A) with a continued effect demonstrated at two weeks after termination of treatment (FIG. 1B). FPLC analysis demonstrated that the decrease in serum cholesterol was mainly the result of lower level of apoB-containing lipoproteins (very low density and low density lipoproteins) resulting in a more beneficial HDL/non-HDL (high density lipoprotein) ratio, i.e. a lipoprotein profile considered beneficial in atherosclerosis (FIG. 3C). The effect on serum cholesterol during treatment and wash-out was almost identical to the effect of SPC3833 injected weekly at 1.0 mg/kg during the six week treatment period. Serum triglyceride levels were significantly lower in both groups receiving SPC3833, both at termination of study and after two weeks of wash-out (FIG. 3A).

Liver apoB mRNA content was analyzed at termination of treatment and after two weeks of wash-out (FIG. 2). At termination of treatment there was a significant down-regulation of apoB mRNA levels in livers from animals that received SPC3833 via oral administration (48% down-regulation, P=0.005) or weekly injections (1.0 mg/kg/week, 60% down-regulation, P=0.002). Two weeks after termination of treatment, i.e. after the wash-out period, liver mRNA levels had returned to control levels in the oral administration group (FIG. 2).

Regardless of administration pathway treatment with SPC3833 resulted in a small but significant increase in serum ALT levels (FIG. 3B). It should be pointed out that the increase in serum ALT did not reach levels three times those on control animals (a level typically considered a sign of liver toxicity) and that serum ALT levels had returned to control levels after the two week wash-out period (FIG. 3B).

Example 2

The mouse studies of Example 1 are repeated but the following oligonucleotides are used, independently, in place of SPC3833 (Compound A):

Example 3

Intrajejunal/Duodenal Delivery of LNA Oligonucleotides

This series of experiments establishes a model system that allows quantitative assessment of the oral bioavailability of LNA oligonucleotides, such as Compounds A, C, B or D. They identify critical factors for increasing the oral bioavailability of LNA oligonucleotides and formulation attributes required of the human dosage form, and provide further evidence of effective maintenance of and creation of pharmacological responses can be accomplished with oral dosing antisense oligonucleotides. The most flexible and repeatable model for assessment of oral absorption is the intrajejunally/intraduodenally placed catheter. In man, catheters are placed by passage down the nasal canal and terminally located with imaging techniques. Animal models (pig, dog and monkey) are created by surgical placement of the catheter. Dog and monkey models provide the best candidates for repeated experimental iterations; catheters with subcutaneous access ports are often maintained for more than 18 months, with only a 10-20% drop out rate of subjects. The effect and requirement of penetration enhancer is determined. The use of formulations to avoid the dilution and low pH of the stomach are determined.

The animals are cycled through a series of formulation/chemistry variables with appropriate washout periods in-between each experiment. Typically, 24 hr plasma curves and blood chemistries are monitored. The following data is obtained:

a. IV pharmacokinetic baselines
b. Native Oligo Oral Bioavailability
c. Oral Bioavailability Enhancement as a Function of PE Dose
d. Oral Bioavailability as a Function of Drug Dose and Dose Volume
e. Pharmacology Onset after Oral Dosing
f. Pharmacology Maintenance with Oral dosing after an Efficacious Loading Dose
g. Oral Bioavailability as a Function of Size or Chemistry The animals used are male cynomologus monkeys weighing ~3-5 Kg, surgically fitted with intrajejunal/intraduodenal catheters with S.Q. access ports. Housing: Individual, standard cages and bedding. Food and Water: Ad libitum. Animal Care: Standard care with daily gross observations and once weekly catheter flushes. Blood loss from sampling is limited to 15 mL/Kg every 21 days; this determines the schedule of events list below.

Dosage Assumptions:

Previous primate studies with SPC3833 have shown single and multiple IV doses from 2 to 8 mg/kg were effective in producing robust pharmacological responses and doses up to 32 mg/kg were well tolerated. A conservative oral BAV assumption of at least 10%, such as at least 15% is utilized in establishing this model. Once a PE level is selected doses are adjusted based upon the performance measured (oral BAV obtained). Six animals are divided into two groups as described in the table below:

| Study Day | Group A | Group B |
|---|---|---|
| −14 | ID Catheter Placement | ID Catheter Placement |
| 1 | No PE/80 mpk Compound A ID 2 mL/Kg Reduced Sampling | No PE/80 mpk Compound A ID 2 mL/Kg Reduced Sampling |
| 8 | 2 mpk Compound A IV 100 uL/Kg Increased Sampling (48 & 72 hr) | 2 mpk Compound A IV 100 uL/Kg Increased Sampling (48 & 72 hr) |
| 15 | 25 mpk PE/20 mpk Compound A ID 2 mL/Kg | 25 mpk PE/80 mpk Compound A ID 2 mL/Kg |
| 22 | No Treatments | No Treatments |
| 36 | 100 mpk PE/80 mg/kg Compound A ID 4 mL/Kg | 100 mpk PE/20 mpk Compound A ID 2 mL/Kg Increased Sampling (48 & 72 hr) |
| 43 | 100 mpk PE/80 mpk Compound A ID 2 mL/Kg Increased Sampling (48 & 72 hr) | 100 mpk PE/80 mpk Compound A ID 1 mL/Kg |
| 50 | No Treatments | No Treatments |
| 57 | 5 mpk Compound B IV 100 uL/Kg Increased Sampling (48 & 72 hr) | 5 mpk Compound B IV 100 uL/Kg Increased Sampling (48 & 72 hr) |
| 64 | No PE/20 mpk Compound B ID 2 mL/Kg Reduced Sampling | No PE/20 mpk Compound B ID 2 mL/Kg Reduced Sampling |
| 67 | 100 mpk PE/20 mpk Compound B ID 2 mL/Kg | 100 mpk PE/20 mpk Compound B ID 2 mL/Kg |
| 74 | No Treatment | No Treatment |
| 81 | 5 mpk Compound C IV 100 uL/Kg Increased Sampling (48 & 72 hr) | 5 mpk Compound C IV 100 uL/Kg Increased Sampling (48 & 72 hr) |
| 88 | No PE/20 mpk Compound C ID 2 mL/Kg Reduced Sampling | No PE/20 mpk Compound C ID 2 mL/Kg Reduced Sampling |
| 91 | 100 mpk PE/20 mpk Compound C ID 2 mL/Kg | 100 mpk PE/20 mpk Compound C ID 2 mL/Kg |
| 98 | No Treatment | No Treatment |
| 105 | 5 mpk Compound D IV 100 uL/Kg Increased Sampling (48 & 72 hr) | 5 mpk Compound D IV 100 uL/Kg Increased Sampling (48 & 72 hr) |
| 112 | No PE/20 mpk Compound D ID 2 mL/Kg Reduced Sampling | No PE/20 mpk Compound D ID 2 mL/Kg Reduced Sampling |
| 115 | 100 mpk PE/20 mpk Compound D ID 2 mL/Kg | 100 mpk PE/20 mpk Compound D ID 2 mL/Kg |
| 122 | No Treatment | No Treatment |
| 123-144 | Treatment Phase - Pharmacology | Treatment Phase - Pharmacology |
| 144-165 | No Treatment - Pharmacology | No Treatment - Pharmacology |

Mpk = mg/kg

Compound A, B, C or compound D may be substituted with other oligonucleotides, such as compound E or F or other LNA oligonucleotides, such as those listed, referenced or provided herein IV/SQ Compound A:

Lyophilized Compound A, 50 mg/vial, is reconstituted with 2.5 mL of normal saline and is held in a refrigerator less than 24 hours before scheduled IV dosings.

IJ/ID Compound A, B, C or Compound D:

IJ/ID dosing volumes are set to 2.0 mL/Kg body weight (unless studying the volume effect). Sodium caprate is formulated at either 12.5 mg/mL or 50 mg/mL. Compound A or Compound B is formulated at either 10 mg/mL or 40 mg/mL. A 1.0 mL line flush of saline will follow each IJ/ID dosing.

Drug Assay:

The plasma drug assay is an enzyme-linked immunosorbent assay requiring 100 uL of plasma for dilution.

Total Cholesterol:

Standard.

HDL: Standard.

Triglygerides:

Standard.

ApoB:

Standard human kit.

microRNA targets—hybridisation Elisa and microRNA mRNA target derepression assays and biodistribution assays—see WO 2009/043353.

| Study Day | Observations, Measurements, Specimens |
|---|---|
| 1 | Plasma PK (0.5 mL blood/sample): −.5, 1, 2, 4, 6, 24 hr TG, total cholesterol, HDL, apoB |
| 15 | Plasma PK (0.5 mL blood/sample): −.5, 0.5, 1, 1.5, 2, 3, 4, 6, 24, 48, 72 hr TG, total cholesterol, HDL, apoB |
| 22 | Plasma PK (0.5 mL blood/sample): −.5, 0.5, 1, 1.5, 2, 3, 4, 6, 24 hr TG, total cholesterol, HDL, apoB |
| 29 | TG, total cholesterol, HDL, apoB |
| 36 | Plasma PK (0.5 mL blood/sample): −.5, 0.5, 1, 1.5, 2, 3, 4, 6, 24 (48 & 72 hr for one group) hr TG, total cholesterol, HDL, apoB |
| 43 | Plasma PK (0.5 mL blood/sample): −.5, 0.5, 1, 1.5, 2, 3, 4, 6, 24 (48 & 72 for one group) hr TG, total cholesterol, HDL, apoB |
| 50 | TG, total cholesterol, HDL, apoB, and drug |
| 57 | Plasma PK (0.5 mL blood/sample): −.5, 0.5, 1, 1.5, 2, 3, 4, 6, 24, 48, 72 hr TG, total cholesterol, HDL, apoB |
| 64 | Plasma PK (0.5 mL blood/sample): −.5, 1, 2, 4, 6, 24 hr TG, total cholesterol, HDL, apoB |
| 67 | Plasma PK (0.5 mL blood/sample): −.5, 0.5, 1, 1.5, 2, 3, 4, 6, 24 hr TG, total cholesterol, HDL, apoB |
| 74 | TG, total cholesterol, HDL, apoB, and drug |
| 81 | Plasma PK (0.5 mL blood/sample): −.5, 0.5, 1, 1.5, 2, 3, 4, 6, 24, 48, 72 hr TG, total cholesterol, HDL, apoB |
| 88 | Plasma PK (0.5 mL blood/sample): −.5, 1, 2, 4, 6, 24 hr TG, total cholesterol, HDL, apoB |
| 91 | Plasma PK (0.5 mL blood/sample): −.5, 0.5, 1, 1.5, 2, 3, 4, 6, 24 hr TG, total cholesterol, HDL, apoB |
| 105 | TG, total cholesterol, HDL, apoB, and drug |
| 112 | Plasma PK (0.5 mL blood/sample): −.5, 0.5, 1, 1.5, 2, 3, 4, 6, 24, 48, 72 hr TG, total cholesterol, HDL, apoB |
| 115 | Plasma PK (0.5 mL blood/sample): −.5, 1, 2, 4, 6, 24 hr TG, total cholesterol, HDL, apoB |
| 122 | Plasma PK (0.5 mL blood/sample): −.5, 0.5, 1, 1.5, 2, 3, 4, 6, 24 hr TG, total cholesterol, HDL, apoB |

TG = triglycerides

Example 4

IJ/ID Bioavailability Determination

This protocol describes a well characterized model for the in vivo, quantitative assessment of oligonucleotide oral bioavailability. This model works well for solution formulations with or without permeation enhancers. A series of experiments are suggested to define oral bioavailability of a particular oligonucleotide using the industry standard penetration enhancer (C10) and/or other penetration enhancers.

Rationale:

The most flexible and repeatable model for assessment of oral absorption is the intrajejunally/intraduodenally placed catheter. The use of solution formulations removes one element of variability (dosage form dissolution) from the assessment. Despite this, a significant amount of variability remains from dose to dose, so the average effect seen in a group is required for decision making. Previously, groups of six animals per treatment proved to be satisfactory.

The animal is fasted for at least 12 hours, but not longer than 24 hours. An abdominal midline incision is made to expose the jejunum or duodenum. The catheter is tunneled subcutaneously and exteriorized at the scapula region. The abdominal incision is closed with suture and the skin incision with wound clips. The catheter is filled with sterile saline and plugged. The excess length of catheter is tucked into the subcutaneous skin pocket. The catheter plug is left exposed and is secured using a wound clip.

Absolute bioavailability is calculated by reference to intravenous injection of the oligonucleotides at a dose of 2 or 5 mg/kg. Intrajejunal/intraduodenal administration is assessed after infusion of 10-80 mg/kg oligonucleotide administered through the implanted intrajejunal/intraduodenal catheter followed by a sterile water flush. Blood samples are collected at predetermined time points after single-dose administration to allow for pharmacokinetic analysis. Typically, plasma AUCs can be estimated suitably from samples obtained at times between 0 and 24 hours. (Urine can be collected over 24-h intervals following administration.) If information is required regarding intestinal stability or organ accumulation of an oligonucleotide, selected animals can be humanely euthanized at 1 to 24 h after dose administration. The concentration of oligonucleotide in plasma and tissue samples is typically determined by a hybridisation Elisa assay using a detection probe and a capture probe. In the penetration enhanced studies, sufficient drug is absorbed so that other less sensitive methods may be used; however, care should be taken to assure measurement of intact, full length material only.

Using the above methodology, compounds A and B was found to have a bioavailability of 5.8% in a Cynomolgous monkey study according to the protocol of example 3.

|  |  | Bioavailability (in %) | |
|---|---|---|---|
|  | Dose [mg/kg] | Without penetration enhancer (PE) | With PE *100 mg/kg |
| Compound A | 20 | 0.77 | 5.8 |
| Compound B | 20 | 1.1 | 5.8 |

Taking a factor of 1.3×–1.6×, the average BAV in humans can be predicted to be between 7.5-9.3%.

Example 5

Determination of dosing schedule for accumulation in target tissues. The decrease over time (from $t_1$ to $t_2$) in concentration (C) of a particular oligonucleotide in a target tissue can in general be described as $C2=C1*e^{-k*t}$ (first order process) =>and taking natural logs yields $\ln C2=\ln C1-(k*t)$, where $k=\ln 2/t_{1/2}$ Thus, for a particular oligonucleotide in a particular tissue, the concentration decreases with time according to the equation and the decrease is dependent of the half-life and sampling time. If the half-life is long enough it could result in accumulation of the compound upon repeated dosing. In our case, the half-life is 27.2 days and dosing is repeated every week (the interval of administration, t, is 7 days). This means that a retained concentration of the compound will decrease in a constant way, $\ln 2/t_{1/2} \times t$. In our case, $\ln 2/27.2 \times 7=0.178$ Using this information, and the knowledge that a 1 mg/kg dose will yield 3 µg/g compound in the liver, it is possible to prepare the plot below. It is also possible to calculate a dose to maintain a certain level of the compound, using the same equation (inserted in the plot).

In this study, an effective dosage level of 30 µg/kg in the target tissue (liver) was obtained initially by weekly subcutaneous injection of 3 mg/kg of the particular oligonucleotide for 5 weeks see FIG. 4. The effective dose was subsequently maintained by intraduodenal administration once weekly of 33 mg/kg/administration (+100 mg/kg PE (penetration enhancer). If the effective dose is to be maintained in the monkeys by oral administration every second week, the dose need to be doubled i.e. to 67 mg/kg/administration.

A bioavailability of 5.8 in Cynomolgus monkeys would correspond to approximately 10-15% in humans. If bioavailability in humans is set to be 10%, then the dosages needed to maintain the effective dosage level would be proportionately lower, i.e. 20 mg/kg/administration at a once weekly dosing and 40 mg/kg/administration when dosed every second week (both when compared to the 33 and 67 mg/kg/administration above).

Example 6

IJ Delivery of LNA oligmers in primates.

As per Example 3, except the following protocol was used (six animals/group):

| Study Day | Group A | Group B |
|---|---|---|
| −14 | ID Catheter Placement | ID Catheter Placement |
| 1 | No PE/80 mpk COMP'A ID 2 mL/Kg Reduced Sampling | No PE/80 mpk COMP'A ID 2 mL/Kg Reduced Sampling |
| 8 | 2 mpk COMP'A IV 100 uL/Kg Increased Sampling (48 & 72 hr) | 2 mpk COMP'A IV 100 uL/Kg Increased Sampling (48 & 72 hr) |
| 15 | 25 mpk PE/20 mpk COMP'A ID 2 mL/Kg | 25 mpk PE/80 mpk COMP'A ID 2 mL/Kg |
| 22 | No Treatments | No Treatments |
| 36 | 100 mpk PE/80 mg/kg COMP'A ID 4 mL/Kg | 100 mpk PE/20 mpk COMP'A ID 2 mL/Kg Increased Sampling (48 & 72 hr) |
| 43 | 100 mpk PE/80 mpk COMP'A ID 2 mL/Kg Increased Sampling (48 & 72 hr) | 100 mpk PE/80 mpk COMP'A ID 1 mL/Kg |
| 50 | No Treatments | No Treatments |
| 57 | 5 mpk COMPB IV 100 uL/Kg Increased Sampling (48 & 72 hr) | 5 mpk COMPB IV 100 uL/Kg Increased Sampling (48 & 72 hr) |
| 64 | No PE/20 mpk COMPB ID 2 mL/Kg Reduced Sampling | No PE/20 mpk COMPB ID 2 mL/Kg Reduced Sampling |
| 67 | 100 mpk PE/20 mpk COMPB ID 2 mL/Kg | 100 mpk PE/20 mpk COMPB ID 2 mL/Kg |
| 74 | No Treatment | No Treatment |
| 81 | 5 mpk COMPC IV 100 uL/Kg Increased Sampling (48 & 72 hr) | 5 mpk COMPC IV 100 uL/Kg Increased Sampling (48 & 72 hr) |
| 88 | No PE/20 mpk COMPC ID 2 mL/Kg Reduced Sampling | No PE/20 mpk COMPC ID 2 mL/Kg Reduced Sampling |
| 91 | 100 mpk PE/20 mpk COMPC ID 2 mL/Kg | 100 mpk PE/20 mpk COMPC ID 2 mL/Kg |
| 98 | No Treatment | No Treatment |
| 105 | 5 mpk COMPD IV 100 uL/Kg Increased Sampling (48 & 72 hr) | 5 mpk COMPD IV 100 uL/Kg Increased Sampling (48 & 72 hr) |
| 112 | No PE/20 mpk COMPD ID 2 mL/Kg Reduced Sampling | No PE/20 mpk COMPD ID 2 mL/Kg Reduced Sampling |
| 115 | 100 mpk PE/20 mpk COMPD ID 2 mL/Kg | 100 mpk PE/20 mpk COMPD ID 2 mL/Kg |
| 122 | No Treatment | No Treatment |
| 123-144 | Treatment Phase - Pharmacology | Treatment Phase - Pharmacology |
| 144-165 | No Treatment - Pharmacology | No Treatment - Pharmacology |

Procedure Schedule

| Study Day | Observations, Measurements, Specimens |
|---|---|
| 1 | Plasma PK (0.5 mL blood/sample): −.5, 1, 2, 4, 6, 24 hr TG, total cholesterol, HDL, apoB |
| 15 | Plasma PK (0.5 mL blood/sample): −.5, 0.5, 1, 1.5, 2, 3, 4, 6, 24, 48, 72 hr TG, total cholesterol, HDL, apoB |
| 22 | Plasma PK (0.5 mL blood/sample): −.5, 0.5, 1, 1.5, 2, 3, 4, 6, 24 hr TG, total cholesterol, HDL, apoB |
| 29 | TG, total cholesterol, HDL, apoB |
| 36 | Plasma PK (0.5 mL blood/sample): −.5, 0.5, 1, 1.5, 2, 3, 4, 6, 24 (48 & 72 hr for one group) hr TG, total cholesterol, HDL, apoB |
| 43 | Plasma PK (0.5 mL blood/sample): −.5, 0.5, 1, 1.5, 2, 3, 4, 6, 24 (48 & 72 for one group) hr TG, total cholesterol, HDL, apoB |
| 50 | TG, total cholesterol, HDL, apoB, and drug |
| 57 | Plasma PK (0.5 mL blood/sample): −.5, 0.5, 1, 1.5, 2, 3, 4, 6, 24, 48, 72 hr TG, total cholesterol, HDL, apoB |
| 64 | Plasma PK (0.5 mL blood/sample): −.5, 1, 2, 4, 6, 24 hr TG, total cholesterol, HDL, apoB |
| 67 | Plasma PK (0.5 mL blood/sample): −.5, 0.5, 1, 1.5, 2, 3, 4, 6, 24 hr TG, total cholesterol, HDL, apoB |
| 74 | TG, total cholesterol, HDL, apoB, and drug |
| 81 | Plasma PK (0.5 mL blood/sample): −.5, 0.5, 1, 1.5, 2, 3, 4, 6, 24, 48, 72 hr TG, total cholesterol, HDL, apoB |
| 88 | Plasma PK (0.5 mL blood/sample): −.5, 1, 2, 4, 6, 24 hr TG, total cholesterol, HDL, apoB |
| 91 | Plasma PK (0.5 mL blood/sample): −.5, 0.5, 1, 1.5, 2, 3, 4, 6, 24 hr TG, total cholesterol, HDL, apoB |
| 105 | TG, total cholesterol, HDL, apoB, and drug |
| 112 | Plasma PK (0.5 mL blood/sample): −.5, 0.5, 1, 1.5, 2, 3, 4, 6, 24, 48, 72 hr TG, total cholesterol, HDL, apoB |
| 115 | Plasma PK (0.5 mL blood/sample): −.5, 1, 2, 4, 6, 24 hr TG, total cholesterol, HDL, apoB |
| 122 | Plasma PK (0.5 mL blood/sample): −.5, 0.5, 1, 1.5, 2, 3, 4, 6, 24 hr TG, total cholesterol, HDL, apoB |
| TBD | Pharmacology |
| Daily | observation |
| Weekly | Weights, catheter flush |
| Termination | |

The results are shown in FIG. 9.

Example 7

Baseline Dosing Parameters PK & Oral BAV of Compound A Compound A was administered as in Example 4. The following results were obtained.

| PE (mg/kg) | Drug (mg/kg) | Dose Vol (mL/kg) | BAV (% IV ± Range) |
|---|---|---|---|
| 0 | 80 | 2 | 0.74 (0.3-1.5) |
| 25 | 20 | 2 | 3.0 (2.1-4.3) |
| 25 | 80 | 2 | 1.9 (1.8-2.1) |
| 100 | 20 | 2 | 5.8 (2.5-10.3) |
| 100 | 80 | 1 | 2.2 (0.7-3.8) |
| 100 | 80 | 2 | 3.4 (2.7-4.1) |
| 100 | 80 | 4 | 5.8 (4.3-6.7) |

Example 8

Baseline Dosing Parameters PK & Oral BAV of Compound B

Compound B was administered as in Example 4. The following results were obtained.

| PE (mg/kg) | Drug (mg/kg) | Dose Vol (mL/kg) | BAV (% IV ± Range) |
|---|---|---|---|
| 0 | 20 | 2 | 1.1 (0.3-1.9) |
| 100 | 20 | 2 | 5.8 (2.7-9.2) |

Example 9

Baseline Dosing Parameters PK & Oral BAV of Compound C

Compound C was administered as in Example 4. The following results were obtained.

| PE (mg/kg) | Drug (mg/kg) | Dose Vol (mL/kg) | BAV (% IV ± Range) |
|---|---|---|---|
| 0 | 20 | 2 | <LOQ |
| 100 | 20 | 2 | 4.4 (2.1-7.9) |

Example 10

Baseline Dosing Parameters PK & Oral BAV of Compound D

Compound D was administered as in Example 4.

| PE (mg/kg) | Drug (mg/kg) | Dose Vol (mL/kg) | BAV (% IV ± Range) |
|---|---|---|---|
| 0 | 20 | 2 | 1% |
| 100 | 20 | 2 | 6.7% |

Example 11

Dosage Optimisation—Compound A. Compound A was administered as in Example 4.

| PE (mg/kg) | Drug (mg/kg) | Dose Vol (mL/kg) | BAV (% IV ± Range) | PR/Drug | PE/Vol | Drug/Vol |
|---|---|---|---|---|---|---|
| 100 | 5 | 2 | 9.3 (4.0-16) | 20 | 50 | 2.5 |
| 100 | 20 | 4 | 4.7 (2.1-9.3) | 5 | 25 | 5 |
| 100 | 20 | 8 | 5.1 (2.2-11) | 5 | 12.5 | 2.5 |
| 200 | 20 | 4 | 6.1 (3.5-9.5) | 10 | 50 | 5 |
| 200 | 20 | 8 | 6.8 (3.2-12) | 10 | 25 | 2.5 |
| 300 | 15 | 6 | 11.3 (8.1-13) | 20 | 50 | 2.5 |
| 0 | 80 | 2 | 0.74 (0.3-1.5) | 1.25 | 12.5 | 10 |
| 25 | 20 | 2 | 3.0 (2.1-4.3) | 0.3125 | 12.5 | 40 |
| 25 | 80 | 2 | 1.9 (1.8-2.1) | 5 | 50 | 10 |
| 100 | 20 | 2 | 5.8 (2.5-10.3) | 1.25 | 100 | 80 |
| 100 | 80 | 1 | 2.2 (0.7-3.8) | 1.25 | 50 | 40 |
| 100 | 80 | 2 | 3.4 (2.7-4.1) | 1.25 | 25 | 20 |
| 100 | 80 | 4 | 5.8 (4.3-6.7) | PR/Drug | PE/Vol | Drug/Vol |

See also FIGS. 4-8 which represents this data graphically.

The invention claimed is:

1. A method for treating a disorder selected from the group consisting of hyperlipidemia, HDL/LDL cholesterol imbalance, dyslipidemia, coronary artery disease (CAD), coronary heart disease (CHD), and atherosclerosis, comprising orally administering a composition comprising an LNA oligomer that targets ApoB and a penetration enhancer selected from the group consisting of: a fatty acid, a bile acid, a chelating agent, an anionic cationic surfactant, and a non-chelating non-surfactant, or pharmaceutically acceptable salts thereof, wherein the ratio between the penetration enhancer and LNA oligomer is at least 5:1 (w/w), and wherein the LNA oligomer is administered at less than 50 mg/kg.

2. The method of claim 1 wherein the LNA oligomer is between 8 and 16 nucleobases in length.

3. The method of claim 1 wherein the human oral bioavailability of the LNA oligomer is at least 10%.

4. The method of claim 1 wherein the penetration enhancer is reversible paracellular junction modulator.

5. The method of claim 1 wherein the ratio of penetration enhancer to LNA oligomer is at least 10:1 (w/w).

6. The method of claim 1 wherein in the oral administration is preceded by intravenous administration of the LNA oligomer.

7. The method of claim 1 wherein the oral administration reduces the level of serum cholesterol.

8. The method of claim 1 wherein the oral administration reduces the level of serum HDL.

9. A method for inhibiting ApoB expression, comprising orally administering a composition comprising an LNA oligomer that targets ApoB and a penetration enhancer selected from the group consisting of: a fatty acid, a bile acid, a chelating agent, an anionic cationic surfactant, and a non-chelating non-surfactant, or pharmaceutically acceptable salts thereof, wherein the ratio between the penetration enhancer and LNA oligomer is at least 5:1 (w/w), and wherein the LNA oligomer is administered at less than 50 mg/kg.

10. The method of claim 9 wherein the oral administration reduces the level of serum cholesterol.

11. The method of claim 9 wherein the oral administration reduces the level of serum HDL.

12. The method of claim 1 wherein the dyslipidemia is selected from the group consisting of: familial combined hyperlipidemia (FCHL), acquired hyperlipidemia, hypercholesterolemia, and statin-resistant hypercholesterolemia.

13. The method of claim 1 or 9 wherein the LNA oligomer is administered at a dose of less than 10 mg/kg.

14. The method of claim 1 or 9 wherein the LNA oligomer is administered with a drink or taken with food.

15. The method of claim 1 or 9, wherein the oral administration is preceded by a parenteral pre-dose of the LNA oligomer, which is administered at least one day prior to the oral administration of the LNA oligomer.

16. The method of claim 1 or 9, wherein the LNA oligomer is orally administered at least once per week.

17. The method of claim 1 or 9, wherein the LAN oligomer is a gapmer.

* * * * *

SEQUENCE LISTING

```
<160> NUMBER OF SEQ ID NOS: 38

<210> SEQ ID NO 1
<211> LENGTH: 15
<212> TYPE: DNA
<213> ORGANISM: artificial
<220> FEATURE:
<223> OTHER INFORMATION: Oligomer sequence
<220> FEATURE:
<221> NAME/KEY: misc_feature
<222> LOCATION: (1)..(15)
<223> OTHER INFORMATION: Resdiues 1, 3, 4, 6, 7, 8, 10, 12, 14 & 15 are
      LNA units, remainder are DNA units. Internucleoside linkages are
      preferably phosphorothioate. LNA cytosines are all preferably
      methylated/5-methyl cytosine.

<400> SEQUENCE: 1
tcagtctgat aagct                                                    15

<210> SEQ ID NO 2
<211> LENGTH: 15
<212> TYPE: DNA
<213> ORGANISM: artificial
<220> FEATURE:
<223> OTHER INFORMATION: Oligomer sequence
<220> FEATURE:
<221> NAME/KEY: misc_feature
<222> LOCATION: (1)..(15)
<223> OTHER INFORMATION: Resdiues 1, 3, 5, 6, 7, 10, 11, 12, 14 & 15 are
      LNA units, remainder are DNA units. Internucleoside linkages are
      preferably phosphorothioate. LNA cytosines are all preferably
      methylated/5-methyl cytosine.

<400> SEQUENCE: 2
tcacaattag catta                                                    15

<210> SEQ ID NO 3
<211> LENGTH: 15
<212> TYPE: DNA
```

-continued

```
<213> ORGANISM: artificial
<220> FEATURE:
<223> OTHER INFORMATION: Oligomer sequence
<220> FEATURE:
<221> NAME/KEY: misc_feature
<222> LOCATION: (1)..(15)
<223> OTHER INFORMATION: Resdiues 1,3, 6, 7, 10, 12, 14 & 15 are LNA
      units, remainder are DNA units. Internucleoside linkages are
      preferably phosphorothioate. LNA cytosines are all preferably
      methylated/5-methyl cytosine.

<400> SEQUENCE: 3
ccattgtcac actcc                                                          15

<210> SEQ ID NO 4
<211> LENGTH: 10
<212> TYPE: DNA
<213> ORGANISM: artificial
<220> FEATURE:
<223> OTHER INFORMATION: Oligomer base sequence

<400> SEQUENCE: 4
gtcacactcc                                                                10

<210> SEQ ID NO 5
<211> LENGTH: 11
<212> TYPE: DNA
<213> ORGANISM: artificial
<220> FEATURE:
<223> OTHER INFORMATION: Oligomer base sequence

<400> SEQUENCE: 5
tgtcacactc c                                                              11

<210> SEQ ID NO 6
<211> LENGTH: 13
<212> TYPE: DNA
<213> ORGANISM: artificial
<220> FEATURE:
<223> OTHER INFORMATION: Oligomer base sequence

<400> SEQUENCE: 6
attgtcacac tcc                                                            13

<210> SEQ ID NO 7
<211> LENGTH: 14
<212> TYPE: DNA
<213> ORGANISM: artificial
<220> FEATURE:
<223> OTHER INFORMATION: Oligomer base sequence

<400> SEQUENCE: 7
cattgtcaca ctcc                                                           14

<210> SEQ ID NO 8
<211> LENGTH: 15
<212> TYPE: DNA
<213> ORGANISM: artificial
<220> FEATURE:
<223> OTHER INFORMATION: Oligomer base sequence

<400> SEQUENCE: 8
ccattgtcac actcc                                                          15

<210> SEQ ID NO 9
<211> LENGTH: 16
<212> TYPE: DNA
```

```
<213> ORGANISM: artificial
<220> FEATURE:
<223> OTHER INFORMATION: Oligomer base sequence

<400> SEQUENCE: 9
accattgtca cactcc                                                         16

<210> SEQ ID NO 10
<211> LENGTH: 17
<212> TYPE: DNA
<213> ORGANISM: artificial
<220> FEATURE:
<223> OTHER INFORMATION: Oligomer base sequence

<400> SEQUENCE: 10
caccattgtc acactcc                                                        17

<210> SEQ ID NO 11
<211> LENGTH: 18
<212> TYPE: DNA
<213> ORGANISM: artificial
<220> FEATURE:
<223> OTHER INFORMATION: Oligomer base sequence

<400> SEQUENCE: 11
acaccattgt cacactcc                                                       18

<210> SEQ ID NO 12
<211> LENGTH: 19
<212> TYPE: DNA
<213> ORGANISM: artificial
<220> FEATURE:
<223> OTHER INFORMATION: Oligomer base sequence

<400> SEQUENCE: 12
aacaccattg tcacactcc                                                      19

<210> SEQ ID NO 13
<211> LENGTH: 20
<212> TYPE: DNA
<213> ORGANISM: artificial
<220> FEATURE:
<223> OTHER INFORMATION: Oligomer base sequence

<400> SEQUENCE: 13
aaacaccatt gtcacactcc                                                     20

<210> SEQ ID NO 14
<211> LENGTH: 21
<212> TYPE: DNA
<213> ORGANISM: artificial
<220> FEATURE:
<223> OTHER INFORMATION: Oligomer base sequence

<400> SEQUENCE: 14
caaacaccat tgtcacactc c                                                   21

<210> SEQ ID NO 15
<211> LENGTH: 10
<212> TYPE: DNA
<213> ORGANISM: artificial
<220> FEATURE:
<223> OTHER INFORMATION: Oligomer base sequence

<400> SEQUENCE: 15
tgtcacactc                                                                10
```

```
<210> SEQ ID NO 16
<211> LENGTH: 12
<212> TYPE: DNA
<213> ORGANISM: artificial
<220> FEATURE:
<223> OTHER INFORMATION: Oligomer base sequence

<400> SEQUENCE: 16
attgtcacac tc                                                            12

<210> SEQ ID NO 17
<211> LENGTH: 11
<212> TYPE: DNA
<213> ORGANISM: artificial
<220> FEATURE:
<223> OTHER INFORMATION: Oligomer base sequence

<400> SEQUENCE: 17
attgtcacac t                                                             11

<210> SEQ ID NO 18
<211> LENGTH: 13
<212> TYPE: DNA
<213> ORGANISM: artificial
<220> FEATURE:
<223> OTHER INFORMATION: Oligomer base sequence

<400> SEQUENCE: 18
cattgtcaca ctc                                                           13

<210> SEQ ID NO 19
<211> LENGTH: 12
<212> TYPE: DNA
<213> ORGANISM: artificial
<220> FEATURE:
<223> OTHER INFORMATION: Oligomer base sequence

<400> SEQUENCE: 19
cattgtcaca ct                                                            12

<210> SEQ ID NO 20
<211> LENGTH: 14
<212> TYPE: DNA
<213> ORGANISM: artificial
<220> FEATURE:
<223> OTHER INFORMATION: Oligomer base sequence

<400> SEQUENCE: 20
ccattgtcac actc                                                          14

<210> SEQ ID NO 21
<211> LENGTH: 13
<212> TYPE: DNA
<213> ORGANISM: artificial
<220> FEATURE:
<223> OTHER INFORMATION: Oligomer base sequence

<400> SEQUENCE: 21
ccattgtcac act                                                           13

<210> SEQ ID NO 22
<211> LENGTH: 15
<212> TYPE: DNA
<213> ORGANISM: artificial
<220> FEATURE:
```

```
<223> OTHER INFORMATION: Oligomer base sequence

<400> SEQUENCE: 22
accattgtca cactc                                                        15

<210> SEQ ID NO 23
<211> LENGTH: 14
<212> TYPE: DNA
<213> ORGANISM: artificial
<220> FEATURE:
<223> OTHER INFORMATION: Oligomer base sequence

<400> SEQUENCE: 23
accattgtca cact                                                         14

<210> SEQ ID NO 24
<211> LENGTH: 16
<212> TYPE: DNA
<213> ORGANISM: artificial
<220> FEATURE:
<223> OTHER INFORMATION: Oligomer base sequence

<400> SEQUENCE: 24
caccattgtc acactc                                                       16

<210> SEQ ID NO 25
<211> LENGTH: 15
<212> TYPE: DNA
<213> ORGANISM: artificial
<220> FEATURE:
<223> OTHER INFORMATION: Oligomer base sequence

<400> SEQUENCE: 25
caccattgtc acact                                                        15

<210> SEQ ID NO 26
<211> LENGTH: 17
<212> TYPE: DNA
<213> ORGANISM: artificial
<220> FEATURE:
<223> OTHER INFORMATION: Oligomer base sequence

<400> SEQUENCE: 26
acaccattgt cacactc                                                      17

<210> SEQ ID NO 27
<211> LENGTH: 16
<212> TYPE: DNA
<213> ORGANISM: artificial
<220> FEATURE:
<223> OTHER INFORMATION: Oligomer base sequence

<400> SEQUENCE: 27
acaccattgt cacact                                                       16

<210> SEQ ID NO 28
<211> LENGTH: 18
<212> TYPE: DNA
<213> ORGANISM: artificial
<220> FEATURE:
<223> OTHER INFORMATION: Oligomer base sequence

<400> SEQUENCE: 28
aacaccattg tcacactc                                                     18
```

```
<210> SEQ ID NO 29
<211> LENGTH: 17
<212> TYPE: DNA
<213> ORGANISM: artificial
<220> FEATURE:
<223> OTHER INFORMATION: Oligomer base sequence

<400> SEQUENCE: 29
aacaccattg tcacact                                                  17

<210> SEQ ID NO 30
<211> LENGTH: 19
<212> TYPE: DNA
<213> ORGANISM: artificial
<220> FEATURE:
<223> OTHER INFORMATION: Oligomer base sequence

<400> SEQUENCE: 30
aaacaccatt gtcacactc                                                19

<210> SEQ ID NO 31
<211> LENGTH: 18
<212> TYPE: DNA
<213> ORGANISM: artificial
<220> FEATURE:
<223> OTHER INFORMATION: Oligomer base sequence

<400> SEQUENCE: 31
aaacaccatt gtcacact                                                 18

<210> SEQ ID NO 32
<211> LENGTH: 20
<212> TYPE: DNA
<213> ORGANISM: artificial
<220> FEATURE:
<223> OTHER INFORMATION: Oligomer base sequence

<400> SEQUENCE: 32
caaacaccat tgtcacactc                                               20

<210> SEQ ID NO 33
<211> LENGTH: 19
<212> TYPE: DNA
<213> ORGANISM: artificial
<220> FEATURE:
<223> OTHER INFORMATION: Oligomer base sequence

<400> SEQUENCE: 33
caaacaccat tgtcacact                                                19

<210> SEQ ID NO 34
<211> LENGTH: 22
<212> TYPE: DNA
<213> ORGANISM: artificial
<220> FEATURE:
<223> OTHER INFORMATION: Oligomer base sequence

<400> SEQUENCE: 34
caaacaccat tgtcacactc ca                                            22

<210> SEQ ID NO 35
<211> LENGTH: 13
<212> TYPE: DNA
<213> ORGANISM: artificial
```

```
<220> FEATURE:
<223> OTHER INFORMATION: Oligomer compound
<220> FEATURE:
<221> NAME/KEY: misc_feature
<222> LOCATION: (1)..(13)
<223> OTHER INFORMATION: Residues 1, 2, 11, 12 & 13 are beta-D-oxy LNA
      units, remaining residues are DNA units. Internucleoside linkages
      are phosphorothioate. LNA cytosines are y 5'methyl cytosine.

<400> SEQUENCE: 35
gtctgtggaa gcg                                                          13

<210> SEQ ID NO 36
<211> LENGTH: 13
<212> TYPE: DNA
<213> ORGANISM: artificial
<220> FEATURE:
<223> OTHER INFORMATION: Oligomer compound
<220> FEATURE:
<221> NAME/KEY: misc_feature
<222> LOCATION: (1)..(13)
<223> OTHER INFORMATION: residues 1, 2, 11, 12, 13 are beta-D-oxy-LNA
      units, LNA C are 5'methyl cytosine, remaining residues are DNA,
      fully phosphorothioate.

<400> SEQUENCE: 36
gcattggtat tca                                                          13

<210> SEQ ID NO 37
<211> LENGTH: 15
<212> TYPE: DNA
<213> ORGANISM: artificial
<220> FEATURE:
<223> OTHER INFORMATION: Oligomer compound
<220> FEATURE:
<221> NAME/KEY: misc_feature
<222> LOCATION: (1)..(15)
<223> OTHER INFORMATION: residues 1, 3, 6, 7, 10, 12, 14, & 15 are
      beta-D-oxy-LNA units, LNA Cs are 5'methyl cytosine, remaining
      residues are DNA, fully phosphorothioate.

<400> SEQUENCE: 37
ccattgtcac actcc                                                        15

<210> SEQ ID NO 38
<211> LENGTH: 12
<212> TYPE: DNA
<213> ORGANISM: artificial
<220> FEATURE:
<223> OTHER INFORMATION: Oligomer compound
<220> FEATURE:
<221> NAME/KEY: misc_feature
<222> LOCATION: (1)..(12)
<223> OTHER INFORMATION: residues 1, 2, 11 & 12 are beta-D-oxy-LNA
      units, LNA Cs are 5'methyl cytosine, remaining residues are DNA,
      fully phosphorothioate.

<400> SEQUENCE: 38
gttgacactg tc                                                           12
```